(12) United States Patent
Klein et al.

(10) Patent No.: US 7,351,534 B2
(45) Date of Patent: Apr. 1, 2008

(54) GENE MUTATION ASSOCIATED WITH AGE-RELATED MACULAR DEGENERATION

(75) Inventors: Michael L. Klein, Portland, OR (US); Dennis Schultz, Portland, OR (US)

(73) Assignee: Oregon Health & Sciences University, Portland, OR (US)

( * ) Notice: Subject to any disclaimer, the term of this patent is extended or adjusted under 35 U.S.C. 154(b) by 398 days.

(21) Appl. No.: 10/766,760

(22) Filed: Jan. 27, 2004

(65) Prior Publication Data

US 2006/0127915 A1 Jun. 15, 2006

Related U.S. Application Data

(60) Provisional application No. 60/443,214, filed on Jan. 27, 2003.

(51) Int. Cl.
*C12Q 1/68* (2006.01)
(52) U.S. Cl. .......................................................... 435/6
(58) Field of Classification Search ..................... None
See application file for complete search history.

(56) References Cited

U.S. PATENT DOCUMENTS 5,795,976 A 8/1998 Oefner et al.
6,453,244 B1 9/2002 Oefner

OTHER PUBLICATIONS

Lucentini et al (The Scientist (2004) vol. 18).*
Wacholder et al. (J. Natl. Cancer Institute (2004) 96(6):434-442).*
Allen et al. (DDT:Targets (2004) 3(6): 183-190).*
Zondervan et al. (Nature Reviews (2004) vol. 5: 89-100).*
Tuo et al. (Progress in Retinal and Eye Research (2004) vol. 23 229-249).*
Haddad et al. (Survey of Opthamology (2006) 51(4) 316-363).*
Klein et al. ("Age-related macular degeneration. Clinical features in a large family and linkage to chromosome 1q" Arch Ophthalmol. Aug. 1998;116(8):1082-8).*
Hubbard et al., *The Ensembl Genome Database Project*, Nucleic Acids Research, 30(1):38-41, 2002.
Iyengar et al., *A Genome-Wide Scan for Age-Related Maculopathy and Other Ocular Phenotypes in a Sample from the Beaver Dam Eye Study (BDES)*, Association for Research in Vision and Ophthalmology, Inc., www.iovs.org, 2002.
Marchant et al., *Use of Denaturing HPLC and Automated Sequencing to Screen the VMD2 Gene for Mutations Associated with Best's Vitelliform Macular Dystrophy*,Ophthalmic Genetics, 23(3):167-174, 2002.
Vogel et al., *Hemicentin, a Conserved Extracellular Member of the Immunoglobulin Superfamily, Organizes Epithelial and Other Cell Attachments into Oriented Line-Shaped Junctions*, DEVELOPMENT, 128:883-894, 2001.
Weeks et al., *Age-Related Maculopathy: An Expanded Genome-Wide Scan with Evidence of Susceptibility Loci Within the 1q31 and 17q25 Regions*, American Journal of Ophthalmology, 132(5):682-692, 2001.
Carpten et al., *A 6-Mb High-Resolution Physical and Transcription Map Encompassing the Hereditary Prostate Cancer 1 (HPC1) Region*, GENOMICS, 64:1-14, 2000.
Gorin et al., *The Genetics of Age-Related Macular Degeneration*, Molecular Vision, 5:29-34, 1999.
Stone et al., *A Single EFEMP1 Mutation Associated with Both Malattia Leventinese and Doyne Honeycomb Retinal Dystrophy*, Nature Genetics, 22:199-202, 1999.
Klein et al., *Age-Related Macular Degeneration: Clinical Features in a Large Family and Linkage to Chromosome 1q*, Archives of Ophthalmology, 116:1082-1088, 1998.
Petrukhin et al., *Identification of the Gene Responsible for Best Macular Dystrophy*, Nature Genetics, 19:241-247, 1998.
Klein et al., *The Five-Year Incidence and Progression of Age-Related Maculopathy*,Ophthalmology, 104(1):7-21, 1997.

* cited by examiner

*Primary Examiner*—Kenneth R. Horlick
*Assistant Examiner*—Christopher M. Babic
(74) *Attorney, Agent, or Firm*—Klarquist Sparkman, LLP

(57) ABSTRACT

The present invention describes the identification of a mutation in a human FIBL-6 protein, which mutation is associated with Familial Age-Related Macular Degeneration. Transcripts and products of this mutated gene are useful in detecting and diagnosing AMD, developing therapeutics for treatment of AMD, as well as the isolation and manufacture of the protein and the constructions of transgenic animals expressing the mutant genes.

13 Claims, 14 Drawing Sheets

Homo sapiens fibulin 6 (FIBL-6), mRNA
gi|20536570|ref|XM_053531.6|[20536570]

```
gaagccgcat ccagacaaaa gctgccgcat ccctgccctg cccaacccct ggagggattc      60
gagtttggtg cttgtccccg tctgattctc agcgccaaac ttttgctag ttcagagatt      120
ccaagagtct gatgagttac tctgagagga aaccctctgc ctgttgttga ggaggactga      180
gcacagtgct taggcgctga ggggggaaaaa gagggggaaa aaaagaaaa tgatttcctg      240
ggaagttgtc catacagtat tcctgtttgc tcttctttat cttccctag ctcaagatgc      300
gagccccag tcagagatca gagctgagga aattcccgag ggggcctcca cgttggcttt      360
tgtgtttgat gtgactggtt ctatgtatga tgatttagtt caggtgattg aaggggcttc      420
caaaattttg gagacgtctt tgaaaagacc taaaagacct cttttcaact ttgcgttggt      480
gcctttccat gatccagaaa ttggcccagt gacaattacc acagatccca agaaatttca      540
atatgaactc agagaactgt atgttcaggg tggtggtgat tgcccagaaa tgagtattgg      600
agctataaaa attgccttgg aaatttctct tcctggttct ttcatctatg ttttcactga      660
tgctcggtcc aaagattacc ggctcaccca tgaggtgctg caacttatcc aacagaaaca      720
gtcacaagtc gtatttgttc tgactggaga ttgtgatgca aggacccata ttggatataa      780
agtctatgaa gaaattgcct ctacaagttc tggtcaagtg ttccatctgg acaaaaaaca      840
agttaatgag gtattaaaat gggtagaaga agcagtacag gcctccaaag ttcacctttt      900
atccacagat catttggaac aggctgtaaa tacttggaga attcctttg atcccagcct      960
gaaagaggtc actgtgtctt tgagtgggcc ttctccaatg attgaaattc gcaatcctttt     1020
agggaagctg ataaaaaaagg gatttggcct gcatgagcta ttaaatatcc ataactctgc     1080
caaagtagtg aatgtgaaag agccagaggc tggaatgtgg acagtgaaga cctcaagcag     1140
tggaaggcac tctgttcgca ttactggcct cagtactatt gatttccgag ctggcttttc     1200
tcgaaagccc accctggact tcaaaaaaac agtcagcaga ccagtgcaag gaatacctac     1260
ctatgtactg ctcaatactt ctggaattttc cactccagct agaatagatc ttcttgaact     1320
tttgagtatc tcaggaagtt ctcttaagac tattcctgtt aaatattacc cacatcgaaa     1380
accttatggc atatggaata tttctgactt tgtaccacca aatgaagctt tctttctcaa     1440
agtaacaggc tatgataaag atgattacct cttccagaga gtatcaagtg tttcctttttc     1500
tagtattgtc ccagatgctc ccaaagttac gatgcctgag aaaaccccag gatactatct     1560
gcagccgggc caaattccct gctctgttga cagtcttttg ccctttacct tgagctttgt     1620
cagaaatgga gttacacttg gagtagacca gtatttgaaa gaatctgcca gtgtgaactt     1680
agatattgca aaggtcactt tgtctgacga aggtttctat gaatgcattg ctgtcagcag     1740
tgcaggtact ggacgggcac agacatttttt tgacgtatca gagcccccctc cggtcatcca     1800
agtgcctaac aatgttacag tcactcctgg agagagagca gttttaacat gtctcatcat     1860
cagtgcggtg gattacaatc taacctggca gaggaatgac agagatgtca gactggcaga     1920
gccagcgaga attaggacct tggctaatct gtcattggag ctaaagagtg tgaaattcaa     1980
cgatgctgga gagtatcatt gtatggtttc tagtgaaggt ggatcatcag ccgcttcagt     2040
tttcctcaca gtgcaagaac cacccaaagt cactgtgatg cccaagaatc agtctttcac     2100
aggagggtct gaggtctcca tcatgtgttc tgcaacaggt tatcccaaac caaagattgc     2160
ctggaccgtt aacgatatgt ttatcgtggg ttcacacagg tataggatga cctcagatgg     2220
taccttattt atcaaaaatg cagctcccaa agatgcaggg atctatggtt gcctagcaag     2280
taattcagct ggaacagata aacagaattc tactctcaga tacattgaag cccctaagtt     2340
gatggtagtt cagagtgagc tcttggttgc ccttggggat ataaccgtta tggaatgcaa     2400
aacctctggt attcctccac ctcaagttaa atggttcaaa ggagatcttg agttgaggcc     2460
ctcaacattc ctcattattg accctctctt gggacttttg aagattcaag aaacacaaga     2520
tctggatgct ggcgattata cctgtgtagc catcaatgag gctggaagag caactggcaa     2580
gataactctg gatgttggct cacctccagt tttcatacaa gaacctgctg atgtgtctat     2640
ggaaattggc tcaaatgtga cattccttg ttatgttcag ggttatccag aaccaacaat     2700
caaatggcga agattagaca acatgccaat ttttctcaaga ccttttcag ttagttccat     2760
cagccaacta agaacaggag ctctctttat tttaaactta tgggcaagtg ataaaggaac     2820
ctatatttgt gaagctgaaa accagtttgg aaagatccag tcagagacaa cagtaacagt     2880
gaccggactt gttgctccac ttattggaat cagcccttca gtggccaatg ttattgaagg     2940
acagcagctt actttgcccct gtactctgtt agctggaaat cccattccag aacgtcggtg     3000
gattaagaat tcagctatgt tgctccaaaa tccttacatc actgtgcgca gtgatgggag     3060
cctccatatt gaaagagttc agcttcagga tggtggtgaa tatacttgtg tggccagtaa     3120
cgttgctggg accaataaca aaactaccct tgtggttgtg catgttctgc caaccattca     3180
```

FIG. 7A

Homo sapiens fibulin 6 (FIBL-6), mRNA
gi|20536570|ref|XM_053531.6|[20536570]

```
gcatgggcag cagatactca gtacaattga aggcattcca gtaactttac catgcaaagc   3240
aagtggaaat cccaaaccgt ctgtcatctg gtccaagaaa ggagagctga tttcaaccag   3300
cagtgctaag ttttcagcag gagctgatgg tagtctgtat gtggtatcac ctggaggaga   3360
ggagagtggg gagtatgtct gcactgccac caatacagcc ggctacgcca aaaggaaagt   3420
gcagctaaca gtctatgtaa ggcccagagt gtttggagat caacgaggac tgtcccagga   3480
taagcctgtt gagatctccg tccttgcagg ggaagaggta acacttccat gtgaagtgaa   3540
gagcttacct ccacccataa ttacttgggc caaagaaacc cagctccatct caccgttctc   3600
tccaagacac acattcctcc cttctggttc aatgaagatc actgaaaccc gcacttcaga   3660
tagtgggatg tatctttgtg ttgccacaaa tattgctggg aatgtgactc aggctgtcaa   3720
attaaatgtc catgttcctc caaagataca gcgtggacct aaacatctca aagtccaagt   3780
tggtcaaaga gtggatattc catgtaatgc tcaagggact cctcttcctg taatcacctg   3840
gtccaaaggt ggaagcacta tgctggttga tggagagcac catgttagca atccagacgg   3900
aactttaagc atcgaccaag ccacgccctc agatgctggc atatatacat gtgttgctac   3960
taacatagca ggcactgatg aaacagagat aacgctacat gtccaagaac cacccacagt   4020
ggaagatcta gaacctccat ataacactac tttccaagaa agagtggcca atcaacgcat   4080
tgaatttcca tgtcctgcaa aagtacccc taaaccaacc atcaaatgt tacacaatgg   4140
tagagagttg acaggcagag agcctggcat ttctatcttg gaagatggca cattgctggt   4200
tattgcttct gttacaccct atgacaatgg ggagtacatc tgtgtggcag tcaatgaagc   4260
tggaaccaca gaaagaaaat ataaccctcaa agtccatgtt cctccagtaa ttaaagataa   4320
agaacaagtt acaaatgtgt cggtgttgtt aaatcagctg accaatctct tctgtgaagt   4380
ggaaggcact ccatctccca tcattatgtg gtataaagat aatgtccagg tgactgaaag   4440
cagcactatt cagactgtga acaatgggaa gatactgaag ctcttcagag ccactccaga   4500
ggatgcagga agatattcct gcaaagcaat taatattgca ggcacttctc agaagtactt   4560
taacattgat gtgctagttc caccaccat aataagtacc aacttcccaa atgaagtctc   4620
agttgtcctc aaccgtgacg tcgccttga atgccaggtc aaaggcactc cctttcctga   4680
tattcattgg ttcaaagatg gcaagccttt attttgggc gatcctaatg ttgaacttct   4740
agacagagga caagtcttac atttaaagaa tgcacggaga aatgacaagg ggcgctacca   4800
atgtactgtg tctaatgcag ctggcaaaca agccaaggat ataaaactga ctatctataa   4860
tcctcctagt attaaaggag gaaatgtcac cacagacata tcagtattga tcaacagcct   4920
tattaaactg gaatgtgaaa cacggggact tccaatgcct gccattactt ggtataagga   4980
cgggcagcca atcatgtcca gctcacaagc actttatctt gataaggac aatatcttca   5040
tattcctcga gcacaggtct ctgattcagc aacatatacg tgtcacgtag ccaatgttgc   5100
tggaactgct gaaaaatcat tccatgtgga tgtctatgtt cctccaatga ttgaaggcaa   5160
cttggccacg cctttgaata gcaagtagt tattgctcat tctctgacac tggagtgcaa   5220
agctgctgga aacccttctc ccattctcac ctggttgaaa gatggtgtac ctgtgaaagc   5280
taatgacaat atccgcatag aagctggtgg aagaaactc gaaatcatga gtgcccaaga   5340
aattgatcga ggacagtaca tatgcgtggc taccagtgtg gcaggagaaa aggaaatcaa   5400
atatgaagtt gatgtcttgg tgccaccagc tatagaagga ggagatgaaa catcttactt   5460
cattgtgatg gttaataact tactggagct agattgtgca gtgacaggct ctccccacc   5520
aactatcatg tggctgaagg atggccagtt aattgatgaa agggatggat tcaagatttt   5580
attaaatgga cgcaaactgg ttattgctca ggctcaagtg tcaaacacag gcctttatcg   5640
gtgcatggca gcaaatactg ctggagacca caagaaggaa tttgaagtga ctgttcatgt   5700
tcctccaaca atcaagtcct caggcctttc tgagagagtt gtggtaaaat acaagcctgt   5760
cgccttgcag tgcatagcca atgggattcc aaatccttcc attacatggt taaagatga   5820
ccagcctgtg aacactgccc aaggaaacct taaaatacag tcttctggtc gagttctaca   5880
aattgccaaa accctgttgg aagatgctgg cagatacaca tgtgtggcta ccaacgcagc   5940
tggagaaaca caacagcaca ttcaactgca tgttcatgaa ccacctagtc tggaagatgc   6000
tggaaaaatg ctgaatgaga ctgtgttggt gagcaaccct gtacagctgg agtgtaaggc   6060
agctggaaat cctgtgcctg ttattacatg gtacaaagat aatcgtctac tctcaggttc   6120
caccagcatg actttcttga acagaggaca gatcattgat attgaaagtg cccagatctc   6180
agatgctggc atatataaat gcgtggccat caactcagct ggagctacag agttatttta   6240
cagtctgcaa gttcatgtgg cccatcaatt tctggcagc aataacatgg tggcagtggt   6300
ggttaataac ccggtgaggt tagaatgtga agcagagggt attcctgccc caagtctgac   6360
ctggttgaaa gatgggagtc ctgtttctag tttttctaat ggattacagg ttctctctgg   6420
tggtcgaatc ctagcattga ccagtgcaca aatcagcgac acaggaaggt acacctgcgt   6480
ggcagtgaat gctgctggag aaaagcaaag ggacattgac ctccgagtat atgttccgcc   6540
aaatattatg ggagaagaac agaatgtctc tgtcctcatt agccaagctg tggaattact   6600
```

FIG. 7B

Homo sapiens fibulin 6 (FIBL-6), mRNA
gi|20536570|ref|XM_053531.6|[20536570]

```
atgtcaaagt gatgctattc ccccacctac tcttacttgg ttaaaagacg gccaccccCtt    6660
gctgaagaaa ccaggcctca gtatatctga aaatagaagt gtgttaaaga ttgaagatgc    6720
tcaggttcaa gacactggtc gttacacttg tgaagcaaca aatgttgctg gaaaaactga    6780
aaaaaactac aatgtcaaca tttgggtccc cccaaatatt ggtggttctg atgaacttac    6840
tcaacttaca gtcattgaag ggaatctcat tagtctgttg tgtgaatcaa gtggtattcc    6900
accccccaaat ctcatctgga agaagaaagg ctctccagtg ctgactgatt ccatgggggcg    6960
agttagaatt ttatctgggg gcaggcaatt acaaatttca attgctgaaa agtctgatgc    7020
agcactctat tcatgtgtgg cgtcgaatgt tgctgggact gcaaagaaag aatacaatct    7080
gcaagtttac attagaccaa ccataaccaa cagtggcagc caccctactg aaattattgt    7140
gacccgaggg aagagtatct ccttggagtg tgaggtgcag ggtattccac caccaacagt    7200
gacctggatg aaagatggcc acccccttgat caaggcaaag ggagtagaaa tactggatga    7260
aggtcacatc cttcagctga agaacattca tgtatctgac acaggccgtt atgtgtgtgt    7320
tgctgtgaat gtagcaggaa tgactgacaa aaaatatgac ttaagtgtcc atgctcctcc    7380
aagcatcata ggaaaccaca ggtcacctga aaatattagt gtggtagaaa agaactcagt    7440
atctttgact tgtgaagctt ctggaattcc cctgccttcc ataacctggt tcaaagatgg    7500
gtggcctgtc agccttagca attctgtgag gattctttca ggaggcagga tgctacggct    7560
gatgcagacc acaatggaag atgctggcca atatacttgc gttgtaagga atgcagctgg    7620
tgaagaaaga aaaatctttg ggctttcagt attagtacca cctcatattg tgggtgaaaa    7680
tacattggaa gatgtgaagg taaaagagaa acagagtgtt acgctgactt gtgaagtgac    7740
agggaatcca gtgccagaaa ttacatggca caaagatggg cagccccctcc aagaagatga    7800
agcccatcac attatatctg gtggccgttt tcttcaaatt accaatgtcc aggtgccaca    7860
cactggaaga tatacatgtt tggcttccag tccagctggc cacaagagca ggagcttcag    7920
tcttaatgta tttgtatctc ctacaattgc tggtgtaggt agtgatggca accctgaaga    7980
tgtcactgtc atccttaaca gccctacatc tttggtctgt gaagcttatt catatcctcc    8040
agctaccatc acctggttta aggatggcac tccttaagaa tctaaccgaa atattcgtat    8100
tcttccagga ggcagaactc tgcagatcct caatgcacag gaggacaatg ctggaagata    8160
ctcttgtgta gccacgaatg aggctgagaa aatgataaag cactatgaag tgaaggtgta    8220
cattccaccc ataatcaata aaggggacct ttggggcca ggtctttccc ctaaagaagt    8280
gaagatcaaa gtaaacaaca ctctgacctt ggaatgtgaa gcgtatgcaa ttccttctgc    8340
ctccctcagc tggtacaagg atggacagcc ccttaaatcc gatgatcatg ttaatattgc    8400
tgcgaatgga cacacacttc aaataaagga ggctcaaata tcagacaccg gacgatatac    8460
ttgtgtagca tctaacattg caggtgaaga tgagttggat tttgatgtga atattcaagt    8520
tcctccaagt tttcagaaac tctgggaaat aggaaacatg ctagatactg gcaggaatgg    8580
tgaagccaaa gatgtgatca tcaacaatcc catttctctt tactgtgaga caatgctgc    8640
tccccctcct acactgacat ggtacaaaga tggccaccct ctgacctcaa gtgataaagt    8700
attgattttg ccaggagggc gagtgttgca gattcctcgg gctaaagtag aagatgctgg    8760
gagatacaca tgtgtggctg tgaatgaggc tggagaagat tcccttcaat atgatgtccg    8820
tgtactcgtg ccgccaatta tcaagggagc aaatagtgat ctccctgaag aggtcaccgt    8880
gctggtgaac aagagtgcac tgatagagtg tttatccagt ggcagcccag caccaaggaa    8940
ttcctggcag aaagatggac agcccttgct agaagatgac catcataaat ttctatctaa    9000
tggacgaatt ctgcagattc tgaatactca ataacagat atcggcaggt atgtgtgtgt    9060
tgctgagaac acagctggga gtgccaaaaa atattttaac ctcaatgttc atgttcctcc    9120
aagtgtcatt ggtcctaaat ctgaaaatct taccgtcgtg gtgaacaatt tcatctcttt    9180
gacctgtgag gtctctggtt ttccaccctcc tgacctcagc tggctcaaga tgaacagcc    9240
catcaaactg aacacaaata ctctcattgt gcctggtggt cgaactctac agattattcg    9300
ggccaaggta tcagatggtg gtgaatacac ttgtatagct atcaatcaag ctggcgaaag    9360
caagaaaaag tttcccctga ctgtttatgt gcccccaagc attaaagacc atgacagtga    9420
atctctttct gtagttaatg taagagaggg aacttctgtg tctttggagt gtgagtcgaa    9480
cgctgtgcca cctccagtca tcacttggta taagaatggg cggatgataa cagagtctac    9540
tcatgtggag attttagctc atggacaaat gctacacatt aagaaagctg aggtatctga    9600
cacaggccag tatgtatgta gagctataaa tgtagcagga cgggatgata aaaatttcca    9660
cctcaatgta tatgtgccac ccagtattga aggacctgaa agagaagtga ttgtggagac    9720
gatcagcaat cctgtgacat taacatgtga tgccactggg atcccacctc ccacgatagc    9780
atggttaaag aaccacaagc gcatagaaaa ttctgactca ctggaagttc gtattttgtc    9840
tggaggtagc aaactccaga ttgcccggtc tcagcattca gatagtggaa actatacatg    9900
tattgcttca aatatggagg gaaaagccca gaaatattac tttctttcaa ttcaagttcc    9960
tccaagtgtt gctggtgctg aaattccaag tgatgtcagt gtccttctag gagaaaatgt    10020
```

FIG. 7C

Homo sapiens fibulin 6 (FIBL-6), mRNA
gi|20536570|ref|XM_053531.6|[20536570]

```
tgagctggtc tgcaatgcaa atggcattcc tactccactt attcaatggc ttaaagatgg   10080
aaagcccata gctagtggtg aaacagaaag aatccgagtg agtgcaaatg gcagcacatt   10140
aaacatttat ggagctctta catctgacac ggggaaatac acatgtgttg ctactaatcc   10200
cgctggagaa gaagaccgaa tttttaactt gaatgtctat gttacaccta caattagggg   10260
taataaagat gaagcagaga aactaatgac tttagtggat acttcaataa atattgaatg   10320
cagagccaca gggacgcctc caccacagat aaactggctg aagaatggac ttcctctgcc   10380
tctctcctcc catatccggt tactggcagc aggacaagtt atcaggattg tgagagctca   10440
ggtgtctgat gtcgctgtgt atacttgtgt ggcctccaac agagctgggg tggataataa   10500
gcattacaat cttcaagtgt ttgcaccacc aaatatggac aattcaatgg ggacagagga   10560
aatcacagtt ctcaaaggta gttccacctc tatggcatgc attactgatg gaaccccagc   10620
tcccagtatg gcctggctta gagatggcca gcctctgggg cttgatgccc atctgacagt   10680
cagcacccat ggaatggtcc tgcagctcct caaagcagag actgaagatt cgggaaagta   10740
cacctgcatt gcctcaaatg aagctggaga agtcagcaag cactttatcc tcaaggtcct   10800
agaaccacct cacattaatg gatctgaaga acatgaagag atatcagtaa ttgttaataa   10860
cccacttgaa cttacctgca ttgcttctgg aatcccagcc cctaaaatga cctggatgaa   10920
agatggccgg cccccttccac agacggatca agtgcaaact ctaggaggag gagaggttct   10980
tcgaatttct actgctcagg tggaggatac acatgtctgg catccagtcc   11040
tgcaggagat gatgataagg aatatctagt gagagtgcat gtacctccta atattgctgg   11100
aactgatgag ccccgggata tcactgtgtt acggaacaga caagtgacat ggaatgcaa   11160
gtcagatgca gtgccccac ctgtaattac ttggctcaga aatggagaac ggttacaggc   11220
aacacctcga gtgcgaatcc tatctggagg gagatacttg caaatcaaca atgctgacct   11280
aggtgataca gccaattata cctgtgttgc cagcaacatt gcaggaaaga ctacaagaga   11340
atttattctc actgtaaatg ttcctccaaa cataaagggg ggcccccaga gccttgtaat   11400
tctttttaaat aagtcaactg tattggaatg catcgctgaa ggtgtgccaa ctccaaggat   11460
aacatggaga aaggatggag ctgttctagc tgggaatcat gcaagatatt ccatcttgga   11520
aaatggattc cttcatattc aatcagcaca tgtcactgac actgacgtt atttgtgtat   11580
ggccaccaat gctgctgaa cagatcgcag gcgaatagat ttacaggtcc atgttcctcc   11640
atctattgct ccgggtccta ccaacatgac tgtaatagta aatgttcaaa ctactctggc   11700
ttgtgaggct actgggatac caaaaccatc aatcaattgg agaaaaaatg ggcatcttct   11760
taatgtggat caaaatcaga actcatacag gctcctttct tcaggttcac tagtaattat   11820
ttccccttct gtggatgaca ctgcaaccta tgaatgtact gtgacaaacg tgctggaga   11880
tgataaaaga actgtggatc tcactgtcca agttccacct tccatagctg atgagcctac   11940
agatttccta gtaaccaaac atgcccccagc agtaattacc tgcactgctt cgggagttcc   12000
atttccctca ccaaaaatgg tataagactg cttcccaggc gagatggcta   12060
tagaattctg tcctcaggag caattgaaat acttgccacc caattaaacc atgctggaag   12120
atacacttgt gtcgctagga atgcggctgg ctctgcacat cgacacgtga cccttcatgt   12180
tcatgagcct ccagtcattc agccccaacc aagtgaacta cacgtcattc tgaacaatcc   12240
tatttattta ccatgtgaag caacaggacc acccagtcct tcattactt ggcaaaaaga   12300
aggcatcaat gttaacactt caggcagaaa ccatgcagtt cttcctagtg gcggcttaca   12360
gatctccaga gctgtccgag aggatgctgg cacttacatg tgtgtggccc agaacccggc   12420
tggtacagcc ttgggcaaaa tcaagttaaa tgtccaagtt cctccagtca ttagccctca   12480
tctaaaggaa tatgttattg ctgtgtgacaa gcccatcacg ttatcctgtg aagcagatgg   12540
cctcctccg cctgacatta catggcataa agatgggcgt gcaattgtgg aatctatccg   12600
ccagcgcgtc ctcagctctg ctctctgca aatagcattt gtccagcctg tgatgctgg   12660
ccattacacg tgcatggcag ccaatgtagc aggatcaagc agcacaagca ccaagctcac   12720
cgtccatgta ccacccagga tcagaagtac agaaggacac tacacggtca atgagaattc   12780
acaagccatt cttccatgcg tagctgatgg aatccccaca ccagcaatta actggaaaaa   12840
agacaatgtt cttttagcta acttgttagg aaaatacact gctgaaccat atggagaact   12900
cattttagaa aatgttgtgc tggaggattc tggcttctat acctgtgttg ctaacaatgc   12960
tgcaggtgaa gatacacaca ctgtcagcct gactgtgcat gttctcccca ttttactga   13020
acttcctgga gacgtgtcat taaataaagg agaacagcta cgattaagct gtaaagctac   13080
tggtattcca ttgcccaaat taacatgaac cttcaataac aatattattc cagcccactt   13140
tgacagtgtg aatggacaca gtgaacttgt tattgaaaga gtgtcaaaag aggattcagg   13200
tacttatgtg tgcaccgcag agaacagcgt tggctttgtg aaggcaattg gatttgttta   13260
tgtgaaagaa cctccagtct tcaaaggtga ttatccttct aactggatt aaccacttgg   13320
tgggaatgca atcctgaatt gtgaggtgaa aggagacccc accccaacca tccagtggaa   13380
cagaaaggga gtggatattg aaattagcca cagaatccgg caactgggca atggctccct   13440
```

FIG. 7D

Homo sapiens fibulin 6 (FIBL-6), mRNA
gi|20536570|ref|XM_053531.6|[20536570]

| | | | | | |
|---|---|---|---|---|---|
| ggccatctat | ggcactgtta | atgaagatgc | cggtgactat | acatgtgtag | ctaccaatga | 13500 |
| agctggggtg | gtggagcgca | gcatgagtct | gactctgcaa | agtcctccta | ttatcactct | 13560 |
| tgagccagtg | gaaactgtta | ttaatgctgg | tggcaaaatc | atattgaatt | gtcaggcaac | 13620 |
| tggagagcct | caaccaacca | ttacatggtc | ccgtcaaggg | cactctattt | cctgggatga | 13680 |
| ccgggttaac | gtgttgtcca | acaactcatt | atatattgct | gatgctcaga | aagaagatac | 13740 |
| ctctgaattt | gaatgtgttg | ctcgaaactt | aatgggttct | gtccttgtca | gagtgccagt | 13800 |
| catagtccag | gttcatggtg | gatttcgca | gtggtctgca | tggagagcct | gcagtgtcac | 13860 |
| ctgtggaaaa | ggcatccaaa | agaggagtcg | tctgtgcaac | cagcccttc | cagccaatgg | 13920 |
| tgggaagccc | tgccaaggtt | cagatttgga | aatgcgaaac | tgtcaaaata | agccttgtcc | 13980 |
| agtggatggt | agctggtcgg | aatggagtct | ttgggaagaa | tgcacaagga | gctgtggacg | 14040 |
| cggcaaccaa | accaggacca | ggacttgcaa | taatccatca | gttcagcatg | gtgggcggcc | 14100 |
| atgtgaaggg | aatgctgtgg | aaataattat | gtgcaacatt | aggccttgcc | cagttcatgg | 14160 |
| agcatggagc | gcttggcagc | cttggggaac | atgcagcgaa | agttgtggga | aaggtactca | 14220 |
| gacaagagca | agactttgta | ataacccacc | accagcgttt | ggtgggtcct | actgtgatgg | 14280 |
| agcagaaaca | cagatgcaag | tttgcaatga | aagaaattgt | ccaattcatg | gcaagtgggc | 14340 |
| gacttgggcc | agttggagtg | cctgttctgt | gtcatgtgga | ggaggtgcca | gacagagaac | 14400 |
| aaggggctgc | tccgaccctg | tgcccagta | tggaggaagg | aaatgcgaag | ggagtgatgt | 14460 |
| ccagagtgat | ttttgcaaca | gtgacccttg | cccaacccat | ggtaactgga | gtccttggag | 14520 |
| tggctgggga | acatgcaagcc | ggacgtgtaa | cggagggcag | atgcggcggt | accgcacatg | 14580 |
| tgataaccct | cctcctcca | atgggggaag | agcttgtggg | ggaccagact | cccagatcca | 14640 |
| gaggtgcaac | actgacatgt | gtcctgtgga | tggaagttgg | ggaagctggc | atagttggag | 14700 |
| ccagtgctct | gcctcctgtg | gaggaggtga | aaagactcgg | aagcggctgt | gcgaccatcc | 14760 |
| tgtgccagtt | aaaggtggcc | gtccctgtcc | cggagacact | actcaggtga | ccaggtgcaa | 14820 |
| tgtacaagca | tgtccaggtg | ggcccagcg | agccagagga | agtgttattg | gaaatattaa | 14880 |
| tgatgttgaa | tttggaattg | ctttccttaa | tgccacaata | actgatagcc | ctaactctga | 14940 |
| tactagaata | atacgtgcca | aaattaccaa | tgtacctcgt | agtcttggtt | cagcaatgag | 15000 |
| aaagatagtt | tctattctaa | atcccattta | ttggacaaca | gcaaaggaaa | taggagaagc | 15060 |
| agtcaatggc | tttaccctca | ccaatgcagt | cttcaaaaga | gaaactcaag | tggaatttgc | 15120 |
| aactggagaa | atcttgcaga | tgagtcatat | tgcccgggc | ttggattccg | atggttcttt | 15180 |
| gctgctagat | atcgttgtga | gtggctatgt | cctacagctt | cagtcacctg | ctgaagtcac | 15240 |
| tgtaaaggat | tacacagagg | actacattca | aacaggtcct | gggcagctgt | acgcctactc | 15300 |
| aacccggctg | ttcaccattg | atggcatcag | catcccatac | acatggaacc | acaccgtttt | 15360 |
| ctatgatcag | gcacagggaa | gaatgccttt | cttggttgaa | acacttcatg | catcctctgt | 15420 |
| ggaatctgac | tataaccaga | tagaagagac | actgggtttt | aaaattcatg | cttcaatatc | 15480 |
| caaaggagat | cgcagtaatc | agtgcccctc | cgggtttacc | ttagactcag | ttggacccttt | 15540 |
| ttgtgctgat | gaggatgaat | gtgcagcagg | gaatccctgc | tcccatagct | gccacaatgc | 15600 |
| catgggggact | tactactgct | cctgccctaa | aggcctcacc | atagctgcag | atggaagaac | 15660 |
| ttgtcaagat | attgatgagt | gtgctttggg | taggcatacc | tgccacgctg | gtcaggactg | 15720 |
| tgacaatacg | attggatctt | atcgctgtgt | ggtccgttgt | ggaagtggct | ttcgaagaac | 15780 |
| ctctgatggg | ctgagttgtc | aagatattaa | tgaatgtcaa | gaatccagcc | cctgtcacca | 15840 |
| gcgctgtttc | aatgccatag | gaagtttcca | ttgtggatgt | gaacctgggt | atcagctcaa | 15900 |
| aggcagaaaa | tgcatggatg | tgaacgagtg | tagacaaaat | gtatgcagac | agatcagca | 15960 |
| ctgtaagaac | acccgtggtg | gctataagtg | cattgatctt | tgtccaaatg | gaatgaccaa | 16020 |
| ggcagaaaat | ggaacctgta | ttgatattga | tgaatgtaaa | gatgggaccc | atcagtgcag | 16080 |
| atataaccag | atatgtgaga | atacaagagg | cagctatcgt | tgtgtatgcc | caagaggtta | 16140 |
| tcggtctcaa | ggagttggaa | gaccctgcat | ggacattaat | gaatgtgaac | aagtgcctaa | 16200 |
| accttgtgca | catcagtgct | ccaacacccc | cggcagcttc | aagtgtatct | gtccaccagg | 16260 |
| acaacattta | ttaggggacg | ggaaatcttg | cgctggattg | gagaggctgc | caaattatgg | 16320 |
| cactcaatac | agtagctata | accttgcacg | gttctcccct | gtgagaaaca | actatcaacc | 16380 |
| tcaacagcat | tacagacagt | actcacatct | ctacagctcc | tactcagagt | atagaaacag | 16440 |
| cagaacatct | ctctccagga | ctagaaggac | tattaggaaa | acttgccctg | aaggctctga | 16500 |
| ggcaagccat | gacacatgtg | tagatattga | tgaatgtgaa | aatacagatg | cctgccagca | 16560 |
| tgagtgtaag | aataccttg | gaagttatca | gtgcatctgc | ccacctggct | atcaactcac | 16620 |
| acacaatgga | aagacatgcc | aagatatcga | tgaatgtctg | gagcagaatg | tgcactgtgg | 16680 |
| acccaatcgc | atgtgcttca | acatgagagg | aagctaccag | tgcatcgata | caccctgtcc | 16740 |
| acccaactac | caacgggatc | ctgtttcagg | gttctgcctc | aagaactgtc | cacccaatga | 16800 |
| tttggaatgt | gccttgagcc | catatgcctt | ggaatacaaa | ctcgtctccc | tcccatttgg | 16860 |

FIG. 7E

Homo sapiens fibulin 6 (FIBL-6), mRNA
gi|20536570|ref|XM_053531.6|[20536570]

```
aatagccacc aatcaagatt taatccggct ggttgcatac acacaggatg gagtgatgca    16920
tcccaggaca acttcctca tggtagatga ggaacagact gttcctttg ccttgaggga     16980
tgaaaacctg aaaggagtgg tgtatacaac acgaccacta cgagaagcag agacctaccg    17040
catgagggtc cgagcctcat cctacagtgc caatgggacc attgaatatc agaccacatt    17100
catagtttat atagctgtgt ccgcctatcc atactaagga actctccaaa gcctattcca    17160
catatttaaa ccgcattaat catggcaatc aagccccctt ccagattact gtctcttgaa    17220
cagttgcaat cttggcagct tgaaaatggt gctacactct gttttgtgtg ccttccttgg    17280
tacttctgag gtattttcat gatcccacca tggtcatatc ttgaagtatg gtctagaaaa    17340
gtccccttatt atttattta ttacactgga gcagttactt cccaaagatt attctgaaca    17400
tctaacagga catatcagtg atggtttaca gtagtgtagt acctaagatc atttcctga    17460
aagccaaacc aaacaacgaa aaacaagaac aactaattca gaatcaaata gagttttga    17520
gcatttgact atttttagaa tcataaaatt agttactaag tattttgatc aaagcttata    17580
aataactta cggagatttt tgtaagtatt gatacattat aataggactt gcctattttc    17640
attttaaga agaaaaacac cactcatttt atataatata gtacagctac tataaggctt    17700
gtttgatccc aaatggtgct tatcttgatt gaacattcag aacaaggata ttattttcag    17760
tgatttgtg agatcagctg aaccacttat gataataata ataaaaaaga ctgctttgcc    17820
ctcacgtcag ttgtacatgg catggaactt taaaaatttt aatataaact ttcatccagt    17880
tagcttcata acttttacgt tccagaattt tgtttatttt cctgtcaatg aaagcaattt    17940
ttaaagatac cagtgggaca gatttggttt tttaaaaatc tcatgtgttc aaattaacat    18000
aaatattaca cgtcaataca ctgtacatgg tggtaataga ctctaagcaa ttgccaagat    18060
gtattctatt tttatgaagt gtatatatat taccttagtg tgcatttct atataatatc     18120
ttgatggact cttttataaa attattttat aaaaaacaat gttacactaa aatcagccta    18180
aataaatttt cacaacttt tttcat                                          18206
```

FIG. 7F

Homo sapiens fibulin 6 (FIBL-6), protein sequence
(5,635 amino acids)

```
MISWEVVHTVFLFALLYSSLAQDASPQSEIRAEEIPEGASTLAFVFDVTGSMYDDLVQVIEGASKILETSLKRPKRP
LFNFALVPFHDPEIGPVTITTDPKKFQYELRELYVQGGGDCPEMSIGAIKIALEISLPGSFIYVFTDARSKDYRLTH
EVLQLIQQKQSQVVFVLTGDCDDRTHIGYKVYEEIASTSSGQVFHLDKKQVNEVLKWVEEAVQASKVHLLSTDHLEQ
AVNTWRIPFDPSLKEVTVSLSGPSPMIEIRNPLGKLIKKGFGLHELLNIHNSAKVVNVKEPEAGMWTVKTSSSGRHS
VRITGLSTIDFRAGFSRKPTLDFKKTVSRPVQGIPTYVLLNTSGISTPARIDLLELLSISGSSLKTIPVKYYPHRKP
YGIWNISDFVPPNEAFFLKVTGYDKDDYLFQRVSSVSFSSIVPDAPKVTMPEKTPGYYLQPGQIPCSVDSLLPFTLS
FVRNGVTLGVDQYLKESASVNLDIAKVTLSDEGFYECIAVSSAGTGRAQTFFDVSEPPPVIQVPNNVTVTPGERAVL
TCLIISAVDYNLTWQRNDRDVRLAEPARIRTLANLSLELKSVKFNDAGEYHCMVSSEGGSSAASVFLTVQEPPKVTV
MPKNQSFTGGSEVSIMCSATGYPKPKIAWTVNDMFIVGSHRYRMTSDGTLFIKNAAPKDAGIYGCLASNSAGTDKQN
STLRYIEAPKLMVVQSELLVALGDITVMECKTSGIPPPQVKWFKGDLELRPSTFLIIDPLLGLLKIQETQDLDAGDY
TCVAINEAGRATGKITLDVGSPPVFIQEPADVSMEIGSNVTLPCYVQGYPEPTIKWRRLDNMPIFSRPFSVSSISQL
RTGALFILNLWASDKGTYICEAENQFGKIQSETTVTVTGLVAPLIGISPSVANVIEGQQLTLPCTLLAGNPIPERRW
IKNSAMLLQNPYITVRSDGSLHIERVQLQDGGEYTCVASNVAGTNNKTTSVVVHVLPTIQRGQQILSTIEGIPVTLP
CKASGNPKPSVIWSKKGELISTSSAKFSAGADGSLYVVSPGGEESGEYVCTATNTAGYAKRKVQLTVYVRPRVFGDQ
RGLSQDKPVEISVLAGEEVTLPCEVKSLPPPIITWAKETQLISPFSPRHTFLPSGSMKITETRTSDSGMYLCVATNI
AGNVTQAVKLNVHVPPKIQRGPKHLKVQVGQRVDIPCNAQGTPLPVITWSKGGSTMLVDGEHHVSNPDGTLSIDQAT
PSDAGIYTCVATNIAGTDETEITLHVQEPPTVEDLEPPYNTTFQERVANQRIEFPCPAKGTPKPTIKWLHNGRELTG
REPGISILEDGTLLVIASVTPYDNGEYICVAVNEAGTTERKYNLKVHVPPVIKDKEQVTNVSVLLNQLTNLFCEVEG
TPSPIIMWYKDNVQVTESSTIQTVNNGKILKLFRATPEDAGRYSCKAINIAGTSQKYFNIDVLVPPTIIGTNFPNEV
SVVLNRDVALECQVKGTPFPDIHWFKDGKPLFLGDPNVELLDRGQVLHLKNARRNDKGRYQCTVSNAAGKQAKDIKL
TIYNPPSIKGGNVTTDISVLINSLIKLECETRGLPMPAITWYKDGQPIMSSSQALYIDKGQYLHIPRAQVSDSATYT
CHVANVAGTAEKSFHVDVYVPPMIEGNLATPLNKQVVIAHSLTLECKAAGNPSPILTWLKDGVPVKANDNIRIEAGG
KKLEIMSAQEIDRGQYICVATSVAGEKEIKYEVDVLVPPAIEGGDETSYFIVMVNNLLELDCHVTGSPPPTIMWLKD
GQLIDERDGFKILLNGRKLVIAQAQVSNTGLYRCMAANTAGDHKKEFEVTVHVPPTIKSSGLSERVVVKYKPVALQC
IANGIPNPSITWLKDDQPVNTAQGNLKIQSSGRVLQIAKTLLEDAGRYTCVATNAAGETQQHIQLHVHEPPSLEDAG
KMLNETVLVSNPVQLECKAAGNPVPVITWYKDNRLLSGSTSMTFLNRGQIIDIESAQISDAGIYKCVAINSAGATEL
FYSLQVHVAPSISGSNNMVAVVVNNPVRLECEARGIPAPSLTWLKDGSPVVSSFSNGLQVLSGGRILALTSAQISDTG
RYTCVAVNAAGEKQRDIDLRVYVPPNIMGEEQNVSVLISQAVELLCQSDAIPPPTLTWLKDGHPLLKKPGLSISENR
SVLKIEDAQVQDTGRYTCEATNVAGKTEKNYNVNIWVPPNIGGSDELTQLTVIEGNLISLLCESSGIPPPNLIWKKK
GSPVLTDSMGRVRILSGGRQLQISIAEKSDAALYSCVASNVAGTAKKEYNLQVYIRPTITNSGSHPTEIIVTRGKSI
SLECEVQGIPPPTVTWMKDGHPLIKAKGVEILDEGHILQLKNIHVSDTGRYVCVAVNVAGMTDKKYDLSVHAPPSII
GNHRSPENISVVEKNSVSLTCEASGIPLPSITWFKDGWPVSLSNSVRILSGGRMLRLMQTTMEDAGQYTCVVRNAAG
EERKIFGLSVLVPPHIVGENTLEDVKVKEKQSVTLTCEVTGNPVPEITWHKDGQPLQEDEAHHIISGGRFLQITNVQ
VPHTGRYTCLASSPAGHKSRSFSLNVFVSPTIAGVGSDGNPEDVTVILNSPTSLVCEAYSYPPATITWFKDGTPLES
NRNIRILPCGRTLQILNAQEDNAGRYSCVATNEAGEMIKHYEVKVYIPPIINKGDLWGPGLSPKEVKIKVNNTLTLE
CEAYAIPSASLSWYKDGQPLKSDDHVNIAANGHTLQIKEAQISDTGRYTCVASNIAGEDELDFDVNIQVPPSFQKLW
EIGNMLDTGRNGEAKDVIINNPISLYCETNAAPPPTLTWYKDGHPLTSSDKVLILPGGRVLQIPRAKVEDAGRYTCV
AVNEAGEDSLQYDVRVLVPPIIKGANSDLPEEVTVLVNKSALIECLSSGSPAPRNSWQKDGQPLLEDDHHKFLSNGR
ILQILNTQITDIGRYVCVAENTAGSAKKYFNLNVHVPPSVIGPKSENLTVVVNNFISLTCEVSGFPPPDLSWLKNEQ
PIKLNTNTLIVPGGRTLQIIRAKVSDGGEYTCIAINQAGESKKKFSLTVYVPPSIKDHDSESLSVVNVREGTSVSLE
CESNAVPPPVITWYKNGRMITESTHVEILADGQMLHIKKAEVSDTGQYVCRAINVAGRDDKNFHLNVYVPPSIEGPE
REVIVETISNPVTLTCDATGIPPPTIAWLKNHKRIENSDSLEVRILSGGSKLQIARSQHSDSGNYTCIASNMEGKAQ
KYYFLSIQVPPSVAGAEIPSDVSVLLGENVELVCNANGIPTPLIQWLKDGKPIASGETERIRVSANGSTLNIYGALT
SDTGKYTCVATNPAGEEDRIFNLNVYVTPTIRGNKDEAEKLMTLVDTSINIECRATGTPPPQINWLKNGLPLPLSSH
IRLLAAGQVIRIVRAQVSDVAVYTCVASNRAGVDNKHYNLQVFAPPNMDNSMGTEEITVLKGSSTSMACITDGTPAP
SMAWLRDGQPLGLDAHLTVSTHGMVLQLLKAETEDSGKYTCIASNEAGEVSKHFILKVLEPPHINGSEEHEEISVIV
NNPLELTCIASGIPAFKMTWMKDGRPLPQTDQVQTLGGGEVLRISTAQVEDTGRYTCLASSPAGDDDKEYLVRVHVP
PNIAGTDEPRDITVLRNRQVTLECKSDAVPPPVITWLRNGERLQATPRVRILSGGRYLQINNADLGDTANYTCVASN
IAGKTTREFILTVNVPPNIKGGPQSLVILLNKSTVLECIAEGVPTPRITWRKDGAVLAGNHARYSILENGFLHIQSA
HVTDTGRYLCMATNAAGTDRRRIDLQVHVPPSIAPGPTNMTVIVNVQTTLACEATGIPKPSINWRKNGHLLNVDQNQ
NSYRLLSSGSLVIISPSVDDTATYECTVTNGAGDDKRTVDLTVQVPPSIADEPTDFLVTKHAPAVITCTASGVPFPS
IHWTKNGIRLLPRGDGYRILSSGAIEILATQLNHAGRYTCVARNAAGSAHRHVTLHVHEPPVIQPQPSELHVILNNP
```

FIG. 8A

Homo sapiens fibulin 6 (FIBL-6), protein sequence
(5,635 amino acids)

ILLPCEATGTPSPFITWQKEGINVNTSGRNHAVLPSGGLQISRAVREDAGTYMCVAQNPAGTALGKIKLNVQVPPVI
SPHLKEYVIAVDKPITLSCEADGLPPPDITWHKDGRAIVESIRQRVLSSGSLQIAFVQPGDAGHYTCMAANVAGSSS
TSTKLTVHVPPRIRSTEGHYTVNENSQAILPCVADGIPTPAINWKKDNVLLANLLGKYTAEPYGELILENVVLEDSG
FYTCVANNAAGEDTHTVSLTVHVLPTFTELPGDVSLNKGEQLRLSCKATGIPLPKLTWTFNNNIIPAHFDSVNGHSE
LVIERVSKEDSGTYVCTAENSVGFVKAIGFVYVKEPPVFKGDYPSNWIEPLGGNAILNCEVKGDPTPTIQWNRKGVD
IEISHRIRQLGNGSLAIYGTVNEDAGDYTCVATNEAGVVERSMSLTLQSPPIITLEPVETVINAGGKIILNCQATGE
PQPTITWSRQGHSISWDDRVNVLSNNSLYIADAQKEDTSEFECVARNLMGSVLVRVPVIVQVHGGFSQWSAWRACSV
TCGKGIQKRSRLCNQPLPANGGKPCQGSDLEMRNCQNKPCPVDGSWSEWSLWEECTRSCGRGNQTRTRTCNNPSVQH
GGRPCEGNAVEIIMCNIRPCPVHGAWSAWQPWGTCSESCGKGTQTRARLCNNPPPAFGGSYCDGAETQMQVCNERNC
PIHGKWATWASWSACSVSCGGGARQRTRGCSDPVPQYGGRKCEGSDVQSDFCNSDPCPTHGNWSPWSGWGTCSRTCN
GGQMRRYRTCDNPPPSNGGRACGGPDSQIQRCNTDMCPVDGSWGSWHSWSQCSASCGGGEKTRKRLCDHPVPVKGGR
PCPGDTTQVTRCNVQACPGGPQRARGSVIGNINDVEFGIAFLNATITDSPNSDTRIIRAKITNVPRSLGSAMRKIVS
ILNPIYWTTAKEIGEAVNGFTLTNAVFKRETQVEFATGEILQMSHIARGLDSDGSLLLDIVVSGYVLQLQSPAEVTV
KDYTEDYIQTGPGQLYAYSTRLFTIDGISIPYTWNHTVFYDQAQGRMPFLVETLHASSVESDYNQIEETLGFKIHAS
ISKGDRSNQCPSGFTLDSVGPFCADEDECAAGNPCSHSCHNAMGTYYCSCPKGLTIAADGRTCQDIDECALGRHTCH
AGQDCDNTIGSYRCVVRCGSGFRRTSDGLSCQDINECQESSPCHQRCFNAIGSFHCGCEPGYQLKGRKCMDVNECRQ
NVCRPDQHCKNTRGGYKCIDLCPNGMTKAENGTCIDIDECKDGTHQCRYNQICENTRGSYRCVCPRGYRSQGVGRPC
MDINECEQVPKPCAHQCSNTPGSFKCICPPGQHLLGDGKSCAGLERLPNYGTQYSSYNLARFSPVRNNYQPQQHYRQ
YSHLYSSYSEYRNSRTSLSRTRRTIRKTCPEGSEASHDTCVDIDECENTDACQHECKNTFGSYQCICPPGYQLTHNG
KTCQDIDECLEQNVHCGPNRMCFNMRGSYQCIDTPCPPNYQRDPVSGFCLKNCPPNDLECALSPYALEYKLVSLPFG
IATNQDLIRLVAYTQDGVMHPRTTFLMVDEEQTVPFALRDENLKGVVYTTRPLREAETYRMRVRASSYSANGTIEYQ
TTFIVYIAVSAYPY

FIG. 8B

GENE MUTATION ASSOCIATED WITH AGE-RELATED MACULAR DEGENERATION

CROSS REFERENCE TO RELATED APPLICATION

This Application claims the benefit of Provisional U.S. Patent Application No. 60/443,214, filed Jan. 27, 2003.

FIELD OF THE INVENTION

The present invention relates generally to the field of age-related macular degeneration (AMD). More particularly, the invention is concerned with the identification of a gene which, when mutated, is associated with AMD, as well as the transcripts, gene products and associated sequence information. The present invention also relates to methods for diagnosing and detecting carriers of the gene, and to AMD diagnosis and gene therapy using the information derived from the DNA, protein, and function of the protein.

BACKGROUND OF THE INVENTION

AMD involves a loss of central vision as a result of a progressive degeneration of retinal and underlying tissues in people over the age of 50 years. Specific causes of significant loss in AMD are atrophy of the retina and the retinal pigment epithelium, and/or the growth of neovascularization with subsequent subretinal scarring. It is the main cause of irreversible blindness in the United States and Europe, and the prevalence appears to be increasing. Increasing rates are also being documented in Asia (Koh, A. H. C., et al., Ann. Acad. Med. 31:399-404, 2002). AMD accounts for about 50% of all cases of registered blindness in the west. Approximately 2 million Americans suffer vision loss from AMD, and over 10 million Americans show some early signs of AMD. The incidence of significant vision loss associated with AMD is about 2% for those at age 70, and 6% for those at age 80. (Hawkins, B. S., et al., Mol. Vis. 5:26, 1999; Vingerling, J. R., et al. Epidemiol. Rev. 17:347-360, 1995.) The total number of people with AMD is expected to triple by the year 2030. (Vinding, T., Acta Ophthalmologica 73 (Suppl): 1-32, 1995.)

Current methods of treatment have achieved only limited efficacy, and are ineffective if not started at a relatively early stage of the disease. Thus, there is a critical need in the art for methods of detecting AMD at a stage early enough to permit therapeutic treatment to prevent loss of vision, and to ultimately prevent development of the disease.

BRIEF DESCRIPTION OF THE FIGURES

FIG. 7. FIG. 7 shows the polynucleotide sequences of human fibulin 6 mRNA, accession no. XM_053531.6, also as shown in SEQ ID NO:1.

FIG. 8. FIG. 8 shows the amino acid sequence of human fibulin 6, also shown as SEQ ID NO:2.

DETAILED DESCRIPTION OF THE INVENTION

Figure 1:
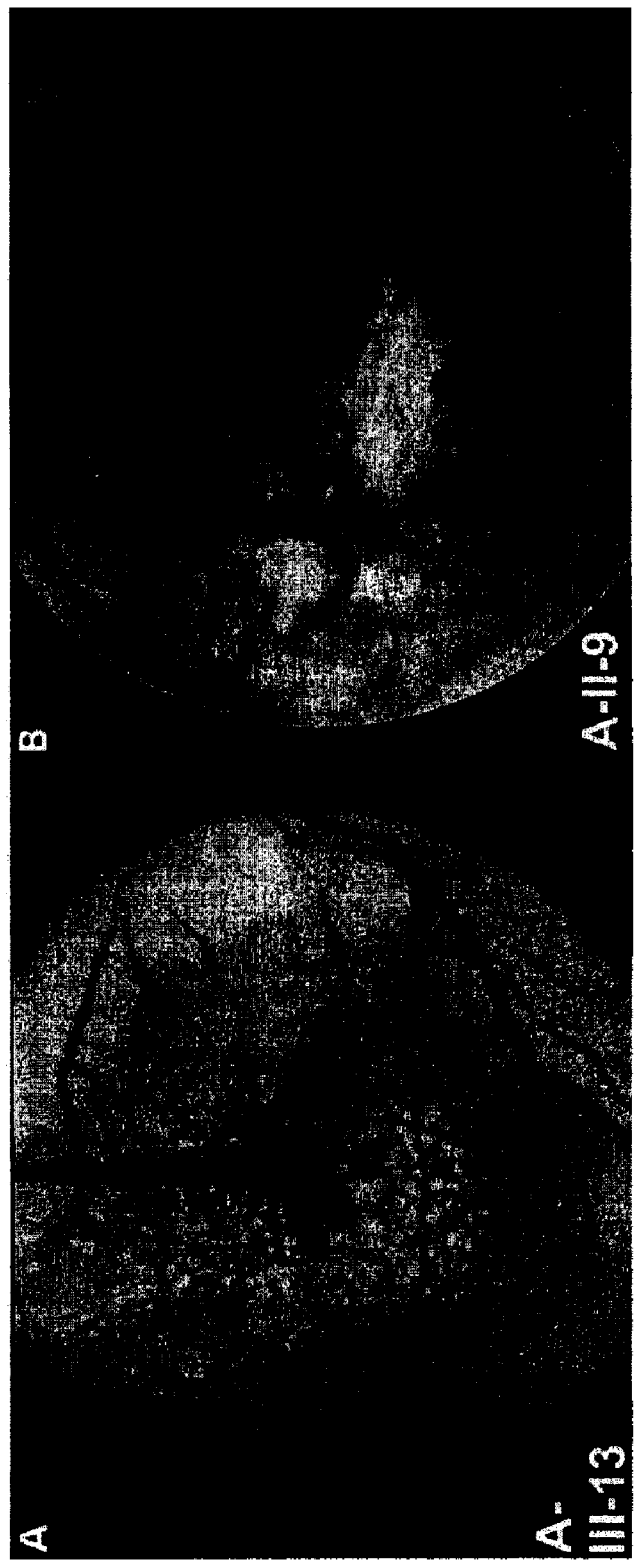
FIG. 1. Fundus photographs of representative affected members of family A. Panel A. Right eye of 54-year old individual (III-13) with extensive large drusen. Panel B. Left eye of 87-year old individual (II-9) with geographic atrophy and drusen.

Age-related macular degeneration (AMD) is a major cause of blindness in the United States and other industrialized nations. (Evans J, Wormald R., *British Journal Ophthalmology* 80:9-14, 1996; Klein R, Klein B E K, Linton K L P, *Ophthalmology* 99:933-943, 1992; Vingerling J R, *Ophthalmology* 102:205-210, 1995). Early AMD is characterized clinically by drusen, which are extracellular deposits of proteins, lipids, and cellular debris, (Hageman G S, Mullins R F, *Mol Vis* 5:28, 1999), that are located beneath the retinal pigment epithelium (RPE). The RPE provides nutritional, metabolic, and phagocytic functions for the overlying photoreceptors. Significant vision loss results from dysfunction or death of photoreceptors in the macula in association with late stages of AMD (geographic atrophy of the RPE and subretinal neovascularization). The late onset of AMD and its apparent complex genetics have hindered mapping and identification of genes that cause this disease. (Gorin M B, *Mol Vis* 5:29, 1999.)

Although several forms of therapy are available, most patients with AMD continue to lose vision in spite of treatment. Laser photocoagulation has been used for over three decades, but is of limited value in only a comparatively small proportion of cases. In the past three years, photodynamic therapy has been used to treat a somewhat larger proportion of AMD cases. However, the benefits are limited primarily to slowing the progression of the disease. Currently, pharmacologic therapy is being actively investigated. Several anti-angiogenic drugs are being evaluated in ongoing clinical trials, with no definitive results at this time. Radiation therapy has not been shown to be of benefit, and a number of surgical approaches are also under investigation, but with no conclusive benefits shown.

Because of the lack of suitable and successful treatment options, early diagnosis and prevention are goals in current AMD research. One recently completed large study demonstrated that treatment of certain patients with "high risk" AMD using antioxidants and zinc led to a statistically significant reduction in the occurrence of moderate visual loss. Disease progression was also reduced by approximately 25% in these patients. Thus, there is some indication that non-surgical intervention can be helpful in at least slowing the progression of the disease.

It is preferable to slow or cease the progress of the disease at a stage where the patient has minimal loss of vision. This involves the need for methods of early detection, so that a treatment regimen, such as anti-oxidant therapy, can be initiated. While it had been believed that AMD was an acquired disease, more recent evidence shows a clear hereditary element in at least some forms of the disease. In these involved families, as treatment regimens improve, early intervention will be very important.

A mutation in EGF-containing fibrillin-like extracellular matrix protein 1 (EFEMP1) was identified and reported by Stone, E. M., et al., Nature Genetics 22:199-202, 1999. The mutation is associated with Malattia Leventinese (ML) and Doyne honeycomb retinal dystrophy (DHRD), both of which are autosomal dominant diseases characterized by drusen deposits that accumulate beneath the retinal pigment epithelium. Stone et al. identified a single non-conservative mutation, in which arginine is replaced by tryptophan at position 345. The mutation was found in all families studied who exhibited the ML/DHRD phenotype. The mutation was not found in 477 control individuals or in 494 patients with age-related macular degeneration. This research in part set a precedent for the proposition that a single mutation could be closely associated with phenotype in a disease with clinical symptoms similar to those of macular degeneration, particularly the accumulation of drusen. Another useful clue from this work was the discovery of the mutation.

The present inventors previously identified a large family affected by AMD, and found linkage of the defect to chromosome 1q. Klein, M. L., et al., "Age-Related Macular Degeneration. Clinical Features in a Large Family and Linkage to Chromosome 1q," Arch. Ophthalmol. 116:1082-1088, 1998. In this large family, transmission of AMD trait is consistent with autosomal-dominant inheritance. The average age at diagnosis of AMD was 65 years, and the earliest age of onset of symptoms was 52 years. In two family members, the disease haplotype was found but the individuals did not exhibit the phenotype, possibly because of their ages, 44 and 48, which were below the earliest age of onset for the individuals exhibiting the disease. Diagnosis was performed using the established Wisconsin Age-Related Maculopathy Grading System, as described in Klein, R., et al., Ophthalmology 104:7-21, 1997.

Figure 4:
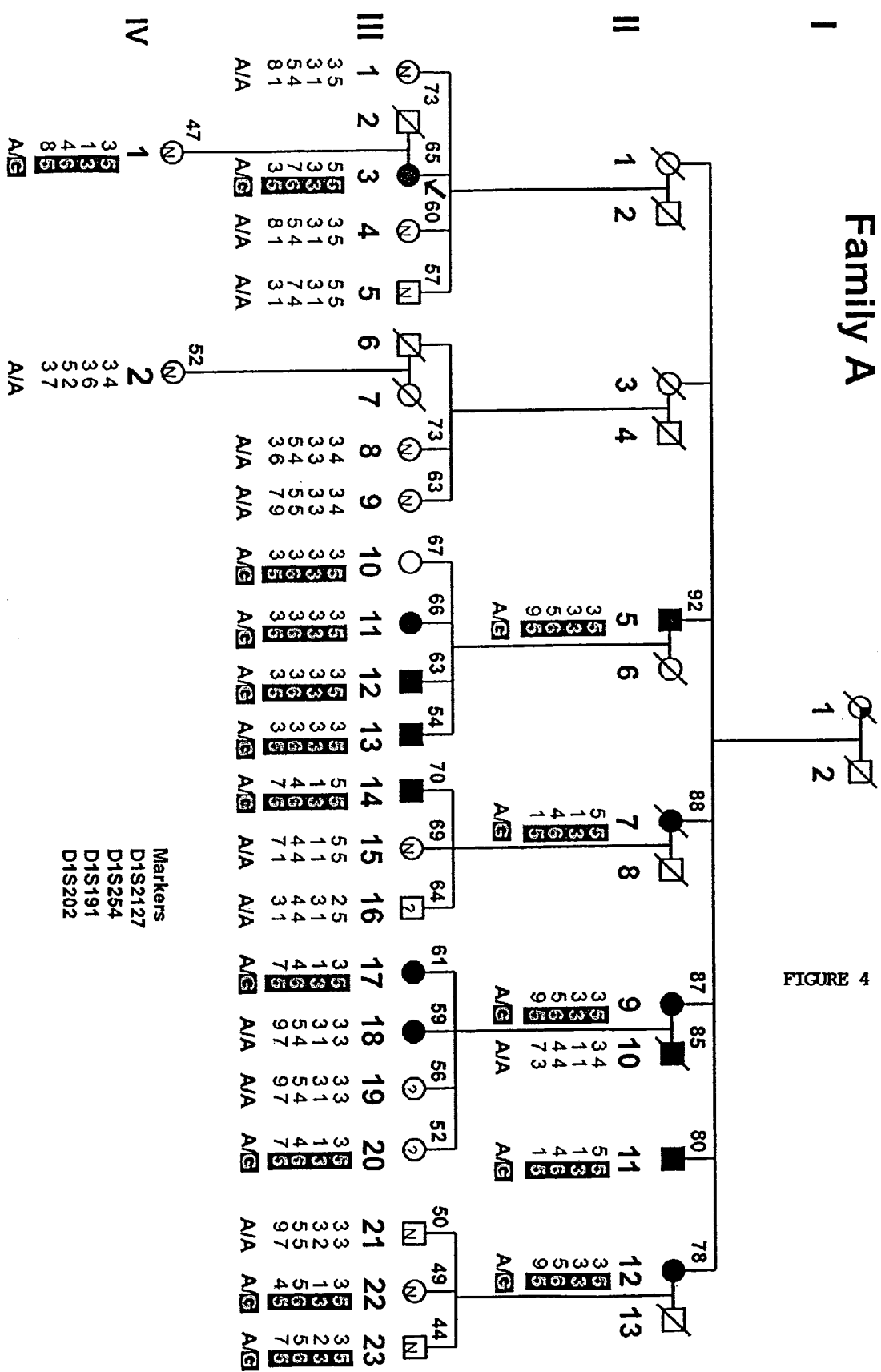
FIG. 4. Family A pedigree showing that the Gln5345Arg variation segregates exclusively with the disease haplotype. Disease haplotype and Gln5345Arg variation are boxed. Squares denote males; circles, females; slashed symbol, deceased; filled, affected; N, normal; ?, uncertain; open, undiagnosed; quarter-filled, suspected affected; and arrow, proband. The smaller numbers above the gender symbols indicate age at death or diagnosis. The marker D1S2127 is about 965 kb proximal to FIBL-6, D1S254 and D1S191 are within FIBL-6, and D1S202 is about 806 kb distal to FIBL-6.

These early studies of the family led to the conclusion that the disease-causing gene for AMD in this family was located between markers D1S466 and D1S413 (FIG. 4). Klein M L, Arch Ophthalmol 116:1082-8, 1998. Identification of this region led the inventors to consider the possibility of a mutation as a causative factor in the inherited form of AMD in this large family. The inventors screened 27 genes from this region for sequence variations that segregate with the disease haplotype in this family.

Figure 2:
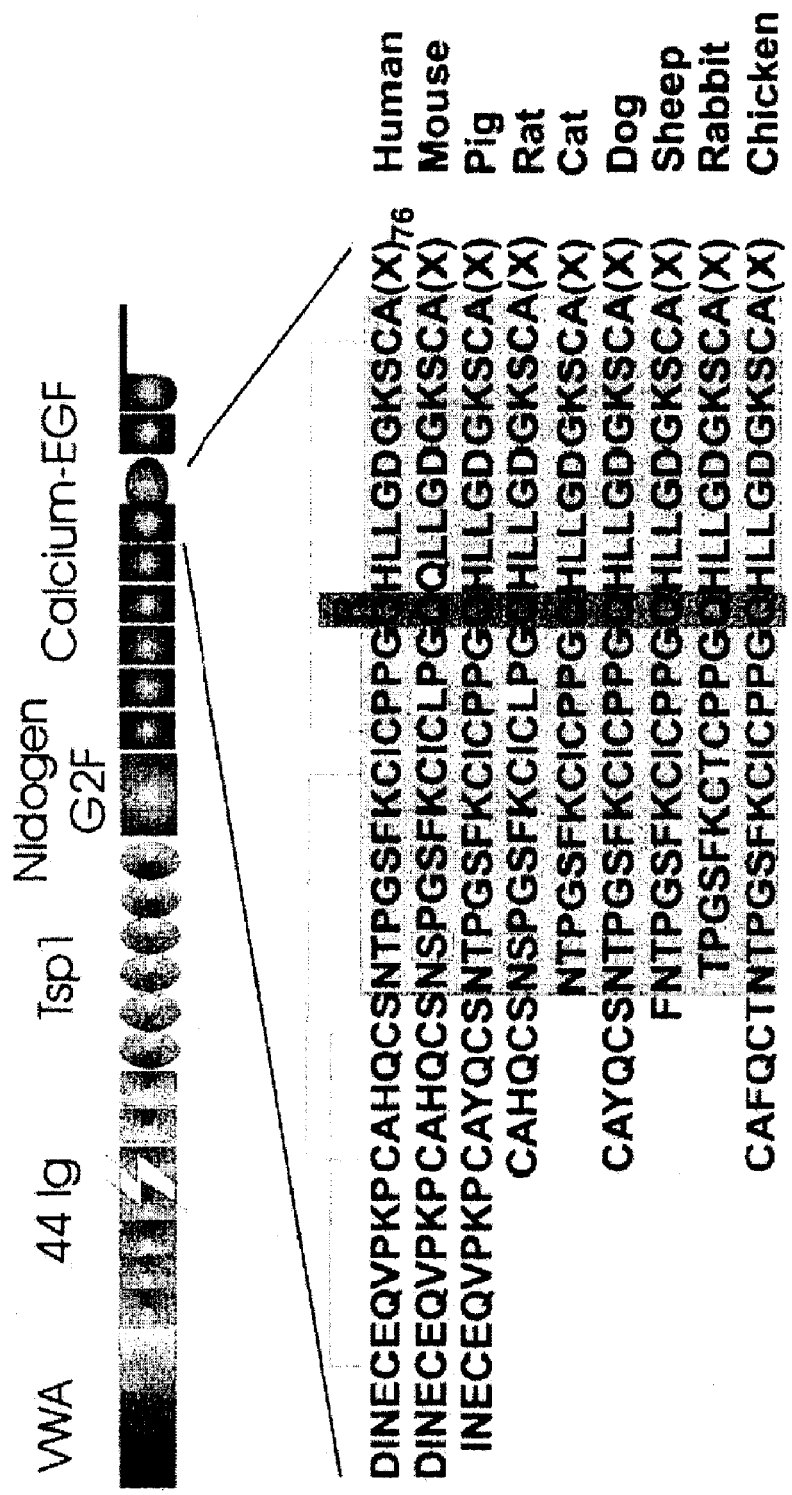
FIG. 2. Depiction of the domain structure of FIBL-6 and conservation of Gln5345. The amino acid sequence of a portion of exon 104 in human, 7 additional mammalian species, and chicken is provided.

According to the invention, FIBULIN-6 (FIBL-6) was screened because of its resemblance to EFEMP1. The protein sequence of FIBL-6 is similar to that of previously identified hemicentin in Caenorhabditis elegans. (Carpten J D, Genomics 64:1-14, 2000; Vogel B E, Hedgecock E M. Development 128:883-94, 2001; Hubbard T, Nucleic Acids Res 30:38-41, 2002.) FJBL-6 maps to 1q25.3-1q31.1, and extends over 450 kb of genomic DNA. Pairwise alignment of the FIBL-6 mRNA with genomic sequence delineated 107 exons that encode a 5,635 amino acid protein with a calculated molecular weight over 600 kDa. The predicted protein consists of an N-terminal von Willebrand factor type A domain, 44 tandem immunoglobulin modules, 6 thrombospondin type 1 domains, a G2 nidogen domain, 7 calcium binding epidermal growth factor-like (cbEGF) domains, and 1 EGF-like domain (FIG. 2).

FIBL-6 was considered to be an excellent candidate for the ARMD1 gene because its encoded protein contains a series of predicted cbEGF domains followed by a single EGF-like domain at its carboxy terminus similar to EFEMP1. This final EGF-like domain of EFEMP1 harbors the mutation associated with Mallatia Leventinese, Stone E M, Nat Genet 22:199-202, 1999, an earlier onset macular dystrophy characterized by drusen similar to those seen with AMD.

As a result of these analyses, a sequence variation was identified in exon 104 of the FIBL-6 gene, which produces a change from Gln to Arg at position 5345. This variation segregated with the disease haplotype in the family discussed above that had been linked to 1q25-31. This change was also detected in some affected members of three other AMD families, two unaffected members, one sporadic AMD case, and two control subjects. Individuals with the variation may appear normal due to their relatively young age or other phenotypic determinants. Gln5345 of FIBL-6 is conserved among eight species analyzed. RT-PCR analysis demonstrated FIBL-6 mRNA in human skin fibroblasts and retinal pigment epithelium (RPE) cells, as well as porcine trabecular meshwork cells, sclera, and retina. Two transcripts were identified, one with exon 104 and one without. The evidence of segregation, similarity to EFEMP1 and protein conservation, taken together, support the conclusion that the Gln5345Arg variation in FIBL-6 is the mutation responsible for AMD in this large family, which maps to 1q25-31.

Stone et al reported that a single non-conservative mutation, Arg345Trp, in the gene EFEMP1 was identified in families of individuals afflicted with Malattia Leventinese and Doyne honeycomb retinal dystrophy. These diseases appear earlier than does AMD. EFEMP1 refers to EGF-containing fibrillin-like extracellular matrix protein 1. (Nature Genetics 22:199-202, 1999.) The mutation identified in the present AMD family affects a protein of the FIBL-6 family. A human ortholog of hemicentin, which had been studied in nematodes (Vogel, B. E., et al., Development 128:883-894, 2001), was identified in chromosome 1q24-25 (Carpten, J. D., et al., Genomics 64:1014, 2000). FIBL-6 is an extracellular protein that, studies suggest, plays a role in ordering epithelial cells and in intracellular connections.

Vogel et al. found that mutations in FIBL-4 in nematodes is associated with a syndrome of tissue fragility, defective cell migration, among other effects.

Overall, the disclosed evidence provides strong support that FIBL-6 is the ARMD1 gene. The Gln5345Arg variation segregates exclusively with the ARMD1 disease haplotype in the 27-member family A. Of the 146 variations in 27 genes screened by the inventors to date, Gln5345Arg is the only variation with this property. No other changes in FIBL-6 were detected in the proband from family A. The Gln5345Arg variation appears to have a common founder among all four families and the three separate individuals studied. The glutamine at position 5345 in human FIBL-6 is strictly conserved among the 8 species analyzed. The glutamine to arginine variation changes both the size and the charge of the amino acid side chain, thus protein structure and function are likely to be affected.

FIBL-6 was a likely candidate for the ARMD1 gene because of its extensive similarity to EFEMP1. Both of these fibulin family genes encode an extracellular matrix protein that has a series of cbEGF domains followed by a single EGF-like domain at the carboxy terminus. Also, analogous to the Arg345Trp mutation in EFEMP1, which causes Mallatia Leventinese and Doyne honeycomb retinal dystrophy, there may be only a single FIBL-6 variant associated with AMD that has been inherited from a common founder. However, in contrast to EFEMP1, there may be additional environmental and genetic factors that determine the phenotypic expression of AMD.

In family A, only family members with the disease haplotype carry the Gln5345Arg mutation. One family member (III-18), who carries neither the disease haplotype nor the sequence variation, was diagnosed with AMD. However, both her mother (II-9), who is a family member, and her father (II-10) were diagnosed with AMD. Since AMD is considered a prevalent, Klein R, Klein B E K, Linton K L P, *Ophthalmology* 99:933-943, 1992, and complex heterogeneous disorder, Gorin M B, *Mol Vis* 5:29, 1999; Evans K, Bird A C, *British Journal of Ophthalmology* 80:763-768, 1996; Stone E M, Sheffield V C, Hageman G S, *Hum Mol Genet* 10:2285-92, 2001; Yates J R, Moore A T, *J Med Genet* 37:83-87, 2000, the father (II-10) and daughter's (III-18) AMD may be due to another gene. Of the four remaining family members who were not diagnosed with AMD but carry the Gln5345Arg change, one was not available for examination, and three, who were under 50 years of age, were likely too young to exhibit AMD.

The Gln5345Arg variation was also found in three additional AMD families, in which the variation does not segregate with AMD, and two control subjects. However, all deviations from a Mendelian pattern of inheritance can be explained by complex genetics, which are thought to be associated with AMD (Klein R, Klein B E K, Linton K L P, *Ophthalmology* 99:933-943, 1992), and complex heterogeneous disorder (Gorin M B, *Mol Vis* 5:29, 1999; Evans K, Bird A C, *British Journal of Ophthalmology* 80:763-768, 1996; Stone E M, Sheffield V C, Hageman G S, *Hum Mol Genet* 10:2285-92, 2001; Yates J R, Moore A T, *J Med Genet* 37:83-87, 2000). In particular, in all three nuclear families where the variation is found, both parents may carry genes that lead to AMD. Consistent with this notion, the frequency of AMD in these nuclear families is higher than 50% (i.e., 9 of 11 children ascertained have AMD). The two control subjects and the one unaffected member of family B may be either too young to exhibit signs of AMD, contain compensating changes within FIBL-6, lack other phenotypic determinants for AMD, or harbor genes that protect them from AMD.

Figure 5:
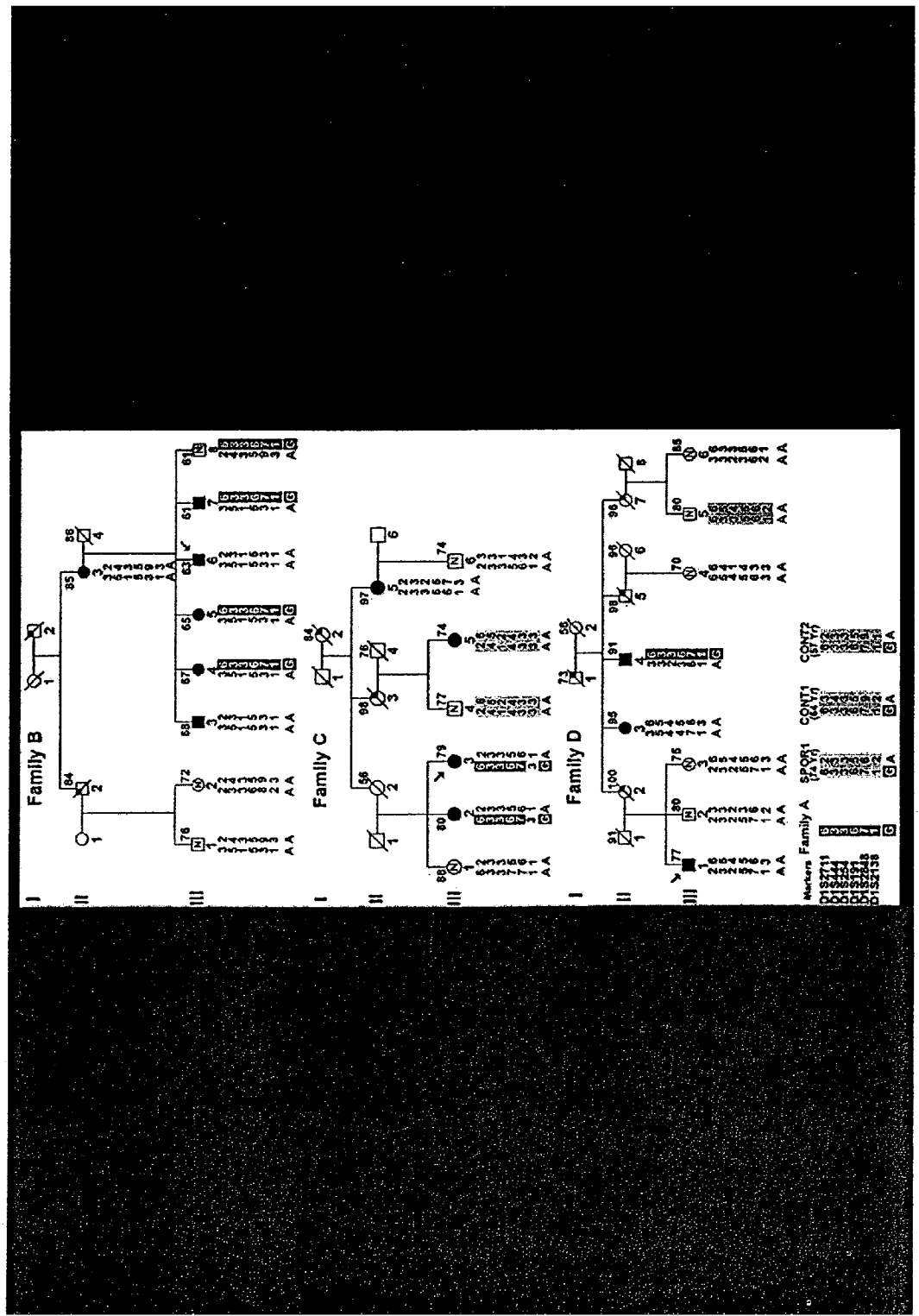
FIG. 5. Evidence of a common founder. Pedigrees of families B, C, and D show an association of the Gln5345Arg variation with a unique haplotype also found in family A. Family A disease haplotype and genotypes of the sporadic case and two control subjects with the variation are displayed at the bottom. The unique haplotype and Gln5345Arg variation are boxed (dark shading). Genotypes that cannot be assigned to haplotypes are boxed (light shading). Squares denote males; circles, females; slashed symbol, deceased; filled, affected; N, normal; ?, uncertain; open, undiagnosed; quarter-filled, suspected affected; and arrow, proband. The smaller numbers above the gender symbols indicate age at death or diagnosis. The most proximal shared allele, from marker D1S240, is not shown for clarity. D1S2711 is about 186 kb proximal to FIBL-6, D1S444, D1S254, D1S 191, and D1S2848 are within FIBL-6, and D1S2138 is about 206 kb distal to FIBL-6.

In this study, no evidence was found to demonstrate that the Gln5345Arg variation has occurred on different chromosomal backgrounds. Rather, it appears to have a common founder. In all four families studied and probably in the two control subjects and lone sporadic case, the Gln5345Arg variation is associated with a unique shared haplotype. In families B and C, this haplotype could not have originated from the parent who is the family member (FIG. 5). In family D, the other affected family members do not share this unique haplotype.

In order to confirm the inheritance of the Gln5345Arg variation from the spouse (II-1) in family C, DNA has been obtained from some of his relatives, including a niece and a nephew. Although the 85-year old nephew, whose diagnosis is uncertain for AMD (Klein M L, *Arch Ophthalmol* 116: 1082-8, 1998), does not carry the Gln5345Arg variation, the 89-year old niece, who is not affected, does carry the variation. She also shares the same unique haplotype that is found associated with the variation as well as a more extensive haplotype that is found in the two affected family C members (III-2 and III-3) that carry the variation. This demonstrates that the spouse (II-1) was the source of the variation in family C. This also suggests the possibility of a protective gene for AMD or that other genetic and environmental factors may contribute to AMD.

The degree of conservation of an amino acid across species is often an indication of its functional importance. (Valdar W S, *Proteins* 48:227-41, 2002.) Gln5345 is conserved in seven other mammals and chicken, suggesting an important functional role. In most cbEGF domains, this position is occupied by either tyrosine or phenylalanine. It is usually involved in a hydrophobic packing interaction with a glycine in the adjacent downstream cbEGF domain. (Handford Pa., *Biochim Biophys Acta* 1498:84-90, 2000.) However, in FIBL-6 it is conserved as glutamine in the novel cbEGF domain encoded by exon 104. This domain is novel because it contains an additional 76 amino acids at its carboxy terminus instead of the usual one or two that link tandem cbEGF domains (Downing A K, Knott V, *Cell* 85:597-605, 1996), and because exon 104 exhibits alternative splicing. In general, FIBL-6 appears to be a very highly conserved protein. The overall amino acid identity between the mouse and human FIBL-6 sequence is 4745/5751 or 82%. In twelve unique human copies of FIBL-6, there are only seven non-synonymous changes besides the Gln4345Arg variation.

The ortholog of FIBL-6, hemicentin in *C. elegans*, is associated with a variety of cell-matrix and cell-cell interactions. (Vogel B E, *Development* 128:883-94, 2001.) It functions between neurons and epidermis but elsewhere functions across basement membranes between tissues. FIBL-6 may thus be involved in interactions where drusen form, between the basal lamina of the RPE and the inner collagenous layer of Bruch's membrane. Interestingly, other members of the fibulin gene family are located within chromosomal regions recently identified in genome-wide scans for AMD genes (Iyengar et al., *ARVO;* 2002:Abstract #1844.). The fibulin family of proteins may play a major role in AMD and other macular dystrophies.

The evidence is strong for a conclusion that the Gln5345Arg change in the FIBL-6 gene is responsible for AMD in a large family, and may contribute to the disease in three others. The appreciation of FIBL-6 as the gene for ARMD1, along with the discovery of other genes that cause AMD, will result in earlier diagnosis of individuals potentially at risk for AMD, allow more appropriate screening to detect early disease at the stage where treatment might be most efficacious, facilitate the investigation of environmental and genetic modifiers of the age of onset and severity of the phenotype, and allow sufficient understanding at the molecular and biochemical level such that rational gene-based therapies can be devised and tested. Modifier genes have already been reported to significantly affect the age of onset and expression of genetic disease. Examples of modifier genes include the Alu polymorphism in the angiotensin-converting enzyme (ACE) gene (Hamdi H K, *Biochem Biophys Res Commun* 295:668-72, 2002), and the null allele for ciliary neurotrophic factor (CNTF), which has a detrimental effect on the expression of amyotrophic lateral sclerosis from mutation of the SOD-1 gene. (Giess R, *Am J Hum Genet* 70:1277-86, 2002.) The study of the interaction of mutations of genes that cause AMD with sequence changes in other modifier genes will give new targets for pharmaceutical companies to create drugs that might prevent AMD or forestall the occurrence of the major vision loss in later stages.

The present invention is the first indication that a mutation in FIBL-6 in humans is associated with AMD. As such it provides the opportunity to detect the disease at an early stage, and to tailor therapy appropriately to affected family members, before the disease progresses to a point at which vision is irreversibly impaired. The identification of this mutation is also useful for providing methods and materials for elucidating the role of FIBL-6 in both normal retinal function, and loss of that function in AMD. Evidence that the glutamine affected by the mutation plays an important role in the function of FIBL-6 is indicated by the conservation of glutamine at that position in every mammalian species studied to date (mouse, rat, cat, dog, sheep, rabbit and pig), as well as chicken.

Methods are known in the art for identifying and screening for a polynucleotide sequence carrying a point mutation, and these methods are applicable to identifying carriers of the mutation of the present invention. U.S. Patent Publication 20010016323 discloses methods for detecting point mutations using a fluorescently labeled oligomeric probe and fluorescence resonance energy transfer. A point mutation leading to a base mismatch between the probe and the target DNA strand causes the melting temperature of the complex to be lower than the melting temperature for the probe and the target if the probe and target were perfectly matched. A suitable probe consists of SEQ ID NO:7, wherein this probe, 5'ACCAGGACAACATTTAT3', is a perfect match to the comparable region of the wild type gene. Another suitable probe is SEQ ID NO:8, 5'ACCAGGACGACATTTAT3', which differs from SEQ ID NO:7 by a substitution of G for A. This probe is a perfect match for the corresponding region of the mutated gene of the invention. Thus, the invention provides probes for detecting the wild type gene by perfect match, and for detecting the mutated gene by perfect match. Other suitable probes comprise SEQ ID NO:7 or 8, in which one or more additional nucleotides are present at one of both ends of the probe, wherein the additional nucleotides do not interfere with the binding efficiency that is characteristic of the corresponding probe of SEQ ID NO:7 or 8. Examples of such probes include SEQ ID NO: 12-94 for the wild-type gene, and SEQ ID NO:95-177 for the mutation.

Other suitable methods for detecting single point mutations include those disclosed in, for example, U.S. Patent Publication 2002010665, which involves the use of oligonucleotide probes in array format. Such arrays can include one or more of SEQ ID NO:7, 8, and 12-177. U.S. Patent Publication 20020177157 discloses additional methods for detecting point mutations.

A polynucleotide carrying the point mutation that is the subject of this invention can be identified using one or more of a number of available techniques. However, detection is not limited to the techniques described herein and the methods and compositions of the invention are not limited to these methods, which are provided for exemplary purposes only. Polynucleotide and oligonucleotide probes are also disclosed herein and are within the scope of the invention, and these probes are suitable for one or more of the techniques described below. These include allele-specific oligo hybridization (ASO), which, in one embodiment, is a diagnostic mutation detection method wherein hybridization with a pair of oligos corresponding to alleles of a known mutation is used to detect the mutation. Another suitable method is denaturing high performance liquid chromatography (DHPLC), which is a liquid chromatography method designed to identify mutations and polymorphisms based on detection of heteroduplex formation between mismatched nucleotides. Under specified conditions, heteroduplexes elute from the column earlier than homoduplexes because of reduced melting temperature. Analysis can then be performed on individual samples.

An amplified region of the DNA containing the mutation or the wild-type sequence can be analyzed by DHPLC. In the present invention, DHPLC was performed on a 194 base pair PCR product generated using the forward primer SEQ ID NO:3 and the reverse primer SEQ ID NO:4. Use of DHPLC is described in U.S. Pat. Nos. 5,795,976 and 6,453,244, both of which are incorporated herein by reference. A suitable method is that provided by Transgenomic, Inc. (Omaha, Nebr.) using the Transgenomic WAVE® System.

For ASO, a region of genomic DNA or cDNA containing the mutation is amplified by PCR and transferred onto duplicating membranes. This can be performed by dot/slot blotting, spotting by hand, or digestion and Southern blotting. The membranes are prehybridized, then hybridized with a radiolabelled or deoxygenin (DIG) labelledoligonucleotide to either the mutant or wild-type sequences. For the DIG label, detection is performed using chemiluminescent or colorimetric methods. The membranes are then washed with increasing stringency until the ASO is washed from the non-specific sequence. Following autoradiographic exposure, the products are scored for the level of hybridization to each oligo. Optimally, controls are included for the normal and mutant sequence on each filter to confirm correct stringency, and a negative PCR control is used to check for contamination in the PCR.

The size of the ASO probe is not limited except by technical parameters of the art. Generally, too short a probe will not be unique to the location, and too long a probe may cause loss of sensitivity. The oligos are preferably 15-21 nucleotides in length, with the mismatch towards the center of the oligo. Most preferable oligos for the present invention include SEQ ID NO:7 for the wild-type, and SEQ ID NO:8 for the mutant sequence. These oligos represent nucleotides of position 16,255 to position 16,271 of SEQ ID NO:1. For SEQ ID NO:8, position 16,263 is G instead of A. Other suitable wild-type oligos include nucleotides of position 16,256 to position 16,272; 16,257 to 16,273; 16,258 to 16,274; and 16,259 to 16,275, all with reference to SEQ ID NO:1. For the corresponding mutant oligo, in each case, position 16,263 is G instead of A. The foregoing examples are 17-mer oligos. Also suitable are 15, 16, 18, 19, 20, and 21-mer oligos, wherein each of the oligos described here can be extended at one or both ends by one or more nucleotides as shown in the corresponding region of SEQ ID NO:1, and in each case the wild-type and mutant oligos differ at position 16,263, which is A for the wild-type oligo and G for the mutant oligo.

Exemplary wild-type oligos, with the "A" at position 16,263 of SEQ ID NO:1 indicated in bold, include:

```
15-mers:
GACAACATTTATTAG            (SEQ ID NO:12)

GGACAACATTTATTA            (SEQ ID NO:13)

AGGACAACATTTATT            (SEQ ID NO:14)

CAGGACAACATTTAT            (SEQ ID NO:15)

CCAGGACAACATTTA            (SEQ ID NO:16)

ACCAGGACAACATTT            (SEQ ID NO:17)

CACCAGGACAACATT            (SEQ ID NO:18)

CCACCAGGACAACAT            (SEQ ID NO:19)

TCCACCAGGACAACA            (SEQ ID NO:20)

16-mers:
GACAACATTTATTAGG           (SEQ ID NO:21)

GGACAACATTTATTAG           (SEQ ID NO:22)

AGGACAACATTTATTA           (SEQ ID NO:23)

CAGGACAACATTTATT           (SEQ ID NO:24)

CCAGGACAACATTTAT           (SEQ ID NO:25)

ACCAGGACAACATTTA           (SEQ ID NO:26)

CACCAGGACAACATTT           (SEQ ID NO:27)

CCACCAGGACAACATT           (SEQ ID NO:28)

TCCACCAGGACAACAT           (SEQ ID NO:29)

GTCCACCAGGACAACA           (SEQ ID NO:30)

17-mers:
GACAACATTTATTAGGG          (SEQ ID NO:31)

GGACAACATTTATTAGG          (SEQ ID NO:32)

AGGACAACATTTATTAG          (SEQ ID NO:33)

CAGGACAACATTTATTA          (SEQ ID NO:34)

CCAGGACAACATTTATT          (SEQ ID NO:35)

ACCAGGACAACATTTAT          (SEQ ID NO:7)

CACCAGGACAACATTTA          (SEQ ID NO:36)

CCACCAGGACAACATTT          (SEQ ID NO:37)

TCCACCAGGACAACATT          (SEQ ID NO:38)

GTCCACCAGGACAACAT          (SEQ ID NO:39)

TGTCCACCAGGACAACA          (SEQ ID NO:40)

18-mers:
GACAACATTTATTAGGGG         (SEQ ID NO:41)

GGACAACATTTATTAGGG         (SEQ ID NO:42)

AGGACAACATTTATTAGG         (SEQ ID NO:43)

CAGGACAACATTTATTAG         (SEQ ID NO:44)

CCAGGACAACATTTATTA         (SEQ ID NO:45)

ACCAGGACAACATTTATT         (SEQ ID NO:46)

CACCAGGACAACATTTAT         (SEQ ID NO:47)

CCACCAGGACAACATTTA         (SEQ ID NO:48)

TCCACCAGGACAACATTT         (SEQ ID NO:49)

GTCCACCAGGACAACATT         (SEQ ID NO:50)

TGTCCACCAGGACAACAT         (SEQ ID NO:51)

CTGTCCACCAGGACAACA         (SEQ ID NO:52)

19-mers:
GACAACATTTATTAGGGGA        (SEQ ID NO:53)

GGACAACATTTATTAGGGG        (SEQ ID NO:54)

AGGACAACATTTATTAGGG        (SEQ ID NO:55)

CAGGACAACATTTATTAGG        (SEQ ID NO:56)

CCAGGACAACATTTATTAG        (SEQ ID NO:57)

ACCAGGACAACATTTATTA        (SEQ ID NO:58)

CACCAGGACAACATTTATT        (SEQ ID NO:59)

CCACCAGGACAACATTTAT        (SEQ ID NO:60)

TCCACCAGGACAACATTTA        (SEQ ID NO:61)

GTCCACCAGGACAACATTT        (SEQ ID NO:62)

TGTCCACCAGGACAACATT        (SEQ ID NO:63)

CTGTCCACCAGGACAACAT        (SEQ ID NO:64)

TCTGTCCACCAGGACAACA        (SEQ ID NO:65)

20-mers:
GACAACATTTATTAGGGGAC       (SEQ ID NO:66)

GGACAACATTTATTAGGGGA       (SEQ ID NO:67)

AGGACAACATTTATTAGGGG       (SEQ ID NO:68)

CAGGACAACATTTATTAGGG       (SEQ ID NO:69)

CCAGGACAACATTTATTAGG       (SEQ ID NO:70)

ACCAGGACAACATTTATTAG       (SEQ ID NO:71)

CACCAGGACAACATTTATTA       (SEQ ID NO:72)

CCACCAGGACAACATTTATT       (SEQ ID NO:73)

TCCACCAGGACAACATTTAT       (SEQ ID NO:74)

GTCCACCAGGACAACATTTA       (SEQ ID NO:75)

TGTCCACCAGGACAACATTT       (SEQ ID NO:76)

CTGTCCACCAGGACAACATT       (SEQ ID NO:77)

TCTGTCCACCAGGACAACAT       (SEQ ID NO:78)

ATCTGTCCACCAGGACAACA       (SEQ ID NO:79)

21-mers:
GACAACATTTATTAGGGGACG      (SEQ ID NO:80)

GGACAACATTTATTAGGGGAC      (SEQ ID NO:81)

AGGACAACATTTATTAGGGGA      (SEQ ID NO:82)
```

```
CAGGACAACATTTATTAGGGG    (SEQ ID NO:83)
CCAGGACAACATTTATTAGGG    (SEQ ID NO:84)
ACCAGGACAACATTTATTAGG    (SEQ ID NO:85)
CACCAGGACAACATTTATTAG    (SEQ ID NO:86)
CCACCAGGACAACATTTATTA    (SEQ ID NO:87)
TCCACCAGGACAACATTTATT    (SEQ ID NO:88)
GTCCACCAGGACAACATTTAT    (SEQ ID NO:89)
TGTCCACCAGGACAACATTTA    (SEQ ID NO:90)
CTGTCCACCAGGACAACATTT    (SEQ ID NO:91)
TCTGTCCACCAGGACAACATT    (SEQ ID NO:92)
ATCTGTCCACCAGGACAACAT    (SEQ ID NO:93)
TATCTGTCCACCAGGACAACA    (SEQ ID NO:94)
```

Exemplary oligos for detecting the mutation, with a "G" instead of an "A" at position 16,263 of SEQ ID NO:1 indicated in bold, include:

```
15-mers:
GACGACATTTATTAG          (SEQ ID NO:95)
GGACGACATTTATTA          (SEQ ID NO:96)
AGGACGACATTTATT          (SEQ ID NO:97)
CAGGACGACATTTAT          (SEQ ID NO:98)
CCAGGACGACATTTA          (SEQ ID NO:99)
ACCAGGACGACATTT          (SEQ ID NO:100)
CACCAGGACGACATT          (SEQ ID NO:101)
CCACCAGGACGACAT          (SEQ ID NO:102)
TCCACCAGGACGACA          (SEQ ID NO:103)

16-mers:
GACGACATTTATTAGG         (SEQ ID NO:104)
GGACGACATTTATTAG         (SEQ ID NO:105)
AGGACGACATTTATTA         (SEQ ID NO:106)
CAGGACGACATTTATT         (SEQ ID NO:107)
CCAGGACGACATTTAT         (SEQ ID NO:108)
ACCAGGACGACATTTA         (SEQ ID NO:109)
CACCAGGACGACATTT         (SEQ ID NO:110)
CCACCAGGACGACATT         (SEQ ID NO:111)
TCCACCAGGACGACAT         (SEQ ID NO:112)
GTCCACCAGGACGACA         (SEQ ID NO:113)

17-mers:
GACGACATTTATTAGGG        (SEQ ID NO:114)
GGACGACATTTATTAGG        (SEQ ID NO:115)
AGGACGACATTTATTAG        (SEQ ID NO:116)
CAGGACGACATTTATTA        (SEQ ID NO:117)
CCAGGACGACATTTATT        (SEQ ID NO:118)
ACCAGGACGACATTTAT        (SEQ ID NO:8)
CACCAGGACGACATTTA        (SEQ ID NO:119)
CCACCAGGACGACATTT        (SEQ ID NO:120)
TCCACCAGGACGACATT        (SEQ ID NO:121)
GTCCACCAGGACGACAT        (SEQ ID NO:122)
TGTCCACCAGGACGACA        (SEQ ID NO:123)

18-mers:
GACGACATTTATTAGGGG       (SEQ ID NO:124)
GGACGACATTTATTAGGG       (SEQ ID NO:125)
AGGACGACATTTATTAGG       (SEQ ID NO:126)
CAGGACGACATTTATTAG       (SEQ ID NO:127)
CCAGGACGACATTTATTA       (SEQ ID NO:128)
ACCAGGACGACATTTATT       (SEQ ID NO:129)
CACCAGGACGACATTTAT       (SEQ ID NO:130)
CCACCAGGACGACATTTA       (SEQ ID NO:131)
TCCACCAGGACGACATTT       (SEQ ID NO:132)
GTCCACCAGGACGACATT       (SEQ ID NO:133)
TGTCCACCAGGACGACAT       (SEQ ID NO:134)
CTGTCCACCAGGACGACA       (SEQ ID NO:135)

19-mers:
GACGACATTTATTAGGGGA      (SEQ ID NO:136)
GGACGACATTTATTAGGGG      (SEQ ID NO:137)
AGGACGACATTTATTAGGG      (SEQ ID NO:138)
CAGGACGACATTTATTAGG      (SEQ ID NO:139)
CCAGGACGACATTTATTAG      (SEQ ID NO:140)
ACCAGGACGACATTTATTA      (SEQ ID NO:141)
CACCAGGACGACATTTATT      (SEQ ID NO:142)
CCACCAGGACGACATTTAT      (SEQ ID NO:143)
TCCACCAGGACGACATTTA      (SEQ ID NO:144)
GTCCACCAGGACGACATTT      (SEQ ID NO:145)
TGTCCACCAGGACGACATT      (SEQ ID NO:146)
CTGTCCACCAGGACGACAT      (SEQ ID NO:147)
TCTGTCCACCAGGACGACA      (SEQ ID NO:148)

20-mers:
GACGACATTTATTAGGGGAC     (SEQ ID NO:149)
GGACGACATTTATTAGGGGA     (SEQ ID NO:150)
AGGACGACATTTATTAGGGG     (SEQ ID NO:151)
CAGGACGACATTTATTAGGG     (SEQ ID NO:152)
CCAGGACGACATTTATTAGG     (SEQ ID NO:153)
ACCAGGACGACATTTATTAG     (SEQ ID NO:154)
CACCAGGACGACATTTATTA     (SEQ ID NO:155)
```

```
              -continued
CCACCAGGACGACATTTATT       (SEQ ID NO:156)

TCCACCAGGACGACATTTAT       (SEQ ID NO:157)

GTCCACCAGGACGACATTTA       (SEQ ID NO:158)

TGTCCACCAGGACGACATTT       (SEQ ID NO:159)

CTGTCCACCAGGACGACATT       (SEQ ID NO:160)

TCTGTCCACCAGGACGACAT       (SEQ ID NO:161)

ATCTGTCCACCAGGACGACA       (SEQ ID NO:162)

21-mers:
GACGACATTTATTAGGGGACG      (SEQ ID NO:163)

GGACGACATTTATTAGGGGAC      (SEQ ID NO:164)

AGGACGACATTTATTAGGGGA      (SEQ ID NO:165)

CAGGACGACATTTATTAGGGG      (SEQ ID NO:166)

CCAGGACGACATTTATTAGGG      (SEQ ID NO:167)

ACCAGGACGACATTTATTAGG      (SEQ ID NO:168)

CACCAGGACGACATTTATTAG      (SEQ ID NO:169)

CCACCAGGACGACATTTATTA      (SEQ ID NO:170)

TCCACCAGGACGACATTTATT      (SEQ ID NO:171)

GTCCACCAGGACGACATTTAT      (SEQ ID NO:172)

TGTCCACCAGGACGACATTTA      (SEQ ID NO:173)

CTGTCCACCAGGACGACATTT      (SEQ ID NO:174)

TCTGTCCACCAGGACGACATT      (SEQ ID NO:175)

ATCTGTCCACCAGGACGACAT      (SEQ ID NO:176)

TATCTGTCCACCAGGACGACA      (SEQ ID NO:177)
```

The region of sample DNA on which ASO hybridization is performed to detect the mutation of this invention is preferably amplified by PCR using a forward primer, SEQ ID NO:5, and a reverse primer, SEQ ID NO:6. This amplification yields a 462 nucleotide product within which the mutated site is located. Alternatively, the mutation can be detected using cloned DNA that includes the region of interest, specifically, the region of DNA including position 16,263 of SEQ ID NO:1, and sequencing the DNA. In this case, amplification by PCR or a comparable method is not necessary but can optionally be performed.

Optionally, one or more than one of the amplified regions described above, (including the 462 nucleotide region generated using primers of SEQ ID NO:5 and 6, and the 194 nucleotide region generated using primers of SEQ ID NO:3 and 4), or shorter portions of either of these regions, can be analyzed by sequencing in order to detect the mutation. Sequencing can be performed as is routine in the art. The only limitation on choice of the region to be sequenced, in order to identify the presence of the mutation, is that the region selected for sequencing must include the nucleotide that is the subject of the mutation, which is position 16,263 of SEQ ID NO:1 (based on the publicly available sequence). Deletions or insertions upstream of this site could affect whether the mutation appears at position 16,263 but such deletions or insertions would not affect detection of the point mutation using the methods and probes described herein. The size of the region selected for sequencing is not limited except by technical parameters as is known in the art, and longer regions comprising part or all of the 462 or the 194 base regions disclosed herein can be sequenced.

Variations of the methods disclosed above are also suitable for detecting the mutation. For example, in a variation of ASO, the ASO's are given homopolymer tails with terminal deoxyribonucleotidyl transferase, spotted onto nylon membrane, and covalently bound by UV irradiation. The target DNA is amplified with biotinylated primers and hybridized to the membrane containing the immobilized oligos, followed by detection. An example of this reverse dot blot technique is the INNO-LIPA kit from Innogenetics (Belgium).

The mutation identified herein is related to AMD pathology. With the identification and sequencing of the mutated gene and the gene product, probes and antibodies raised to the gene product can be used in a variety of hybridization and immunological assays to screen for and detect the presence of either a normal or mutated gene or gene product.

Patient therapy through removal or blocking of the mutant gene product, as well as supplementation with the normal gene product by amplification, by genetic and recombinant techniques or by immunotherapy can be achieved. Correction or modification of the defective gene product by protein treatment immunotherapy (using antibodies to the defective protein) or knock-out of the mutated gene is now also possible. Familial AMD could also be controlled by gene therapy in which the gene defect is corrected in situ or by the use of recombinant or other vehicles to deliver a DNA sequence capable of expressing the normal gene product, or a deliberately mutated version of the gene product whose effect counterbalances the deleterious consequences of the disease mutation to the affected cells of the patient.

Expression of the mutated gene in heterologous cell systems can be used to demonstrate structure function relationships. Ligating the DNA sequence into a plasmid expression vector to transfect cells is a useful method to test the influence of the mutation on various cellular biochemical parameters. Plasmid expression vectors containing either the entire normal or mutant human or mouse sequence or portions thereof, can be used in in vitro mutagenesis experiments which will identify portions of the protein crucial for regulatory function.

The DNA sequence can be manipulated in studies to understand the expression of the gene and its product, and to achieve production of large quantities of the protein for functional analysis, for antibody production, and for patient therapy. Changes in the sequence may or may not alter the expression pattern in terms of relative quantities, tissue-specificity and functional properties.

The protein can be expressed in insect cells using baculoviral vectors, or in mammalian cells using vaccinia virus or specialized eukaryotic expression vectors. For expression in mammalian cells, the cDNA sequence may be ligated to heterologous promoters, such as the simian virus (SV 40) promoter in the pSV2 vector or other similar vectors and introduced into cultured eukaryotic cells such as COS cells to achieve transient or long-term expression. The stable integration of the chimeric gene construct may be maintained in mammalian cells by biochemical selection, such as neomycin and mycophenolic acid.

The DNA sequence can be altered using procedures such as restriction enzyme digestion, fill-in with DNA polymerase, deletion by exonuclease, extension by terminal deoxynucleotide transferase, ligation of synthetic or cloned DNA sequences and site-directed sequence alteration with the use of specific oligonucleotides together with PCR.

The cDNA sequence or portions thereof is introduced into eukaryotic expression vectors by conventional techniques. These vectors permit the transcription of the cDNA in eukaryotic cells by providing regulatory sequences that initiate and enhance the transcription of the cDNA and ensure its proper splicing and polyadenylation. The endogenous FIBL-6 gene promoter can also be used. Different promoters within vectors have different activities, which alters the level of expression of the cDNA. In addition, certain promoters can also modulate function such as the glucocorticoid-responsive promoter from the mouse mammary tumor virus.

Cell lines can also be produced which have integrated the vector into the genomic DNA. In this manner, the gene product is produced on a continuous basis. Vectors are introduced into recipient cells by various methods including calcium phosphate, strontium phosphate, electroporation, lipofection, DEAE dextran, microinjection, or by protoplast fusion. Alternatively, the cDNA can be introduced by infection using viral vectors. Using the techniques mentioned, the expression vectors containing the FIBL-6 gene or portions thereof can be introduced into a variety of mammalian cells from other species or into non-mammalian cells.

The recombinant expression vector, according to this invention, comprises the selected DNA of the DNA sequences of this invention for expression in a suitable host. The DNA is operatively joined in the vector to an expression control sequence in the recombinant DNA molecule so that normal or mutant protein can be expressed. The expression control sequence may be selected from the group consisting of sequences that control the expression of genes of prokaryotic or eukaryotic cells and their viruses and combinations thereof. The expression control sequence may be selected from the group consisting of the lac system, the trp system, the tac system, the trc system, major operator and promoter regions of phage lambda, the control region of the fd coat protein, early and late promoters of SV40, promoters derived from polyoma, adenovirus, retrovirus, baculovirus, simian virus, 3-phosphoglycerate kinase promoter, yeast acid phosphatase promoters, yeast alpha-mating factors and combinations thereof.

The host cells to be transfected with the vectors of this invention may be from a host selected from the group consisting of yeasts, fungi, insects, mice or other animals or plant hosts or may be human tissue cells. For the mutant DNA sequence, similar systems are employed to express and produce the mutant protein.

Antibodies to epitopes within the protein can be raised to provide information on the characteristics of the proteins. Generation of antibodies enables the visualization of the protein in cells and tissues using Western blotting. In this technique, proteins are separated by polyacrylamide gel electrophoresis and transferred to nitrocellulose membranes. These membranes are then incubated in the presence of a primary antibody, washed and incubated with a secondary antibody to detect the protein-primary antibody complex. Following repeated washing, the entire complex is visualized using colorimetric or chemiluminescent methods.

Antibodies to the protein also allow for the use of immunocytochemistry and immunofluorescence techniques in which the proteins can be visualized directly in cells and tissues. This is most helpful in order to establish the subcellular location of the protein and the tissue specificity of the protein.

In order to prepare polyclonal antibodies, fusion proteins containing defined portions or all of the protein may be synthesized in bacteria by expression of corresponding DNA sequences in a suitable cloning vehicle, as described herein. The protein is then purified, coupled to a carrier protein, mixed with Freund's adjuvant (to help stimulate the antigenic response) and injected into rabbits or other suitable animals. Alternatively, protein can be isolated from cultured cells expressing the protein. Following booster injections at bi-weekly intervals, the rabbits or other suitable animals are bled and the sera isolated. Sera are used directly or purified prior to use, by various methods including affinity chromatography, Protein A-Sepharose, Antigen Sepharose, Anti-mouse-Ig-Sepharose. Sera or purified antibodies are used to probe protein extracts run on a polyacrylamide gel to identify the FIBL-6 protein. Alternatively, antibodies may be obtained by making synthetic peptides corresponding to antigenic portions of the protein and injecting these into rabbits or other suitable animals.

To produce monoclonal antibodies, cells actively expressing the wild type or mutant FIBL-6 protein are cultured or isolated from tissues and the cell membranes isolated. The membranes, extracts, or recombinant protein extracts containing the protein are injected in Freund's adjuvant into mice. After receiving nine injections over a three week period, the mice are sacrificed and their spleens are removed and resuspended in phosphate buffered saline (PBS). The spleen cells serve as a source of lymphocytes, some of which produce antibody of the appropriate specificity. These cells are then fused with a permanently growing myeloma partner cell, and the products of the fusion are plated into a number of tissue culture wells in the presence of a selective agent such as HAT. The wells are screened by ELISA to identify those containing cells making useful antibody and these cells are freshly plated. After a period of growth, these cells are again screened to identify antibody-producing cells. Several cloning procedures are carried out until over 90% of the wells contain single clones which are positive for antibody production. By this procedure, a stable line of monoclonal antibody-producing clones is established. Monoclonal antibody produced by such clones is purified by methods such as affinity chromatography using Protein A Sepharose or ion-exchange chromatography or by variations and combinations of these techniques.

Antibodies may also be used coupled to other compounds or materials for diagnostic and/or therapeutic uses. For example, they may be coupled to radionuclides for imaging and therapy, or to liposomes for the targeting of compounds contained in the liposomes to a specific tissue location.

Transgenic Mouse Model

The creation of a mouse model for AMD is important to the understanding of the disease and for the testing of possible therapies. There are several ways in which to create an animal model for AMD. One strategy is the generation, in the mouse gene, of a specific mutation such as the herein identified human gene mutation. Secondly, a wild type human gene could be inserted and/or the murine gene could be humanized by homologous recombination. Thirdly, it is possible to insert a mutant (single or multiple) human gene as a genomic or minigene cDNA construct using wild type, mutant or artificial promoter elements. Fourthly, knock-out of the endogenous murine genes may be accomplished by the insertion of artificially modified fragments of the endogenous gene by homologous recombination. The modifications include insertion of mutant stop codons, the deletion of DNA sequences, or the inclusion of recombination elements (lox p sites) recognized by enzymes such as Cre recombinase.

To inactivate the corresponding mouse gene, chemical or x-ray mutagenesis of mouse gametes, followed by fertilization, can be applied. Heterozygous offspring may be identified by Southern blotting to demonstrate loss of one allele by dosage, or failure to inherit one parental allele using RFLP markers.

To create a transgenic mouse, a mutant version of the human or mouse gene can be inserted into a mouse germ line using standard techniques of oocyte microinjection, or transfection or microinjection into stem cells. Alternatively, if it is desired to inactivate or replace the endogenous FIBL-6 gene, homologous recombination using embryonic stem cells may be applied.

For oocyte injection, one or more copies of the mutant or wild type gene can be inserted into the pronucleus of a just-fertilized mouse oocyte. This oocyte is then reimplanted into a pseudo-pregnant foster mother. The liveborn mice are screened for integrants using analysis of tail DNA for the presence of human gene sequences. The transgene may be either a complete genomic sequence injected as a YAC, BAC, PAC or other chromosome DNA fragment, a cDNA with either the natural promoter or a heterologous promoter, or a minigene containing all of the coding region and other elements found to be necessary for optimum expression.

Retroviral infection of early embryos can also be done to insert the mutant or wild type human gene. In this method, the mutant or wild type gene is inserted into a retroviral vector which is used to infect mouse embryos directly during the early stages of development to generate chimeras, some of which will lead to germline transmission. Similar experiments can be conducted in the case of mutant proteins, using mutant murine or other animal gene sequences.

Homologous recombination using stem cells allows for the screening of gene transfer cells to identify the rare homologous recombination events. Once identified, these can be used to generate chimeras by injection of mouse blastocysts, and a proportion the resulting mice will show germline transmission from the recombinant line. This methodology is especially useful if inactivation of the mouse gene is desired. For example, inactivation of the mouse gene can be done by designing a DNA fragment which contains sequences from a mouse exon flanking a selectable marker. Homologous recombination leads to the insertion of the marker sequences in the middle of an exon, inactivating the FIBL-6 gene. DNA analysis of individual clones can be used to recognize the homologous recombination events.

It is also possible to create mutations in the mouse germline by injecting oligonucleotides containing the mutation of interest and screening the resulting cells by PCR.

Isolation of FIBL-6 Binding Proteins

Isolation of interacting partners of the FIBL-6 allows identification of the biochemical partners for the FIBL-6 and thus the identification of the biochemical pathway disturbed by mutations in FIBL-6. Such partners could be for example, enzymes, co-receptors, ligands or stabilizers. By analyzing these interactions, it is possible to design compounds which counteract the effect of the mutation interaction, thus providing treatment for abnormal interactions. These treatments might alter the interaction of the FIBL-6 with these partners, they may alter the function of the interacting protein, they may alter the amount or tissue distribution or expression of the interaction partners, or they may alter similar properties of the FIBL-6.

Soluble recombinant fusion proteins can be made in suitable vectors (yeast-2-hybrid, baculovirus, and phage-display systems for instance) and used to identify other proteins which interact with FIBL-6 in the pathogenesis of AMD. Therapies can be designed to modulate these interactions and thus modulate AMD and the other conditions associated with acquired or inherited abnormalities of the FIBL-6 gene or gene products. The potential efficacy of these therapies can be tested by analyzing the affinity and function of these interactions after exposure to the therapeutic agent by standard pharmacokinetic measurements of affinity (Kd and Vmax etc.) using synthetic peptides or recombinant proteins corresponding to functional domains of the FIBL-6 gene. Another method for assaying the effect of any interactions involving functional domains is to monitor changes in the intracellular trafficking and post-translational modification of the relevant genes by in situ hybridization, immunohistochemistry, Western blotting and metabolic pulse-chase labelling studies in the presence of, and in the absence of, the therapeutic agents. A further method is to monitor the effects of "downstream" events including (i) changes in the intracellular metabolism, trafficking and targeting of APP and its products; (ii) changes in second messenger events.

Two-Hybrid Yeast System

The Two-Hybrid system, which is known in the art, takes advantage of transcriptional factors that are composed of two physically separable, functional domains. The most commonly used is the yeast GAL4 transcriptional activator consisting of a DNA binding domain and a transcriptional activation domain. Two different cloning vectors are used to generate separate fusions of the GAL4 domains to genes encoding potential binding proteins. The fusion proteins are co-expressed, targeted to the nucleus and, if interactions occur, activation of a reporter gene (e.g. lacZ) produces a detectable phenotype.

Identification of Small Molecules with FIBL-6 Binding Capacity

Small molecule-based therapies are particularly preferred because such molecules are more readily absorbed after oral administration, and have fewer potential antigenic determinants than larger, protein-based pharmaceuticals. In light of the present disclosure, one of ordinary skill in the art is enabled to develop drug screening methodologies which will be useful in the identification of candidate small molecule pharmaceuticals for the treatment of AMD. In particular, one is enabled to screen large libraries of small molecules in order to identify those which bind to the normal and/or mutant protein and which, therefore, are candidates for modifying the in vivo activity of the normal or mutant FIBL-6 proteins. Furthermore, one is enabled to identify small molecules which selectively or preferentially bind to a mutant form of a protein and which, therefore, may have particular utility in treating heterozygous carriers of this disease.

Methods for screening small molecule libraries for candidate protein-binding molecules are well known in the art and, in light of the present disclosure, may now be employed to identify compounds which bind to the normal or mutant forms of FIBL-6. Briefly, in one embodiment, either a normal or mutant FIBL-6 protein may be immobilized on a substrate such as a column or filter, and a solution including the test compound(s) is contacted with the FIBL-6 protein under conditions which are permissive for binding. The substrate is then washed with a solution which substantially reflects physiological conditions to remove unbound or weakly bound small molecules. A second wash may then elute those compounds which strongly bound to the immobilized normal or mutant FIBL-6. Alternatively, the small molecule test compounds may be immobilized and a solution of normal or mutant FIBL-6 may be contacted with the column, filter or other substrate. The ability of the FIBL-6 to bind to the small molecules may be determined as above or a labelled form of FIBL-6 (e.g., radio-labelled or chemiluminescent) may be used to more rapidly assess binding to the substrate immobilized compound(s). In addition, as FIBL-6 is believed to be a membrane associated protein, it may be preferred that the FIBL-6 protein be incorporated into lipid bilayers (e.g., liposomes) to promote its proper folding. Such FIBL-6-liposomes may be immobilized on substrates (either directly or by means of another element in the liposome membrane), passed over substrates with immobilized small molecules, or used in any of a variety of other well known binding assays for membrane proteins.

In another series of embodiments, either normal or mutant, free or membrane-bound FIBL-6 may be mixed in a solution with the candidate compound(s) under conditions which are permissive for binding, and the FIBL-6 may be immunoprecipitated. Small molecules which co-immunoprecipitate with a FIBL-6 may then be identified. As will be obvious to one of ordinary skill in the art, there are numerous other methods of screening individual small molecules or large libraries of small molecules (e.g., phage display libraries) to identify compounds which bind to normal or mutant FIBL-6. All of these methods comprise the step of mixing normal or mutant FIBL-6 with test compounds, allowing for binding (if any), and assaying for bound complexes. All such methods are now enabled by the present disclosure of the mutant FIBL-6 protein.

Because the normal physiological roles of FIBL-6 is still unknown, compounds which bind to normal or mutant or both forms of FIBL-6 may have utility in treatments. Compounds which bind only to a normal FIBL-6 may, for example, act as enhancers of its normal activity and thereby at least partially compensate for the lost or abnormal activity of mutant forms of the FIBL-6 in AMD patients. Compounds which bind to both normal and mutant forms of a FIBL-6 may have utility if they differentially affect the activities of the two forms so as to alleviate the overall departure from normal function. Alternatively, blocking the activity of both normal and mutant forms of FIBL-6 in heterozygotes may have less severe physiological and clinical consequences than the normal progress of the disease and, therefore, compounds which bind to and inhibit the activity of both normal and mutant forms of a FIBL-6 may have utility. Preferably, however, compounds are identified which have a higher affinity of binding to mutant FIBL-6 than to normal FIBL-6 (e.g., 5-10 fold higher $K_a$) and which selectively or preferentially inhibit the activity of the mutant form. Such compounds may be identified by using any of the techniques described above and by then comparing the binding affinities of the candidate compound(s) for the normal and mutant forms of FIBL-6.

Once identified by the methods described above, the candidate compounds may then be produced in quantities sufficient for pharmaceutical administration or testing (e.g., μg or mg or greater quantities), and formulated in a pharmaceutically acceptable carrier (see, e.g., Remington's Pharmaceutical Sciences, Gennaro, A., ed., Mack Pub., 1990, the disclosure of which is incorporated herein by reference). These candidate compounds may then be administered to AMD patients or animal models of AMD. The animal models described and enabled herein are of particular utility in further testing all candidate molecules which bind to normal or mutant FIBL-6 for their therapeutic efficacy.

Once identified by the methods described above, the candidate compounds may also serve as "lead compounds" in the design and development of new pharmaceuticals. For example, as is well known in the art, sequential modification of small molecules (e.g., amino acid residue replacement with peptides, functional group replacement with peptide or non-peptide compounds) is a standard approach in the pharmaceutical industry for the development of new pharmaceuticals. Such development generally proceeds from a "lead compound" which is shown to have at least some of the activity (e.g., FIBL-6 binding ability) of the desired pharmaceutical. In particular, when one or more compounds having at least some activity of interest (e.g., FIBL-6 binding) are identified, structural comparison of the molecules can greatly inform the skilled practitioner by suggesting portions of the lead compounds which should be conserved and portions which may be varied in the design of new candidate compounds. Thus, the present invention also provides a means of identifying lead compounds which may be sequentially modified to produce new candidate compounds for use in the treatment of AMD. These new compounds then may be tested both for FIBL-6-binding (e.g., in the binding assays described above) and for therapeutic efficacy (e.g., in the animal models described herein). This procedure may be iterated until compounds having the desired therapeutic activity and/or efficacy are identified.

Screening and Diagnosis for AMD

General Diagnostic Methods

The FIBL-6-related genes and gene products, as well as other products derived therefrom (e.g., probes, antibodies), will be useful in the diagnosis of AMD. Diagnosis of inherited cases of these diseases can be accomplished by methods based upon the nucleic acids (including genomic and mRNA/cDNA sequences), proteins, and/or antibodies disclosed and enabled herein. Preferably, the methods and products are based upon the human FIBL-6 nucleic acids, proteins or antibodies disclosed herein. As will be obvious to one of ordinary skill in the art, however, the significant evolutionary conservation of the mutated region of the FIBL-6 nucleotide and amino acid sequences allows the skilled artisan to make use of non-human FIBL-6-homologue nucleic acids, proteins and antibodies even for applications directed toward human or other mammalian subjects.

As will be appreciated by one of ordinary skill in the art, the choice of diagnostic methods of the present invention will be influenced by the nature of the available biological samples to be tested and the nature of the information required. Assays based upon a subject's genomic DNA may be the preferred methods for FIBL-6 diagnostics as no information will he lost due to alternative splicing and because essentially any nucleate cells may provide a usable sample. Diagnostics based upon other FIBL-6-related proteins are subject to similar considerations: availability of tissues, levels of expression in various tissues, and alternative translation products resulting from alternative mRNA splicing.

When a diagnostic assay is to be based upon FIBL-6-related proteins, a variety of approaches are possible. For example, diagnosis can be achieved by monitoring differences in the electrophoretic mobility of normal and mutant proteins. Such an approach will be particularly useful in identifying mutants in which charge substitutions are present, or in which insertions, deletions or substitutions have resulted in a significant change in the molecular mass of the resultant protein. Alternatively, diagnosis may be based upon differences in the proteolytic cleavage patterns of normal and mutant proteins, differences in molar ratios of the various amino acid residues, or by functional assays demonstrating altered function of the gene products. In some preferred embodiments, protein-based diagnostics will employ differences in the ability of antibodies to bind to normal and mutant FIBL-6-related proteins. Such diagnostic tests may employ antibodies which bind to the normal proteins but not to mutant proteins, or vice versa. Because a specific point mutation has been identified in the FIBL-6 gene/protein, and because this mutation appears to be conserved, it is currently preferred that antibodies capable of selectively binding to mutant proteins be employed. In particular, an assay using a plurality of monoclonal antibodies, each capable of binding to a mutant epitope, may be employed. The levels of anti-mutant antibody binding in a sample obtained from a test subject (visualized by, for example, radiolabelling, ELISA or chemiluminescence) may be compared to the levels of binding to a control sample. Such antibody diagnostics may be used for in situ immunohistochemistry using biopsy samples of retinal tissues obtained antemortem or postmortem.

When the diagnostic assay is to be based upon nucleic acids from a tissue sample, either mRNA or genomic DNA may be used. When mRNA is used from a sample, many of the same considerations apply with respect to source tissues and the possibility of alternative splicing. That is, there may be little or no expression of transcripts unless appropriate tissue sources are chosen or available, and alternative splicing may result in the loss of some information. With either mRNA or DNA, standard methods well known in the art may be used to detect the presence of a particular sequence either in situ or in vitro (see, e.g. Sambrook et al., eds. (1989) Molecular Cloning: A Laboratory Manual, Cold Spring Harbor Press, Cold Spring Harbor, N.Y.).

For in situ detection of a mutant FIBL-6, or other FIBL-6-related nucleic acid sequence, a sample of tissue, which can include skin, may be prepared by standard techniques and then contacted with a probe, preferably one which is labelled to facilitate detection, and an assay for nucleic acid hybridization is conducted under stringent conditions which permit hybridization only between the probe and highly or perfectly complementary sequences. Because the FIBL-6 mutation detected to date consists of a single nucleotide substitution, high stringency hybridization conditions will be required to distinguish normal sequences from most mutant sequences. As an example only, the following procedure may be employed on a subject: A rat animal model is anesthetized and transcardially perfused with cold PBS, followed by perfusion with a formaldehyde solution. The tissue of interest is then removed, frozen in liquid nitrogen, and cut into thin micron sections. The sections are placed on slides and incubated in proteinase K. Following rinsing in DEP, water and ethanol, the slides are placed in prehybridization buffer. A radioactive probe corresponding to the selected oligonucleotide is incubated with the sectioned tissue. After incubation and air drying, the labeled areas are visualized by autoradiography. Dark spots on the tissue sample indicate hybridization of the probe with tissue mRNA, demonstrating expression of the nucleic acid sequence.

A significant advantage of the use of either DNA or mRNA is the ability to amplify the amount of genetic material using the polymerase chain reaction (PCR), either alone (with genomic DNA) or in combination with reverse transcription (with mRNA to produce cDNA). It is contemplated that such PCR-based genetic methods may be preferred commercial embodiments for diagnostic screenings.

Screening for AMD Linked to Chromosome 1q

Screening for AMD as linked to chromosome 1q may now be readily carried out because of the knowledge of a mutation in the gene provided by this invention.

Individuals with a high risk for AMD (present in family pedigree), or individuals not previously known to be at risk, or people in general may be screened routinely using probes to detect the presence of a mutant FIBL-6 gene by a variety of techniques. Genomic DNA used for the diagnosis may be obtained from body cells, such as those present in the blood, tissue biopsy, surgical specimen, or autopsy material. The DNA may be isolated and used directly for detection of a specific sequence or may be PCR amplified prior to analysis. RNA or cDNA may also be used. To detect a specific nucleic acid sequence, hybridization using specific oligonucleotides, direct nucleotide sequencing, restriction enzyme digest, RNase protection, chemical cleavage, or ligase-mediated detection may be used. Oligonucleotides specific to mutant sequences can be chemically synthesized and labelled radioactively with isotopes, or non-radioactively using biotin tags, and hybridized to individual samples immobilized on membranes or other solid supports by dot-blot or transfer from gels after electrophoresis. The presence or absence of these mutant sequences is then visualized using methods such as autoradiography, fluorometry, or colorimetric reaction. Examples of suitable PCR primers which are useful for example in amplifying portions of the subject sequence containing the aforementioned mutations are set out in the Examples. Direct DNA sequencing reveals sequence differences between normal and mutant FIBL-6 DNA. Cloned genomic or cDNA segments may be used as probes to detect specific DNA segments. PCR can be used to enhance the sensitivity of this method. PCR, which is well-known in the art, is an enzymatic amplification directed by sequence-specific primers, and involves repeated cycles of heat denaturation of the DNA, annealing of the complementary primers and extension of the annealed primer with a DNA polymerase. This results in an exponential increase of the target DNA.

Other nucleotide sequence amplification techniques may be used, such as ligation-mediated PCR, anchored PCR and enzymatic amplification as will be understood by those skilled in the art.

Sequence alterations may also generate restriction enzyme recognition sites which are revealed by the use of appropriate enzyme digestion followed by gel-blot hybridization. DNA fragments carrying the site (normal or mutant) are detected by their increase or reduction in size, or by the increase or decrease of corresponding restriction fragment numbers. Genomic DNA samples may also be amplified by PCR prior to treatment with the appropriate restriction enzyme and the fragments of different sizes are visualized, for example under UV light in the presence of ethidium bromide, after gel electrophoresis.

Genetic testing based on DNA sequence differences may be achieved by detection of alteration in electrophoretic mobility of DNA fragments in gels. Small sequence deletions and insertions can be visualized by high resolution gel electrophoresis of single stranded DNA, or as changes in the migration pattern of DNA heteroduplexes in non-denaturing gel electrophoresis. Alternatively, a single base substitution mutation may be detected based on differential PCR product length in PCR. The PCR products of the normal and mutant gene may be differentially detected in acrylamide gels.

Nuclease protection assays (SI or ligase-mediated) also reveal sequence changes at specific locations.

Alternatively, to confirm or detect a polymorphism, ligated PCR, ASO, REF-SSCP chemical cleavage, endonuclease cleavage at mismatch sites or SSCP may be used. Both REF-SSCP and SSCP are mobility shift assays which are based upon the change in conformation due to mutations.

DNA fragments may also be visualized by methods in which the individual DNA samples are not immobilized on membranes. The probe and target sequences may be in solution or the probe sequence may be immobilized. Autoradiography, radioactive decay, spectrophotometry and fluorometry may also be used to identify specific individual genotypes. Mutations can also be detected by direct nucleotide sequencing.

According to an embodiment of the invention, the portion of the cDNA or genomic DNA segment that is informative for a mutation can be amplified using PCR. For example, the DNA segment immediately surrounding the Gln5345Arg mutation acquired from any cell sample from an individual, such as RPE, epithelial cell, can be screened using the oligonucleotide primers SEQ ID NO:3 and SEQ ID NO:4. This region would then be amplified by PCR, the products separated by electrophoresis, and transferred to membrane. Normal and mutant PCR products may then be detected using, for example, hybridization of labeled oligonucleotide probes and autoradiography, RFLP analysis, or direct sequencing. In inherited cases, as the primary event, and in non-inherited cases as a secondary event due to the disease state, abnormal processing of FIBL-6 or proteins reacting with FIBL-6 may occur. This can be detected as abnormal phosphorylation, glycosylation, glycation amidation, or proteolytic cleavage products in body tissues or fluids.

Diagnosis of non-inherited cases also can be made by observation of alterations in the FIBL-6 transcription, translation, and post-translational modification and processing as well as alterations in the intracellular and extracellular trafficking of FIBL-6 gene products in the RPE or epithelial cells. Such changes will include alterations in the amount of FIBL-6 messenger RNA and/or protein, alteration in phosphorylation state, abnormal intracellular location/distribution, abnormal extracellular distribution, etc. Such assays will include: Northern Blots (with FIBL-6-specific and non-specific nucleotide probes which also cross-react with other members of the gene family), and Western blots and enzyme-linked immunosorbent assays (ELISA) (with antibodies raised specifically to: a FIBL-6; to various functional domains of a FIBL-6; to other members of the homologous gene family; and to various post-translational modification states including glycosylated and phosphorylated isoforms). These assays can be performed on peripheral tissues (e.g. skin, blood cells, plasma, cultured or other fibroblast tissues, etc.) as well as on biopsies of retinal tissues obtained antemortem or postmortem. Such assays might also include in situ hybridization and immunohistochemistry to localized messenger RNA and protein to specific subcellular compartments and/or within structures associated with these diseases.

In accordance with the present invention, diagnostic kits are also provided which will include the reagents necessary for the above-described diagnostic screens. For example, kits may be provided which include antibodies or sets of antibodies which are specific to one or more mutant epitopes. These antibodies may, in particular, be labelled by any of the standard means which facilitate visualization of binding. Alternatively, kits may be provided in which oligonucleotide probes or PCR primers are present for the detection and/or amplification of mutant FIBL-6, and other FIBL-6-related nucleotide sequences. Again, such probes may be labelled for easier detection of specific hybridization. As appropriate to the various diagnostic embodiments described above, the oligonucleotide probes or antibodies in such kits may be immobilized to substrates and appropriate controls may be provided. Examples of such probes include oligonucleotides comprising or consisting of at least one of SEQ ID NO:7, SEQ ID NO:8. SEQ ID NO:12-94, and SEQ ID NO:95-177.

Therapies

An important aspect of the biochemical studies using the genetic information of this invention is the development of therapies to circumvent or overcome the FIBL-6 gene defect, and thus prevent, treat, control serious symptoms or cure the disease. AMD manifests itself as a vision-related disorder which in one of its forms is associated with an inherited mutation in a FIBL-6 gene.

Protein Therapy

Treatment of AMD can be performed by replacing the mutant protein with normal protein, or by modulating the function of the mutant protein. Once the biological pathway of the involved FIBL-6 protein has been completely understood, it may also be possible to modify the pathophysiologic pathway or pathways (e.g. a signal transduction pathway) in which the protein participates, in order to correct the physiological defect.

To replace the mutant protein with normal protein, or with a protein bearing a deliberate counterbalancing mutation, it is necessary to obtain large amounts of pure FIBL-6 protein from cultured cell systems which can express the protein. Delivery of the protein to the affected eye tissue or other tissues can then be accomplished using appropriate packaging or administrating systems.

Gene Therapy

Gene therapy is another potential therapeutic approach in which normal copies of the FIBL-6 gene are introduced into patients to code successfully for normal protein in affected cell types. The gene must be delivered to those cells in a form in which it can be taken up and code for sufficient protein to provide effective function. Alternatively, in some mutants it has been possible to prevent disease by introducing another copy of the homologous gene bearing a second mutation in that gene or to alter the mutation, or use another gene to block its effect.

Retroviral vectors can be used for somatic cell gene therapy especially because of their high efficiency of infection and stable integration and expression. The targeted cells however must be able to divide and the expression levels of normal protein should be high enough to achieve the desired effect. The full length FIBL-6 gene can be cloned into a retroviral vector and driven from its endogenous promoter or from the retroviral long terminal repeat or from a promoter specific for the target cell type of interest. Other viral vectors which can be used include adeno-associated virus, vaccinia virus, bovine papilloma virus, or a herpes virus such as Epstein-Barr virus.

Gene transfer could also be achieved using non-viral means requiring infection in vitro. This would include calcium phosphate, DEAE dextran, electroporation, and protoplast fusion. Liposomes may also be potentially beneficial for delivery of DNA into a cell. Although these methods are available, many of these are of lower efficiency.

Antisense based strategies can be employed to explore FIBL-6 gene function and as a basis for therapeutic drug design. The principle is based on the hypothesis that sequence-specific suppression of gene expression can be achieved by intracellular hybridization between mRNA and a complementary antisense species. The formation of a hybrid RNA duplex may then interfere with the processing, transport, translation, and/or stability of the target FIBL-6 mRNA. Hybridization is required for the antisense effect to occur, but the efficiency of intracellular hybridization can be low and therefore the consequences of such an event may not be very successful. Antisense strategies may use a variety of approaches including the use of antisense oligonucleotides, injection of antisense RNA and transfection of antisense RNA expression vectors. Antisense effects can be induced by control (sense) sequences, however, the extent of phenotypic changes are highly variable. Phenotypic effects induced by antisense effects are based on changes in criteria such as protein levels, protein activity measurement, and target mRNA levels.

Transplantation of normal genes into the affected area of the patient can be useful therapy for AMD. In this procedure, a normal human FIBL-6 gene is transferred into a cultivatable cell type, either exogenously or endogenously to the patient. These cells are then injected serotologically into the disease-affected tissue or tissues.

Immunotherapy is also possible for AMD. Antibodies are raised to a mutant FIBL-6 protein (or a portion thereof) and are administered to the patient to bind or block the mutant protein and prevent its deleterious effects. Simultaneously, expression of the normal protein product could be encouraged. Alternatively, antibodies are raised to specific complexes between mutant or wild-type FIBL-6 and their interaction partners.

A further approach is to stimulate endogenous antibody production to the desired antigen. Administration could be in the form of a one time immunogenic preparation or vaccine immunization. An immunogenic composition may be prepared as injectables, as liquid solutions or emulsions. The FIBL-6 or antigen-may be mixed with pharmaceutically acceptable excipients compatible with the protein. Such excipients may include water, saline, dextrose, glycerol, ethanol and combinations thereof. The immunogenic composition and vaccine may further contain auxiliary substances such as emulsifying agents or adjuvants to enhance effectiveness. Immunogenic compositions and vaccines may be administered parenterally by injection subcutaneously or intramuscularly.

The immunogenic preparations and vaccines are administered in such amount as will be therapeutically effective, protective and immunogenic. Dosage depends on the route of administration and will vary according to the size of the host.

The above disclosure generally describes the present invention. A more complete understanding can be obtained by reference to the following specific examples. These examples are described solely for purposes of illustration and are not intended to limit the scope of the invention. Changes in the form and substitution of equivalents are contemplated as circumstances may suggest or render expedient. Although specific terms have been employed herein, such terms are intended in a descriptive sense and not for purposes of limitation.

EXAMPLE 1

Identification of a Family Carrying an AMD-Associated Gene

Clinical Information

Twenty-one individuals from a family with AMD agreed to participate in the original study, which was approved by the Institutional Review Board of Oregon Health Sciences University, Portland. For all but one individual, stereoscopic fundus photographs of the macula of both eyes were obtained. For the remaining individual, now deceased, the eyes were retrieved for histopathologic analysis. Clinical information, including visual acuity, was obtained for all affected individuals. In most instances, this information was obtained from the individual's local ophthalmologist or optometrist, and fundus photographs were taken at a local retina facility.

Classification of AMD

Stereoscopic fundus photographs of the macula were classified using a modified version of the Wisconsin Age-Related Maculopathy Grading System. Each eye was classified independently by three ophthalmologists without knowledge of the patient's genotype. Disagreements were adjudicated among the three graders. The patient's classification was based on the eye with the more advanced AMD.

The following classification system was used: Group 1, definite AMD is characterized by exudative AMD (choroidal neovascularization, pigment epithelial detachment, or disciform macular scar) or geographic atrophy (area, >175 µm). Group 2, probably AMD, is characterized by the presence of large drusen (>125 µm) within 3000 µm of the fovea, with total cumulative drusen area exceeding 393,744 µm$^2$ (approximating the area within a 700-µm diameter circle). Nongeographic pigment atrophy and focal hyperpigmentation may or may not be present, and the features present in group 1 are absent. Group 3, probably no AMD, is characterized by large drusen present (>125 µm), but the cumulative area is less in extent than in group 2. Group 3 is characterized by the absence of exudative AMD, geographic or nongeographic pigment atrophy, and local hyperpigmentation. Group 4, no AMD, is characterized by no large drusen (>125 µm), geographic or nongeographic pigment atrophy, focal hyperpigmentation, or exudative maculopathy. Group 5, uncertain, is characterized by absence of features seen in groups 1 and 2 and presence of any of the following: extensive small (<63 µm) or intermediate (63-125 µm) drusen, nongeographic pigment atrophy, or focal hyperpigmentation, or factors preventing reliable classification, such as media opacities, concomitant retinal disease, or pigment epithelial disturbance, with or without large drusen (>125 µm).

The definition of group 2 was based on findings demonstrating a 19-fold increase in the probability of developing late AMD (group 1) for eyes with large drusen (>125 µm) and a minimum cumulative drusen area of 393,744 µm (equivalent to an approximately 700-µm diameter circle) located within 3,000 µm of the fovea. Eyes classified as group 5, uncertain, are those in which accompanying conditions preclude accurate classification of AMD or eyes that contain possible risk factors for the later development of late AMD, including extensive small and intermediate drusen (<125 µm) or pigment epithelial abnormalities.

For purposes of linkage analysis, groups 1 and 2 were classified as affected and groups 3 and 4 were classified as unaffected. Those categorized as group 5 were classified as unknowns in the linkage analysis.

Genotyping

Genomic DNA was extracted from the blood of family members using a kit from Epicentre Technologies (Madison, Wis.) according to their directions and was quantitiated spectrophotometrically. Three pools of DNA were created. The first pool consisted of equimolar amounts of DNA from eight affected family members (patients 1009, 2101, 1011, 1015, 1007, 2705, 1017, and 2005). The second pool was similarly derived from four unaffected family members (patients 2009, 2502, 2011, and 2103). These pools represented all affected and unaffected individuals who had been ascertained as the pooling was initiated. A third pool consisted of equimolar amounts of DNA from eight unrelated individuals. Three affected cousins from the family with AMD (patients 2101, 2705, and 2005) were also individually genotyped. 615 polymorphic microsatellite repeat markers at an average density of six centimorgans (cM) were used to genotype DNA from the three selected individuals and the three DNA pools. 572 of these markers yielded clearly identifiable banding patterns. After the initial pooled genome-wide screen, markers from areas most suggestive of shared chromosomal segments were used to genotype all potentially informative family members. One region showing positive linkage was then mapped at an average marker density of 0.5 cM.

Linkage Analysis

Two-point linkage between the disease locus and each microsatellite marker locus was tested by the parametric lodscore method using a computer program (MLINK). Frequencies of the disease allele and of the normal alleles were assumed to be 0.001 and 0.999, respectively. Based on the pedigree in which there were 3 generations of affected individuals, and male-to-male transmission, an autosomal-dominant mode of inheritance was assumed. Family members were placed in 1 of 5 age-related liability classes. Age-dependent penetrances for these classes were set to 0.001 (<50 years), 0.01 (50-54 years), 0.09 (55-64 years), 0.42 (65-74 years), and 0.95 (>75 years). These values were determined from a set of 20 similar families with AMD that the inventors identified and are comparable with the prevalence observations reported in three studies based on approximately 15,000 individuals. Allele frequencies reported by the Centre d'Etudes du Polymorphisme Humain (CEPH), Paris, France, were used except for markers D15191, D15202, D15461, D15492, and D15412, which were measured in a set of 92 unrelated individuals. Markers for multipoint linkage analysis, whose order was statistically supported, were identified using genotypes from CEPH pedigrees and the computer programs CRI-MAP and MultiMap. Multipoint linkage analysis was conducted using the VITESSE algorithm.

EXAMPLE 2

Screening Family for AMD-Associated Mutation

Subject Ascertainment

Human subjects were informed and consented as mandated by the Institutional Review Board of Oregon Health & Science University. Approximately 20 ml of blood was collected from each subject and DNA was extracted by standard techniques. In total, 100 families with three or more members affected with AMD, 188 sporadic cases of AMD, and 174 phenotypically normal individuals were studied. The diagnosis of AMD was based upon stereoscopic fundus photographs as previously described. (Klein M L, *Arch Ophthalmol* 116:1082-8, 1998.)

Mutation Screening

Two monoallelic strains (human-mouse cell hybrids), derived from proband 111-3 of family A, were generated by GMP Genetics, Inc. (Waltham, Mass.). One carried the ARMD1 region corresponding to the disease haplotype and the other, a presumably non-disease sequence. Inclusion of the ARMD1 gene locus in the hybrids was verified in the laboratory by genotyping with six microsatellite markers. Exons were mapped on genomic sequence through a pair-wise comparison of XM_053531, the reference sequence for FIBL-6 mRNA, with contigs AL121996, AL13S796, AL133515, AL391824, AL118512, AL135797, and AL133553. Primers were designed to amplify each exon plus an additional 50-100 basepairs of the adjacent introns using the Primer3 software package. Genomic DNA (25 ng) was amplified in 20 µl reactions using FastStart Taq DNA polymerase (Roche Diagnostic Corporation Indianapolis, Ind.) with a balcony PCR protocol, which helped to prevent amplification of homologous mouse DNA. All amplifications included an initial denaturation at 95° C. for 5 minutes, a 30-second denaturation at 95° C., an annealing step, and a 1-minute extension at 72° C. "Balcony" refers to the first 10 cycles, in which annealing was performed at 5° C. above the $T_m$ of the primers as determined by Primer3 software. This was followed by a 20 cycle touchdown phase in which the annealing temperature dropped in 0.50° C. increments from 5° C. above the primer $T_m$ to 5° C. below. The final phase consisted of 25 cycles in which annealing occurred at 5° C. below primer $T_m$ PCR products were electrophoresed on 2% agarose gels, excised, purified with Microcon-PCR Filter units (Millipore Corporation, Bedford, Mass.), and sequenced at the Veteran's Administration Core Sequencing facility (Portland, Oreg.).

Control subjects (n=174), sporadic AMD cases (n=188), and family members (n=1016) were assayed for the Gln5345Arg variation by DHPLC (Transgenomics, Omaha, Nebr.) or by ASO hybridization or both. For DHPLC, a 194 bp PCR product, located within exon 104 of FIBL-6, was amplified using the forward primer, 5'CCGTGCAAGGT-TATAGCTACTG3' (SEQ ID NO:3), and the reverse primer, 5'ATGGCATACGAGCAGACATT3' (SEQ ID NO:4). In order to increase the sensitivity of detecting potential homozygous mutations, samples were mixed 1:1 with wild-type product prior to a final 5-minute denaturation and slow reannealing step. For ASO hybridization, a 462 bp product was amplified using the forward primer, 5'TATCATGGCAT-ACGAGCAGAC3' (SEQ ID NO:5), and the reverse primer, 5'TTCACTGCACTCAAACAATCAC3' (SEQ ID NO:6). Blotting and hybridization were performed as previously described, Litt M, Kramer P, LaMorticella D M, Murphey W, Lovrien E W, Weleber R G, *Hum Mol Genet* 7:471-4, 1998, except that blots were probed at 47° C. overnight with a 17 base wildtype oligomer (16,263A), 5'ACCAGGACAA-CATTTAT3' (SEQ ID NO:7), or mutant oligomer (16, 263G), 5'ACCAGGACGACATTTAT3' (SEQ ID NO:8).

RT-PCR of Human Cell Lines

Human RPE cells and skin fibroblasts were cultured as previously detailed. Alexander J P, Bradley J M B, Gabourel J D, Acott T S, *Investigative Ophthalmology & Visual Science* 31:2520-8, 1990; Vranka J A, *Current Eye Research* 16:102-110, 1997; Alexander J P, Samples J R, Van Buskirk E M, Acott T S, *Investigative Ophthalmology & Visual Science* 32:172-80, 1991. Total RNA was extracted from cultured cells and various human ocular tissues using an RNAqueous kit (Ambion). RT-PCR utilized an RNA Amplification kit (Roche) in a Roche LightCycler with detection after each cycle based on SybrGreen binding. Two sets of primers were used to differentiate alternative splicing involving exon 104. A common upstream primer, 5'-CAA-GAAGCAGCTATCGTTGTG-3' (SEQ ID NO:9), was located approximately 100 bp proximal to the 3' end of exon 103. One downstream primer, 5'-ACTGTCTGTAATGCT-GTTGAGGT-3' (SEQ ID NO:10), was located within exon 104 and produced a 297 bp PCR product when exon 104 was present in the transcript. The other primer, 5'-GCAT-GTCTTTCCATTGTGTGT-3' (SEQ ID NO:11), was located approximately 100 bp downstream of the 5' end of exon 105 and yielded products of 536 bp or 185 bp depending on the presence or absence of exon 104 in the transcript. Several resultant PCR products were gel-purified and sequenced for further verification.

Sequencing of Additional Species

*Oryctolagus cuniculus* cDNA was obtained from the Casey Eye Institute, Oregon Health & Science University (OHSU). *Canis familiaris, Felis catus, Ovis* sp., and *Rattus norvegicus* blood was obtained from the Department of Comparative Medicine, OHSU. A chicken cell line was obtained from the Pathology Department, OHSU. Porcine tissues were obtained from Carlton Packing (Carlton, Oreg.). Three sets of primers were designed to the most conserved regions between mouse and human copies of exon 104 of FIBL-6 that included the Gln5345 codon. Amplifications used less stringent conditions than normal to compensate for potential non-complementarity between primers and template. An initial, "touchup" phase of PCR included 8-20 cycles, in which the annealing temperature was raised incrementally from 10-15° C. below the primer $T_m$ to 5-10° C. below. This was followed by 25 cycles of PCR in which annealing occurred at 5-10° C. below the primer $T_m$. The magnesium concentration was also increased to 2-4 mM. If the initial PCR product was weak or not unique, the amplification was repeated with a 1:1000 dilution of product as template under normal stringent conditions (annealing at 5° C. below $T_m$, 1.5 mM magnesium concentration).

Figure 3:
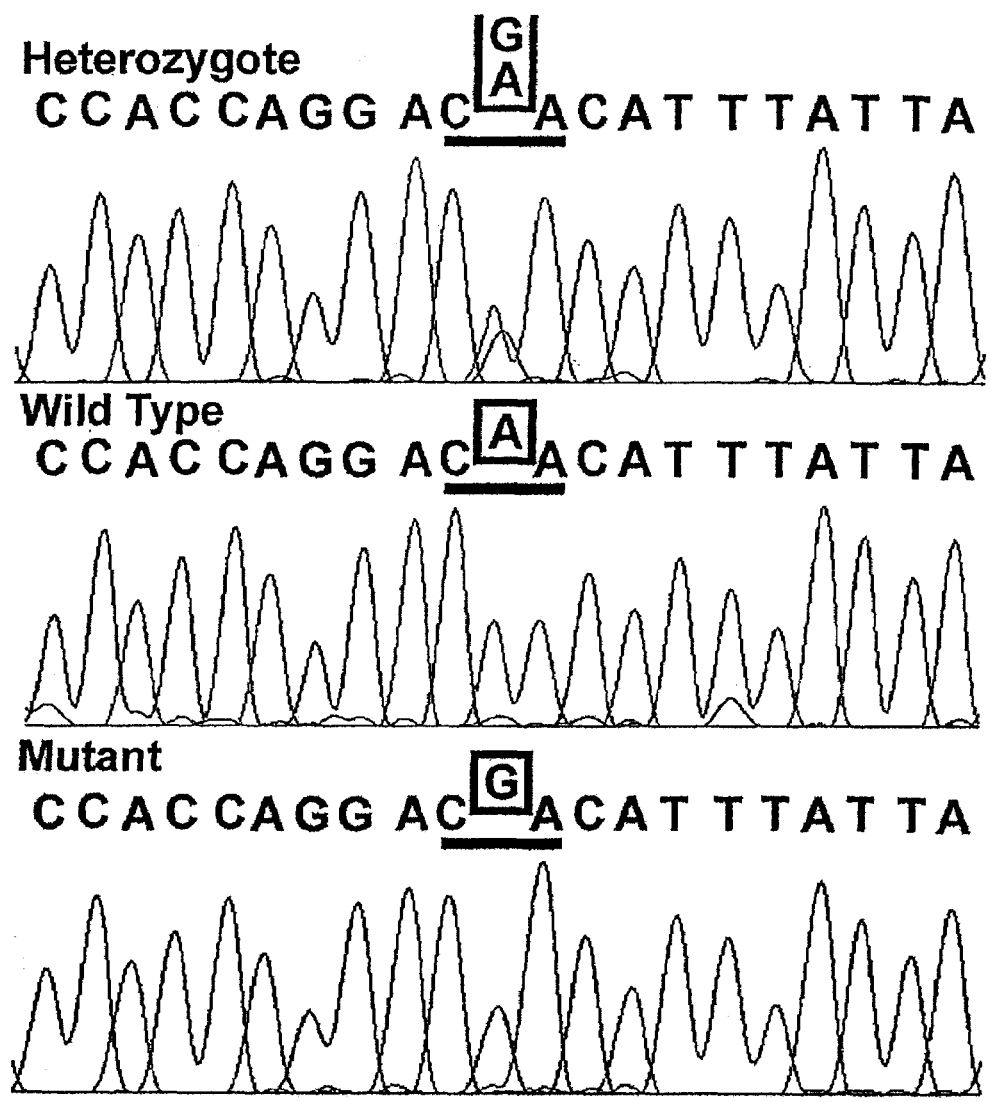
FIG. 3. Chromatograms of fluorescent dye-terminator sequencing of PCR products of FIBL-6 demonstrating an A→G change (boxed) at the second nucleotide of codon 5345, which is expected to produce the Gln5345Arg change. Heterozygote: both chromosomes of the proband (III-3) of family A. Wildtype: paternal chromosome of III-3. Mutant: maternal chromosome of III-3.

According to this Example, a potential disease-causing variation (A16,263G) in exon 104 of FIBL-6 was identified by comparing the DNA sequence of two monoallelic clones (Yan H, *Nature* 403:723-4, 2000) obtained from the proband (III-3) of family A (FIG. 3). This sequence variation is expected to change the glutamine at amino acid position 5345 of FIBL-6 to arginine (Gln5345Arg). Since this was a non-conservative amino acid substitution, DNA from all the members of family A was sequenced to determine if the variation segregated with the disease haplotype.

The Gln5345Arg variation segregated exclusively with the disease locus in family A (FIG. 4). It is not associated with any of the seventeen other haplotypes across the ARMD1 region found in this pedigree. DNA sequencing revealed that all sixteen family members who carried the disease haplotype also carried the Gln5345Arg variation, including the ten affected. members described previously. Klein M L, *Arch Ophthalmol* 116:1082-8, 1998. Furthermore, none of the eleven family members who lack the disease haplotype carried the variation.

The glutamine at position 5345 of FIBL-6 appears to be conserved among eutherian species. Since the only other FIBL-6 mammalian DNA sequence deposited at Genbank belonged to mouse, a region was sequenced corresponding to a portion of human exon 104 in pig, rabbit, dog, rat, cat, sheep, and chicken. In all mammals assayed and in chicken, the amino acid at a position equivalent to 5345 in human FIBL-6 was conserved as glutamine (FIG. 2). There was approximately 85% conservation at the nucleotide level and approximately 90% conservation at the amino acid level among all mammalian species in the portion of the cbEGF domain in exon 104 sequenced. In mouse and rabbit, this glutamine is encoded by a CAG codon instead of the CAA codon found in other species.

In an initial DHPLC screen of a single affected member from 100 AMD families, we identified the Gln5345Arg variation in two additional pedigrees, families B and C. Sequencing of DNA from all the family members showed that the variation does not segregate with AMD in either family (FIG. 5). However, in both families, the Gln5345Arg variation segregated with a haplotype that was inherited apparently from the spouse (II-4 and II-1 in families B and C, respectively) of a family member. An ASO hybridization screen of all 1016 affected and unaffected family members identified only one additional person with the Gln5345Arg variation. This affected individual, II-4 in family D, also has a unique haplotype across this region that is not shared by any other members of his family (FIG. 5).

Individuals from all four families who carry the Gln5345Arg variation share a unique haplotype that overlaps the FIBL-6 gene. They all have in common an allele of six contiguous markers in the region of FIBL-6 (FIG. 5). Furthermore, three families (A, B, and D) share an allele of an additional four contiguous markers (D1S2138, D1S3460, D1S202, and D1S1642) distal to these for a total of ten. Families C and D also share three contiguous markers (D1S2127, D1S2701, and D1S158) proximal to these six.

Additionally, 2 of 348 chromosomes from control subjects and 1 of 376 chromosomes from sporadic AMD cases were found to harbor the Gln5345Arg variation by DHPLC and ASO hybridization. While the sporadic case was 74 years of age at the time of ascertainment, the control subjects were only 57 and 64 years of age. The 64-year old control subject has a scar in the macula of her left eye. In order to assay for additional variations that may mitigate the effect of the Gln5345Arg variation, all 107 exons of FIBL-6 from both control subjects were sequenced. The 57-year-old control subject was found to harbor five of the twelve variations detected in the exons of FIBL-6. One of these was further investigate, as described below. Although haplotypes are yet to be assigned, the genotypes of these three individuals suggest that the Gln5345Arg variation is associated with the same unique haplotype that is found in all four families (FIG. 5).

Few variations were identified among the 16,905 nucleotides and 5,635 amino acid residues that encode FIBL-6. All 107 exons were sequenced in DNA from seven individuals, representing 12 unique copies of FIBL-6. In addition to the Gln5345Arg change, only one other alteration from the NCBI reference sequence (XM_05353 1) was detected in the proband (111-3) from family A. This was an insertion of 11 bp between the fifth and sixth bases of exon 31. However, this homozygous insertion was also detected in five additional members of family A, 12 unrelated control subjects, and 3 additional individuals. This insertion improves a presumably unusable acceptor site to a potentially functional one. Therefore, the insertion may better represent the genomic sequence contained in AL118512. Four synonymous (C5086T, C7600T, C13216T, and C16852G) and seven non-synonymous (Ala1624Val, Met2327Ile, Ile2418Thr, Glu2893Gly, His4084Tyr, Asp5087Val, and Arg5188His) changes were found in addition to the Gln5345Arg variation. The Ile2418Thr change, present in the 57-year old control subject, was further investigated by DHPLC. However, because this change was present in 43 of 348 chromosomes from control subjects, it appears to be a common polymorphism.

Figure 6:
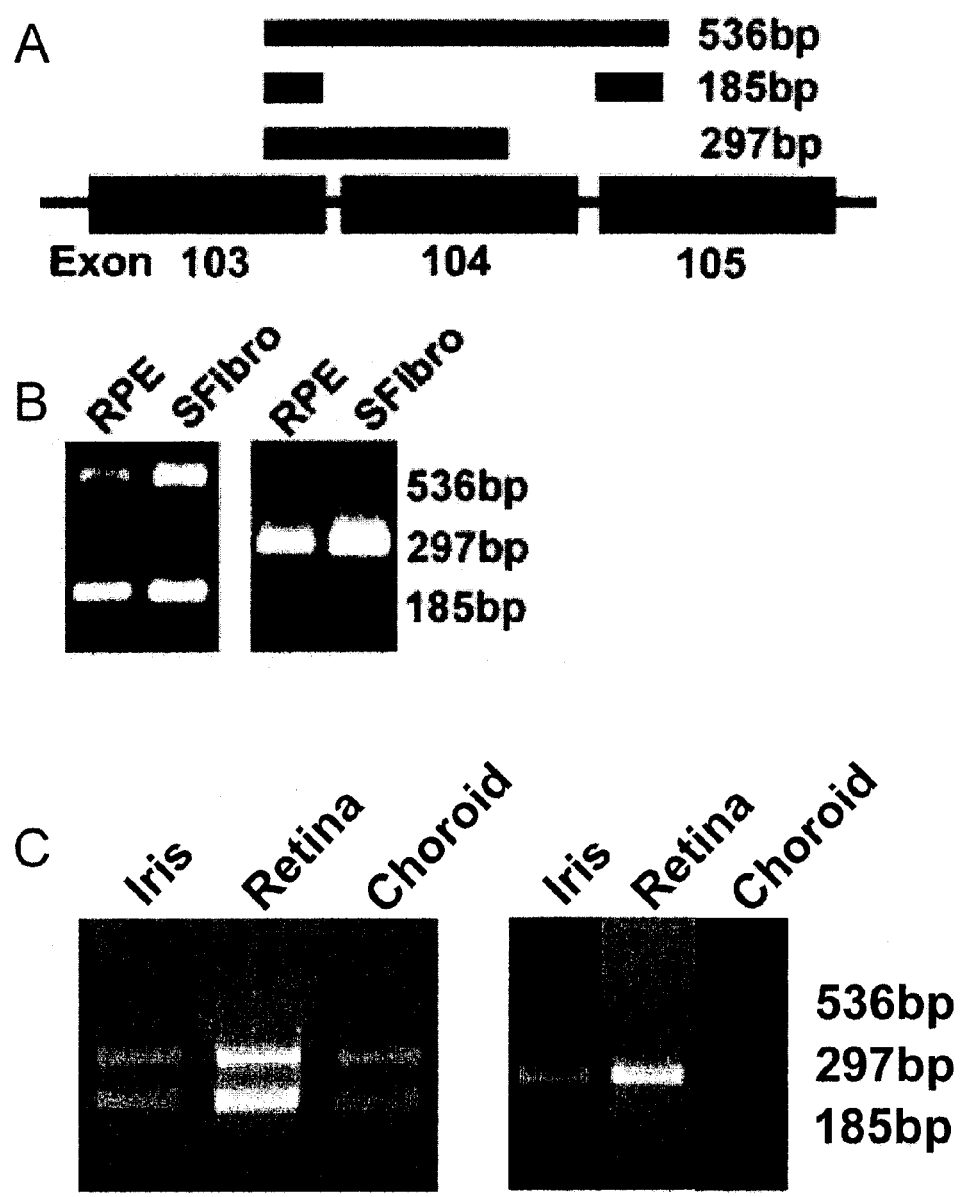
FIG. 6. FIBL-6 expression and alternative splicing of exon 104. A. Upper two sets of bars represent PCR amplicons obtained with 5' primer in exon 103 and 3' primer in exon 105 (left-hand panels in B and C; 185 bp product indicates absence of exon 104); lower bar represents amplicon obtained with identical 5' primer but with 3' primer in exon 104 (right-hand panels in B and C). B. Expression in RPE cells and skin fibroblasts. C. Expression in iris, retina, and choroid tissue.

RT-PCR was used to determine if FIBL-6 is expressed in the retina (FIG. 6). Two previously identified clones (AL833232 & AK027344), corresponding to the 3' end of FIBL-6, lacked exon 104, in which the Gln5345Arg variation occurs. Furthermore, intron 103 has a poor acceptor site compared to the consensus sequence for splicing. Therefore, gene-specific primers were designed that bridged or terminated in exon 104. RT-PCR analysis demonstrated FIBL-6mRNA in human skin fibroblasts, RPE cells, retina, iris, and choroid. Alternative splicing of exon 104 occurred in FIBL-6 transcripts from all tissues examined (FIG. 6).

Although the foregoing invention has been described in some detail by way of illustration and examples for purposes of clarity and understanding, it will be apparent to those skilled in the art that certain changes and modifications may be practiced without departing from the spirit and scope of the invention. Therefore, the description should not be construed as limiting the scope of the invention, which is delineated by the appended claims.

All publications, patents and patent applications cited herein are hereby incorporated by reference in their entirety for all purposes to the same extent as if each individual publication, patent and patent application were specifically and individually indicated to be so incorporated by reference.

What is claimed is:

1. A method of determining whether a human subject is at risk for development of macular degeneration, the method comprising the steps of: (a) obtaining a nucleic acid sample from the human subject; (b) conducting an assay on the nucleic acid sample to determine the presence or absence of a mutation of a polynucleotide sequence set forth as SEQ ID NO: 1, the mutation being a substitution of at least one base of the codon at position 16,262, 16,263 and 16,264 wherein the mutated codon encodes glutamine; and (c) correlating the presence of the mutation with the risk of developing macular degeneration, wherein the presence of the mutation determines that the human subject is at risk for development of macular degeneration.

2. The method of claim 1, wherein the assay is selected from the group consisting of probe hybridization, direct sequencing, restriction enzyme fragmentation and fragment electrophoretic mobility.

3. The method of claim 1 wherein the nucleic acid sample is an RNA sample and the assay is a direct sequencing assay.

4. The method of claim 3, wherein the assay comprises the steps of: (a) reverse transcribing the RNA sample to produce a corresponding cDNA; (b) performing at least one polymerase chain reaction with suitable oligonucleotide primers to amplify the polynueleotide sequence set forth as SEQ ID NO: 1; (c) obtaining the nucleotide sequence of amplified polynucleotide; and (d) determining the presence or absence of the substitution of at least one base of the codon at position 16,262, 16,263 and 16,264 of the polynueleotide sequence set forth as SEQ ID NO: 1 wherein the codon encodes arginine.

5. The method of claim 1 wherein the nucleic acid sample is a DNA sample.

6. The method of claim 3 wherein the DNA sample is a genomic DNA sample and the assay comprises the steps of: (a) amplifying a target portion of the nucleotide sequence of the genomic DNA; (b) obtaining the nucleotide sequence of said amplified portion; (c) determining the presence or absence of the substitution of at least one base of the codon at position 16,262, 16,263 and 16,264 wherein the codon encodes arginine in said target portion nucleotide sequence.

7. A method for confirming a diagnosis of acute macular degeneration in a human subject, comprising (a) obtaining a nucleic acid sample from the human subject; (b) conducting an assay on the nucleic acid sample to determine the presence or absence of a polynucleotide encoding a polypeptide sequence set forth as SEQ ID NO: 2, wherein arginine at position 5345 is substituted by a glutamine; and (c) correlating the presence of a polynucleotide encoding a polypeptide sequence set forth as SEQ ID NO: 2, wherein arginine at position 5345 is substituted for a glutamine with the presence of acute macular degeneration, thereby confirming the diagnosis of acute macular degeneration in the human subject.

8. The method of claim 7, wherein the nucleic acid sample is an RNA sample and the assay is a direct sequencing assay.

9. The method of claim 7, wherein the nucleic acid sample is a DNA sample.

10. The method of claim 7, wherein the nucleic acid sample is a genomic DNA sample and the assay comprises the steps of: (a) amplifying a target portion of the nucleotide sequence of the genomic DNA; (b) obtaining the nucleotide sequence of said amplified target portion; and (c) determining the presence or absence of a polynucleotide encoding a polypeptide sequence set forth as SEQ ID NO: 2, wherein arginine at position 5345 is substituted for a glutamine is correlated with the presence of acute macular degeneration.

11. The method of claim 1, wherein the sample comprises a blood sample.

12. The method of claim 7, wherein the sample comprises a blood sample.

13. The method of claim 7, wherein the diagnosis comprises analysis of stereoscopic photographs of the macula.

* * * * *

SEQUENCE LISTING

```
<160> NUMBER OF SEQ ID NOS: 186

<210> SEQ ID NO 1
<211> LENGTH: 18206
<212> TYPE: DNA
<213> ORGANISM: Homo sapiens
<220> FEATURE:
<221> NAME/KEY: CDS
<222> LOCATION: (230)...(17137)
<220> FEATURE:
<221> NAME/KEY: variation
<222> LOCATION: (14197)...(14197)
<223> OTHER INFORMATION: A and G allelic variation exists at this
      position
<220> FEATURE:
<221> NAME/KEY: variation
<222> LOCATION: (17811)...(17811)
<223> OTHER INFORMATION: C and T allelic variation exists at this
      position

<400> SEQUENCE: 1
gaagccgcat ccagacaaaa gctgccgcat ccctgccctg cccaacccct ggagggattc     60
gagtttggtg cttgtccccg tctgattctc agcgccaaac ttttttgctag ttcagagatt   120 ccaagagtct gatgagttac tctgagagga aaccctctgc ctgttgttga ggaggactga   180
gcacagtgct taggcgctga gggggaaaaa gagggggaaa aaaaagaaa atg att tcc    238
                                                      Met Ile Ser
                                                        1 tgg gaa gtt gtc cat aca gta ttc ctg ttt gct ctt ctt tat tct tcc     286
Trp Glu Val Val His Thr Val Phe Leu Phe Ala Leu Leu Tyr Ser Ser
    5                  10                  15 cta gct caa gat gcg agc ccc cag tca gag atc aga gct gag gaa att     334
Leu Ala Gln Asp Ala Ser Pro Gln Ser Glu Ile Arg Ala Glu Glu Ile
 20                  25                  30                  35 ccc gag ggg gcc tcc acg ttg gct ttt gtg ttt gat gtg act ggt tct     382
Pro Glu Gly Ala Ser Thr Leu Ala Phe Val Phe Asp Val Thr Gly Ser
                 40                  45                  50 atg tat gat gat tta gtt cag gtg att gaa ggg gct tcc aaa att ttg     430
Met Tyr Asp Asp Leu Val Gln Val Ile Glu Gly Ala Ser Lys Ile Leu
             55                  60                  65 gag acg tct ttg aaa aga cct aaa aga cct ctt ttc aac ttt gcg ttg     478
Glu Thr Ser Leu Lys Arg Pro Lys Arg Pro Leu Phe Asn Phe Ala Leu
         70                  75                  80 gtg cct ttc cat gat cca gaa att ggc cca gtg aca att acc aca gat     526
Val Pro Phe His Asp Pro Glu Ile Gly Pro Val Thr Ile Thr Thr Asp
     85                  90                  95 ccc aag aaa ttt caa tat gaa ctc aga gaa ctg tat gtt cag ggt ggt     574
Pro Lys Lys Phe Gln Tyr Glu Leu Arg Glu Leu Tyr Val Gln Gly Gly
100                 105                 110                 115
```

-continued

| | |
|---|---|
| ggt gat tgc cca gaa atg agt att gga gct ata aaa att gcc ttg gaa<br>Gly Asp Cys Pro Glu Met Ser Ile Gly Ala Ile Lys Ile Ala Leu Glu<br>                   120                    125                    130 | 622 |
| att tct ctt cct ggt tct ttc atc tat gtt ttc act gat gct cgg tcc<br>Ile Ser Leu Pro Gly Ser Phe Ile Tyr Val Phe Thr Asp Ala Arg Ser<br>               135                   140                   145 | 670 |
| aaa gat tac cgg ctc acc cat gag gtg ctg caa ctt atc caa cag aaa<br>Lys Asp Tyr Arg Leu Thr His Glu Val Leu Gln Leu Ile Gln Gln Lys<br>     150                   155                   160 | 718 |
| cag tca caa gtc gta ttt gtt ctg act gga gat tgt gat gac agg acc<br>Gln Ser Gln Val Val Phe Val Leu Thr Gly Asp Cys Asp Asp Arg Thr<br>165                   170                   175 | 766 |
| cat att gga tat aaa gtc tat gaa gaa att gcc tct aca agt tct ggt<br>His Ile Gly Tyr Lys Val Tyr Glu Glu Ile Ala Ser Thr Ser Ser Gly<br>180                   185                   190                   195 | 814 |
| caa gtg ttc cat ctg gac aaa aaa caa gtt aat gag gta tta aaa tgg<br>Gln Val Phe His Leu Asp Lys Lys Gln Val Asn Glu Val Leu Lys Trp<br>               200                   205                   210 | 862 |
| gta gaa gaa gca gta cag gcc tcc aaa gtt cac ctt tta tcc aca gat<br>Val Glu Glu Ala Val Gln Ala Ser Lys Val His Leu Leu Ser Thr Asp<br>                   215                   220                   225 | 910 |
| cat ttg gaa cag gct gta aat act tgg aga att cct ttt gat ccc agc<br>His Leu Glu Gln Ala Val Asn Thr Trp Arg Ile Pro Phe Asp Pro Ser<br>               230                   235                   240 | 958 |
| ctg aaa gag gtc act gtg tct ttg agt ggg cct tct cca atg att gaa<br>Leu Lys Glu Val Thr Val Ser Leu Ser Gly Pro Ser Pro Met Ile Glu<br>     245                   250                   255 | 1006 |
| att cgc aat cct tta ggg aag ctg ata aaa aag gga ttt ggc ctg cat<br>Ile Arg Asn Pro Leu Gly Lys Leu Ile Lys Lys Gly Phe Gly Leu His<br>260                   265                   270                   275 | 1054 |
| gag cta tta aat atc cat aac tct gcc aaa gta gtg aat gtg aaa gag<br>Glu Leu Leu Asn Ile His Asn Ser Ala Lys Val Val Asn Val Lys Glu<br>               280                   285                   290 | 1102 |
| cca gag gct gga atg tgg aca gtg aag acc tca agc agt gga agg cac<br>Pro Glu Ala Gly Met Trp Thr Val Lys Thr Ser Ser Ser Gly Arg His<br>                   295                   300                   305 | 1150 |
| tct gtt cgc att act ggc ctc agt act att gat ttc cga gct ggc ttt<br>Ser Val Arg Ile Thr Gly Leu Ser Thr Ile Asp Phe Arg Ala Gly Phe<br>               310                   315                   320 | 1198 |
| tct cga aag ccc acc ctg gac ttc aaa aaa aca gtc agc aga cca gtg<br>Ser Arg Lys Pro Thr Leu Asp Phe Lys Lys Thr Val Ser Arg Pro Val<br>     325                   330                   335 | 1246 |
| caa gga ata cct acc tat gta ctg ctc aat act tct gga att tcc act<br>Gln Gly Ile Pro Thr Tyr Val Leu Leu Asn Thr Ser Gly Ile Ser Thr<br>340                   345                   350                   355 | 1294 |
| cca gct aga ata gat ctt ctt gaa ctt ttg agt atc tca gga agt tct<br>Pro Ala Arg Ile Asp Leu Leu Glu Leu Leu Ser Ile Ser Gly Ser Ser<br>               360                   365                   370 | 1342 |
| ctt aag act att cct gtt aaa tat tac cca cat cga aaa cct tat ggc<br>Leu Lys Thr Ile Pro Val Lys Tyr Tyr Pro His Arg Lys Pro Tyr Gly<br>                   375                   380                   385 | 1390 |
| ata tgg aat att tct gac ttt gta cca cca aat gaa gct ttc ttt ctc<br>Ile Trp Asn Ile Ser Asp Phe Val Pro Pro Asn Glu Ala Phe Phe Leu<br>               390                   395                   400 | 1438 |
| aaa gta aca ggc tat gat aaa gat gat tac ctc ttc cag aga gta tca<br>Lys Val Thr Gly Tyr Asp Lys Asp Asp Tyr Leu Phe Gln Arg Val Ser<br>     405                   410                   415 | 1486 |
| agt gtt tcc ttt tct agt att gtc cca gat gct ccc aaa gtt acg atg<br>Ser Val Ser Phe Ser Ser Ile Val Pro Asp Ala Pro Lys Val Thr Met<br>420                   425                   430                   435 | 1534 |

| | | |
|---|---|---|
| cct gag aaa acc cca gga tac tat ctg cag ccg ggc caa att ccc tgc<br>Pro Glu Lys Thr Pro Gly Tyr Tyr Leu Gln Pro Gly Gln Ile Pro Cys<br>440 445 450 | 1582 |
| tct gtt gac agt ctt ttg ccc ttt acc ttg agc ttt gtc aga aat gga<br>Ser Val Asp Ser Leu Leu Pro Phe Thr Leu Ser Phe Val Arg Asn Gly<br>455 460 465 | 1630 |
| gtt aca ctt gga gta gac cag tat ttg aaa gaa tct gcc agt gtg aac<br>Val Thr Leu Gly Val Asp Gln Tyr Leu Lys Glu Ser Ala Ser Val Asn<br>470 475 480 | 1678 |
| tta gat att gca aag gtc act ttg tct gac gaa ggt ttc tat gaa tgc<br>Leu Asp Ile Ala Lys Val Thr Leu Ser Asp Glu Gly Phe Tyr Glu Cys<br>485 490 495 | 1726 |
| att gct gtc agc agt gca ggt act gga cgg gca cag aca ttt ttt gac<br>Ile Ala Val Ser Ser Ala Gly Thr Gly Arg Ala Gln Thr Phe Phe Asp<br>500 505 510 515 | 1774 |
| gta tca gag ccc cct ccg gtc atc caa gtg cct aac aat gtt aca gtc<br>Val Ser Glu Pro Pro Pro Val Ile Gln Val Pro Asn Asn Val Thr Val<br>520 525 530 | 1822 |
| act cct gga gag aga gca gtt tta aca tgt ctc atc atc agt gcg gtg<br>Thr Pro Gly Glu Arg Ala Val Leu Thr Cys Leu Ile Ile Ser Ala Val<br>535 540 545 | 1870 |
| gat tac aat cta acc tgg cag agg aat gac aga gat gtc aga ctg gca<br>Asp Tyr Asn Leu Thr Trp Gln Arg Asn Asp Arg Asp Val Arg Leu Ala<br>550 555 560 | 1918 |
| gag cca gcg aga att agg acc ttg gct aat ctg tca ttg gag cta aag<br>Glu Pro Ala Arg Ile Arg Thr Leu Ala Asn Leu Ser Leu Glu Leu Lys<br>565 570 575 | 1966 |
| agt gtg aaa ttc aac gat gct gga gag tat cat tgt atg gtt tct agt<br>Ser Val Lys Phe Asn Asp Ala Gly Glu Tyr His Cys Met Val Ser Ser<br>580 585 590 595 | 2014 |
| gaa ggt gga tca tca gcc gct tca gtt ttc ctc aca gtg caa gaa cca<br>Glu Gly Gly Ser Ser Ala Ala Ser Val Phe Leu Thr Val Gln Glu Pro<br>600 605 610 | 2062 |
| ccc aaa gtc act gtg atg ccc aag aat cag tct ttc aca gga ggg tct<br>Pro Lys Val Thr Val Met Pro Lys Asn Gln Ser Phe Thr Gly Gly Ser<br>615 620 625 | 2110 |
| gag gtc tcc atc atg tgt tct gca aca ggt tat ccc aaa cca aag att<br>Glu Val Ser Ile Met Cys Ser Ala Thr Gly Tyr Pro Lys Pro Lys Ile<br>630 635 640 | 2158 |
| gcc tgg acc gtt aac gat atg ttt atc gtg ggt tca cac agg tat agg<br>Ala Trp Thr Val Asn Asp Met Phe Ile Val Gly Ser His Arg Tyr Arg<br>645 650 655 | 2206 |
| atg acc tca gat ggt acc tta ttt atc aaa aat gca gct ccc aaa gat<br>Met Thr Ser Asp Gly Thr Leu Phe Ile Lys Asn Ala Ala Pro Lys Asp<br>660 665 670 675 | 2254 |
| gca ggg atc tat ggt tgc cta gca agt aat tca gct gga aca gat aaa<br>Ala Gly Ile Tyr Gly Cys Leu Ala Ser Asn Ser Ala Gly Thr Asp Lys<br>680 685 690 | 2302 |
| cag aat tct act ctc aga tac att gaa gcc cct aag ttg atg gta gtt<br>Gln Asn Ser Thr Leu Arg Tyr Ile Glu Ala Pro Lys Leu Met Val Val<br>695 700 705 | 2350 |
| cag agt gag ctc ttg gtt gcc ctt ggg gat ata acc gtt atg gaa tgc<br>Gln Ser Glu Leu Leu Val Ala Leu Gly Asp Ile Thr Val Met Glu Cys<br>710 715 720 | 2398 |
| aaa acc tct ggt att cct cca cct caa gtt aaa tgg ttc aaa gga gat<br>Lys Thr Ser Gly Ile Pro Pro Pro Gln Val Lys Trp Phe Lys Gly Asp<br>725 730 735 | 2446 |
| ctt gag ttg agg ccc tca aca ttc ctc att att gac cct ctc ttg gga<br>Leu Glu Leu Arg Pro Ser Thr Phe Leu Ile Ile Asp Pro Leu Leu Gly | 2494 |

```
                    -continued
740             745             750             755
ctt ttg aag att caa gaa aca caa gat ctg gat gct ggc gat tat acc    2542
Leu Leu Lys Ile Gln Glu Thr Gln Asp Leu Asp Ala Gly Asp Tyr Thr
                760             765             770 tgt gta gcc atc aat gag gct gga aga gca act ggc aag ata act ctg    2590
Cys Val Ala Ile Asn Glu Ala Gly Arg Ala Thr Gly Lys Ile Thr Leu
        775             780             785 gat gtt ggc tca cct cca gtt ttc ata caa gaa cct gct gat gtg tct    2638
Asp Val Gly Ser Pro Pro Val Phe Ile Gln Glu Pro Ala Asp Val Ser
            790             795             800 atg gaa att ggc tca aat gtg aca tta cct tgt tat gtt cag ggt tat    2686
Met Glu Ile Gly Ser Asn Val Thr Leu Pro Cys Tyr Val Gln Gly Tyr
    805             810             815 cca gaa cca aca atc aaa tgg cga aga tta gac aac atg cca att ttc    2734
Pro Glu Pro Thr Ile Lys Trp Arg Arg Leu Asp Asn Met Pro Ile Phe
820             825             830             835 tca aga cct ttt tca gtt agt tcc atc agc caa cta aga aca gga gct    2782
Ser Arg Pro Phe Ser Val Ser Ser Ile Ser Gln Leu Arg Thr Gly Ala
                840             845             850 ctc ttt att tta aac tta tgg gca agt gat aaa gga acc tat att tgt    2830
Leu Phe Ile Leu Asn Leu Trp Ala Ser Asp Lys Gly Thr Tyr Ile Cys
        855             860             865 gaa gct gaa aac cag ttt gga aag atc cag tca gag aca aca gta aca    2878
Glu Ala Glu Asn Gln Phe Gly Lys Ile Gln Ser Glu Thr Thr Val Thr
            870             875             880 gtg acc gga ctt gtt gct cca ctt att gga atc agc cct tca gtg gcc    2926
Val Thr Gly Leu Val Ala Pro Leu Ile Gly Ile Ser Pro Ser Val Ala
    885             890             895 aat gtt att gaa gga cag cag ctt act ttg ccc tgt act ctg tta gct    2974
Asn Val Ile Glu Gly Gln Gln Leu Thr Leu Pro Cys Thr Leu Leu Ala
900             905             910             915 gga aat ccc att cca gaa cgt cgg tgg att aag aat tca gct atg ttg    3022
Gly Asn Pro Ile Pro Glu Arg Arg Trp Ile Lys Asn Ser Ala Met Leu
                920             925             930 ctc caa aat cct tac atc act gtg cgc agt gat ggg agc ctc cat att    3070
Leu Gln Asn Pro Tyr Ile Thr Val Arg Ser Asp Gly Ser Leu His Ile
        935             940             945 gaa aga gtt cag ctt cag gat ggt ggt gaa tat act tgt gtg gcc agt    3118
Glu Arg Val Gln Leu Gln Asp Gly Gly Glu Tyr Thr Cys Val Ala Ser
            950             955             960 aac gtt gct ggg acc aat aac aaa act acc tct gtg gtt gtg cat gtt    3166
Asn Val Ala Gly Thr Asn Asn Lys Thr Thr Ser Val Val Val His Val
    965             970             975 ctg cca acc att cag cat ggg cag cag ata ctc agt aca att gaa ggc    3214
Leu Pro Thr Ile Gln His Gly Gln Gln Ile Leu Ser Thr Ile Glu Gly
 980             985             990             995 att cca gta act tta cca tgc aaa gca agt gga aat ccc aaa ccg tct    3262
Ile Pro Val Thr Leu Pro Cys Lys Ala Ser Gly Asn Pro Lys Pro Ser
                1000            1005            1010 gtc atc tgg tcc aag aaa gga gag ctg att tca acc agc agt gct aag    3310
Val Ile Trp Ser Lys Lys Gly Glu Leu Ile Ser Thr Ser Ser Ala Lys
        1015            1020            1025 ttt tca gca gga gct gat ggt agt ctg tat gtg gta tca cct gga gga    3358
Phe Ser Ala Gly Ala Asp Gly Ser Leu Tyr Val Val Ser Pro Gly Gly
            1030            1035            1040 gag gag agt ggg gag tat gtc tgc act gcc acc aat aca gcc ggc tac    3406
Glu Glu Ser Gly Glu Tyr Val Cys Thr Ala Thr Asn Thr Ala Gly Tyr
    1045            1050            1055 gcc aaa agg aaa gtg cag cta aca gtc tat gta agg ccc aga gtg ttt    3454
Ala Lys Arg Lys Val Gln Leu Thr Val Tyr Val Arg Pro Arg Val Phe
```

```
Ala Lys Arg Lys Val Gln Leu Thr Val Tyr Val Arg Pro Arg Val Phe
1060                1065                1070                1075 gga gat caa cga gga ctg tcc cag gat aag cct gtt gag atc tcc gtc      3502
Gly Asp Gln Arg Gly Leu Ser Gln Asp Lys Pro Val Glu Ile Ser Val
                1080                1085                1090 ctt gca ggg gaa gag gta aca ctt cca tgt gaa gtg aag agc tta cct      3550
Leu Ala Gly Glu Glu Val Thr Leu Pro Cys Glu Val Lys Ser Leu Pro
            1095                1100                1105 cca ccc ata att act tgg gcc aaa gaa acc cag ctc atc tca ccg ttc      3598
Pro Pro Ile Ile Thr Trp Ala Lys Glu Thr Gln Leu Ile Ser Pro Phe
        1110                1115                1120 tct cca aga cac aca ttc ctc cct tct ggt tca atg aag atc act gaa      3646
Ser Pro Arg His Thr Phe Leu Pro Ser Gly Ser Met Lys Ile Thr Glu
    1125                1130                1135 acc cgc act tca gat agt ggg atg tat ctt tgt gtt gcc aca aat att      3694
Thr Arg Thr Ser Asp Ser Gly Met Tyr Leu Cys Val Ala Thr Asn Ile
1140                1145                1150                1155 gct ggg aat gtg act cag gct gtc aaa tta aat gtc cat gtt cct cca      3742
Ala Gly Asn Val Thr Gln Ala Val Lys Leu Asn Val His Val Pro Pro
                1160                1165                1170 aag ata cag cgt gga cct aaa cat ctc aaa gtc caa gtt ggt caa aga      3790
Lys Ile Gln Arg Gly Pro Lys His Leu Lys Val Gln Val Gly Gln Arg
            1175                1180                1185 gtg gat att cca tgt aat gct caa ggg act cct ctt cct gta atc acc      3838
Val Asp Ile Pro Cys Asn Ala Gln Gly Thr Pro Leu Pro Val Ile Thr
        1190                1195                1200 tgg tcc aaa ggt gga agc act atg ctg gtt gat gga gag cac cat gtt      3886
Trp Ser Lys Gly Gly Ser Thr Met Leu Val Asp Gly Glu His His Val
    1205                1210                1215 agc aat cca gac gga act tta agc atc gac caa gcc acg ccc tca gat      3934
Ser Asn Pro Asp Gly Thr Leu Ser Ile Asp Gln Ala Thr Pro Ser Asp
1220                1225                1230                1235 gct ggc ata tat aca tgt gtt gct act aac ata gca ggc act gat gaa      3982
Ala Gly Ile Tyr Thr Cys Val Ala Thr Asn Ile Ala Gly Thr Asp Glu
                1240                1245                1250 aca gag ata acg cta cat gtc caa gaa cca ccc aca gtg gaa gat cta      4030
Thr Glu Ile Thr Leu His Val Gln Glu Pro Pro Thr Val Glu Asp Leu
            1255                1260                1265 gaa cct cca tat aac act act ttc caa gaa aga gtg gcc aat caa cgc      4078
Glu Pro Pro Tyr Asn Thr Thr Phe Gln Glu Arg Val Ala Asn Gln Arg
        1270                1275                1280 att gaa ttt cca tgt cct gca aaa ggt acc cct aaa cca acc atc aaa      4126
Ile Glu Phe Pro Cys Pro Ala Lys Gly Thr Pro Lys Pro Thr Ile Lys
    1285                1290                1295 tgg tta cac aat ggt aga gag ttg aca ggc aga gag cct ggc att tct      4174
Trp Leu His Asn Gly Arg Glu Leu Thr Gly Arg Glu Pro Gly Ile Ser
1300                1305                1310                1315 atc ttg gaa gat ggc aca ttg ctg gtt att gct tct gtt aca ccc tat      4222
Ile Leu Glu Asp Gly Thr Leu Leu Val Ile Ala Ser Val Thr Pro Tyr
                1320                1325                1330 gac aat ggg gag tac atc tgt gtg gca gtc aat gaa gct gga acc aca      4270
Asp Asn Gly Glu Tyr Ile Cys Val Ala Val Asn Glu Ala Gly Thr Thr
            1335                1340                1345 gaa aga aaa tat aac ctc aaa gtc cat gtt cct cca gta att aaa gat      4318
Glu Arg Lys Tyr Asn Leu Lys Val His Val Pro Pro Val Ile Lys Asp
        1350                1355                1360 aaa gaa caa gtt aca aat gtg tcg gtg ttg tta aat cag ctg acc aat      4366
Lys Glu Gln Val Thr Asn Val Ser Val Leu Leu Asn Gln Leu Thr Asn
    1365                1370                1375
```

-continued

| | |
|---|---|
| ctc ttc tgt gaa gtg gaa ggc act cca tct ccc atc att atg tgg tat<br>Leu Phe Cys Glu Val Glu Gly Thr Pro Ser Pro Ile Ile Met Trp Tyr<br>1380               1385                1390              1395 | 4414 |
| aaa gat aat gtc cag gtg act gaa agc agc act att cag act gtg aac<br>Lys Asp Asn Val Gln Val Thr Glu Ser Ser Thr Ile Gln Thr Val Asn<br>                1400                1405              1410 | 4462 |
| aat ggg aag ata ctg aag ctc ttc aga gcc act cca gag gat gca gga<br>Asn Gly Lys Ile Leu Lys Leu Phe Arg Ala Thr Pro Glu Asp Ala Gly<br>1415               1420                1425 | 4510 |
| aga tat tcc tgc aaa gca att aat att gca ggc act tct cag aag tac<br>Arg Tyr Ser Cys Lys Ala Ile Asn Ile Ala Gly Thr Ser Gln Lys Tyr<br>                1430                1435              1440 | 4558 |
| ttt aac att gat gtg cta gtt cca ccc acc ata ata ggt acc aac ttc<br>Phe Asn Ile Asp Val Leu Val Pro Pro Thr Ile Ile Gly Thr Asn Phe<br>1445               1450                1455 | 4606 |
| cca aat gaa gtc tca gtt gtc ctc aac cgt gac gtc gcc ctt gaa tgc<br>Pro Asn Glu Val Ser Val Val Leu Asn Arg Asp Val Ala Leu Glu Cys<br>1460               1465                1470              1475 | 4654 |
| cag gtc aaa ggc act ccc ttt cct gat att cat tgg ttc aaa gat ggc<br>Gln Val Lys Gly Thr Pro Phe Pro Asp Ile His Trp Phe Lys Asp Gly<br>                1480                1485              1490 | 4702 |
| aag cct tta ttt ttg ggc gat cct aat gtt gaa ctt cta gac aga gga<br>Lys Pro Leu Phe Leu Gly Asp Pro Asn Val Glu Leu Leu Asp Arg Gly<br>1495               1500                1505 | 4750 |
| caa gtc tta cat tta aag aat gca cgg aga aat gac aag ggg cgc tac<br>Gln Val Leu His Leu Lys Asn Ala Arg Arg Asn Asp Lys Gly Arg Tyr<br>                1510                1515              1520 | 4798 |
| caa tgt act gtg tct aat gca gct ggc aaa caa gcc aag gat ata aaa<br>Gln Cys Thr Val Ser Asn Ala Ala Gly Lys Gln Ala Lys Asp Ile Lys<br>1525               1530                1535 | 4846 |
| ctg act atc tat aat cct cct agt att aaa gga gga aat gtc acc aca<br>Leu Thr Ile Tyr Asn Pro Pro Ser Ile Lys Gly Gly Asn Val Thr Thr<br>1540               1545                1550              1555 | 4894 |
| gac ata tca gta ttg atc aac agc ctt att aaa ctg gaa tgt gaa aca<br>Asp Ile Ser Val Leu Ile Asn Ser Leu Ile Lys Leu Glu Cys Glu Thr<br>                1560                1565              1570 | 4942 |
| cgg gga ctt cca atg cct gcc att act tgg tat aag gac ggg cag cca<br>Arg Gly Leu Pro Met Pro Ala Ile Thr Trp Tyr Lys Asp Gly Gln Pro<br>1575               1580                1585 | 4990 |
| atc atg tcc agc tca caa gca ctt tat att gat aaa gga caa tat ctt<br>Ile Met Ser Ser Ser Gln Ala Leu Tyr Ile Asp Lys Gly Gln Tyr Leu<br>                1590                1595              1600 | 5038 |
| cat att cct cga gca cag gtc tct gat tca gca aca tat acg tgt cac<br>His Ile Pro Arg Ala Gln Val Ser Asp Ser Ala Thr Tyr Thr Cys His<br>1605               1610                1615 | 5086 |
| gta gcc aat gtt gct gga act gct gaa aaa tca ttc cat gtg gat gtc<br>Val Ala Asn Val Ala Gly Thr Ala Glu Lys Ser Phe His Val Asp Val<br>1620               1625                1630              1635 | 5134 |
| tat gtt cct cca atg att gaa ggc aac ttg gcc acg cct ttg aat aag<br>Tyr Val Pro Pro Met Ile Glu Gly Asn Leu Ala Thr Pro Leu Asn Lys<br>                1640                1645              1650 | 5182 |
| caa gta gtt att gct cat tct ctg aca ctg gag tgc aaa gct gct gga<br>Gln Val Val Ile Ala His Ser Leu Thr Leu Glu Cys Lys Ala Ala Gly<br>1655               1660                1665 | 5230 |
| aac cct tct ccc att ctc acc tgg ttg aaa gat ggt gta cct gtg aaa<br>Asn Pro Ser Pro Ile Leu Thr Trp Leu Lys Asp Gly Val Pro Val Lys<br>                1670                1675              1680 | 5278 |
| gct aat gac aat atc cgc ata gaa gct ggt ggg aag aaa ctc gaa atc<br>Ala Asn Asp Asn Ile Arg Ile Glu Ala Gly Gly Lys Lys Leu Glu Ile<br>1685               1690                1695 | 5326 |

-continued

| | |
|---|---|
| atg agt gcc caa gaa att gat cga gga cag tac ata tgc gtg gct acc<br>Met Ser Ala Gln Glu Ile Asp Arg Gly Gln Tyr Ile Cys Val Ala Thr<br>1700                   1705                  1710                  1715 | 5374 |
| agt gtg gca gga gaa aag gaa atc aaa tat gaa gtt gat gtc ttg gtg<br>Ser Val Ala Gly Glu Lys Glu Ile Lys Tyr Glu Val Asp Val Leu Val<br>                 1720                  1725                  1730 | 5422 |
| cca cca gct ata gaa gga gga gat gaa aca tct tac ttc att gtg atg<br>Pro Pro Ala Ile Glu Gly Gly Asp Glu Thr Ser Tyr Phe Ile Val Met<br>                1735                  1740                  1745 | 5470 |
| gtt aat aac tta ctg gag cta gat tgt cat gtg aca ggc tct ccc cca<br>Val Asn Asn Leu Leu Glu Leu Asp Cys His Val Thr Gly Ser Pro Pro<br>        1750                  1755                  1760 | 5518 |
| cca act atc atg tgg ctg aag gat ggc cag tta att gat gaa agg gat<br>Pro Thr Ile Met Trp Leu Lys Asp Gly Gln Leu Ile Asp Glu Arg Asp<br>        1765                  1770                  1775 | 5566 |
| gga ttc aag att tta tta aat gga cgc aaa ctg gtt att gct cag gct<br>Gly Phe Lys Ile Leu Leu Asn Gly Arg Lys Leu Val Ile Ala Gln Ala<br>1780                   1785                  1790                  1795 | 5614 |
| caa gtg tca aac aca ggc ctt tat cgg tgc atg gca gca aat act gct<br>Gln Val Ser Asn Thr Gly Leu Tyr Arg Cys Met Ala Ala Asn Thr Ala<br>                 1800                  1805                  1810 | 5662 |
| gga gac cac aag aag gaa ttt gaa gtg act gtt cat gtt cct cca aca<br>Gly Asp His Lys Lys Glu Phe Glu Val Thr Val His Val Pro Pro Thr<br>                 1815                  1820                  1825 | 5710 |
| atc aag tcc tca ggc ctt tct gag aga gtt gtg gta aaa tac aag cct<br>Ile Lys Ser Ser Gly Leu Ser Glu Arg Val Val Val Lys Tyr Lys Pro<br>        1830                  1835                  1840 | 5758 |
| gtc gcc ttg cag tgc ata gcc aat ggg att cca aat cct tcc att aca<br>Val Ala Leu Gln Cys Ile Ala Asn Gly Ile Pro Asn Pro Ser Ile Thr<br>        1845                  1850                  1855 | 5806 |
| tgg tta aaa gat gac cag cct gtg aac act gcc caa gga aac ctt aaa<br>Trp Leu Lys Asp Asp Gln Pro Val Asn Thr Ala Gln Gly Asn Leu Lys<br>1860                   1865                  1870                  1875 | 5854 |
| ata cag tct tct ggt cga gtt cta caa att gcc aaa acc ctg ttg gaa<br>Ile Gln Ser Ser Gly Arg Val Leu Gln Ile Ala Lys Thr Leu Leu Glu<br>                 1880                  1885                  1890 | 5902 |
| gat gct ggc aga tac aca tgt gtg gct acc aac gca gct gga gaa aca<br>Asp Ala Gly Arg Tyr Thr Cys Val Ala Thr Asn Ala Ala Gly Glu Thr<br>        1895                  1900                  1905 | 5950 |
| caa cag cac att caa ctg cat gtt cat gaa cca cct agt ctg gaa gat<br>Gln Gln His Ile Gln Leu His Val His Glu Pro Pro Ser Leu Glu Asp<br>        1910                  1915                  1920 | 5998 |
| gct gga aaa atg ctg aat gag act gtg ttg gtg agc aac cct gta cag<br>Ala Gly Lys Met Leu Asn Glu Thr Val Leu Val Ser Asn Pro Val Gln<br>1925                   1930                  1935 | 6046 |
| ctg gag tgt aag gca gct gga aat cct gtg cct gtt att aca tgg tac<br>Leu Glu Cys Lys Ala Ala Gly Asn Pro Val Pro Val Ile Thr Trp Tyr<br>1940                   1945                  1950                  1955 | 6094 |
| aaa gat aat cgt cta ctc tca ggt tcc acc agc atg act ttc ttg aac<br>Lys Asp Asn Arg Leu Leu Ser Gly Ser Thr Ser Met Thr Phe Leu Asn<br>                 1960                  1965                  1970 | 6142 |
| aga gga cag atc att gat att gaa agt gcc cag atc tca gat gct ggc<br>Arg Gly Gln Ile Ile Asp Ile Glu Ser Ala Gln Ile Ser Asp Ala Gly<br>        1975                  1980                  1985 | 6190 |
| ata tat aaa tgc gtg gcc atc aac tca gct gga gct aca gag tta ttt<br>Ile Tyr Lys Cys Val Ala Ile Asn Ser Ala Gly Ala Thr Glu Leu Phe<br>        1990                  1995                  2000 | 6238 |
| tac agt ctg caa gtt cat gtg gcc cca tca att tct ggc agc aat aac<br>Tyr Ser Leu Gln Val His Val Ala Pro Ser Ile Ser Gly Ser Asn Asn | 6286 |

-continued

```
            2005                 2010                 2015
atg gta gca gtg gtg gtt aat aac ccg gtg agg tta gaa tgt gaa gcc      6334
Met Val Ala Val Val Val Asn Asn Pro Val Arg Leu Glu Cys Glu Ala
2020                2025                2030                2035 aga ggt att cct gcc cca agt ctg acc tgg ttg aaa gat ggg agt cct      6382
Arg Gly Ile Pro Ala Pro Ser Leu Thr Trp Leu Lys Asp Gly Ser Pro
        2040                2045                2050 gtt tct agt ttt tct aat gga tta cag gtt ctc tct ggt ggt cga atc      6430
Val Ser Ser Phe Ser Asn Gly Leu Gln Val Leu Ser Gly Gly Arg Ile
    2055                2060                2065 cta gca ttg acc agt gca caa atc agc gac aca gga agg tac acc tgc      6478
Leu Ala Leu Thr Ser Ala Gln Ile Ser Asp Thr Gly Arg Tyr Thr Cys
        2070                2075                2080 gtg gca gtg aat gct gct gga gaa aag caa agg gac att gac ctc cga      6526
Val Ala Val Asn Ala Ala Gly Glu Lys Gln Arg Asp Ile Asp Leu Arg
    2085                2090                2095 gta tat gtt ccg cca aat att atg gga gaa gaa cag aat gtc tct gtc      6574
Val Tyr Val Pro Pro Asn Ile Met Gly Glu Glu Gln Asn Val Ser Val
2100                2105                2110                2115 ctc att agc caa gct gtg gaa tta cta tgt caa agt gat gct att ccc      6622
Leu Ile Ser Gln Ala Val Glu Leu Leu Cys Gln Ser Asp Ala Ile Pro
        2120                2125                2130 cca cct act ctt act tgg tta aaa gac ggc cac ccc ttg ctg aag aaa      6670
Pro Pro Thr Leu Thr Trp Leu Lys Asp Gly His Pro Leu Leu Lys Lys
    2135                2140                2145 cca ggc ctc agt ata tct gaa aat aga agt gtg tta aag att gaa gat      6718
Pro Gly Leu Ser Ile Ser Glu Asn Arg Ser Val Leu Lys Ile Glu Asp
        2150                2155                2160 gct cag gtt caa gac act ggt cgt tac act tgt gaa gca aca aat gtt      6766
Ala Gln Val Gln Asp Thr Gly Arg Tyr Thr Cys Glu Ala Thr Asn Val
    2165                2170                2175 gct gga aaa act gaa aaa aac tac aat gtc aac att tgg gtc ccc cca      6814
Ala Gly Lys Thr Glu Lys Asn Tyr Asn Val Asn Ile Trp Val Pro Pro
2180                2185                2190                2195 aat att ggt ggt tct gat gaa ctt act caa ctt aca gtc att gaa ggg      6862
Asn Ile Gly Gly Ser Asp Glu Leu Thr Gln Leu Thr Val Ile Glu Gly
        2200                2205                2210 aat ctc att agt ctg ttg tgt gaa tca agt ggt att cca ccc cca aat      6910
Asn Leu Ile Ser Leu Leu Cys Glu Ser Ser Gly Ile Pro Pro Pro Asn
    2215                2220                2225 ctc atc tgg aag aag aaa ggc tct cca gtg ctg act gat tcc atg ggg      6958
Leu Ile Trp Lys Lys Lys Gly Ser Pro Val Leu Thr Asp Ser Met Gly
        2230                2235                2240 cga gtt aga att tta tct ggg ggc agg caa tta caa att tca att gct      7006
Arg Val Arg Ile Leu Ser Gly Gly Arg Gln Leu Gln Ile Ser Ile Ala
    2245                2250                2255 gaa aag tct gat gca gca ctc tat tca tgt gtg gcg tcg aat gtt gct      7054
Glu Lys Ser Asp Ala Ala Leu Tyr Ser Cys Val Ala Ser Asn Val Ala
2260                2265                2270                2275 ggg act gca aag aaa gaa tac aat ctg caa gtt tac att aga cca acc      7102
Gly Thr Ala Lys Lys Glu Tyr Asn Leu Gln Val Tyr Ile Arg Pro Thr
        2280                2285                2290 ata acc aac agt ggc agc cac cct act gaa att att gtg acc cga ggg      7150
Ile Thr Asn Ser Gly Ser His Pro Thr Glu Ile Ile Val Thr Arg Gly
    2295                2300                2305 aag agt atc tcc ttg gag tgt gag gtg cag ggt att cca cca cca aca      7198
Lys Ser Ile Ser Leu Glu Cys Glu Val Gln Gly Ile Pro Pro Pro Thr
        2310                2315                2320 gtg acc tgg atg aaa gat ggc cac ccc ttg atc aag gca aag gga gta      7246
```

```
Val Thr Trp Met Lys Asp Gly His Pro Leu Ile Lys Ala Lys Gly Val
    2325                2330                2335 gaa ata ctg gat gaa ggt cac atc ctt cag ctg aag aac att cat gta      7294
Glu Ile Leu Asp Glu Gly His Ile Leu Gln Leu Lys Asn Ile His Val
2340            2345                2350                2355 tct gac aca ggc cgt tat gtg tgt gtt gct gtg aat gta gca gga atg      7342
Ser Asp Thr Gly Arg Tyr Val Cys Val Ala Val Asn Val Ala Gly Met
                2360                2365                2370 act gac aaa aaa tat gac tta agt gtc cat gct cct cca agc atc ata      7390
Thr Asp Lys Lys Tyr Asp Leu Ser Val His Ala Pro Pro Ser Ile Ile
            2375                2380                2385 gga aac cac agg tca cct gaa aat att agt gtg gta gaa aag aac tca      7438
Gly Asn His Arg Ser Pro Glu Asn Ile Ser Val Val Glu Lys Asn Ser
        2390                2395                2400 gta tct ttg act tgt gaa gct tct gga att ccc ctg cct tcc ata acc      7486
Val Ser Leu Thr Cys Glu Ala Ser Gly Ile Pro Leu Pro Ser Ile Thr
    2405                2410                2415 tgg ttc aaa gat ggg tgg cct gtc agc ctt agc aat tct gtg agg att      7534
Trp Phe Lys Asp Gly Trp Pro Val Ser Leu Ser Asn Ser Val Arg Ile
2420                2425                2430                2435 ctt tca gga ggc agg atg cta cgg ctg atg cag acc aca atg gaa gat      7582
Leu Ser Gly Gly Arg Met Leu Arg Leu Met Gln Thr Thr Met Glu Asp
                2440                2445                2450 gct ggc caa tat act tgc gtt gta agg aat gca gct ggt gaa gaa aga      7630
Ala Gly Gln Tyr Thr Cys Val Val Arg Asn Ala Ala Gly Glu Glu Arg
            2455                2460                2465 aaa atc ttt ggg ctt tca gta tta gta cca cct cat att gtg ggt gaa      7678
Lys Ile Phe Gly Leu Ser Val Leu Val Pro Pro His Ile Val Gly Glu
        2470                2475                2480 aat aca ttg gaa gat gtg aag gta aaa gag aaa cag agt gtt acg ctg      7726
Asn Thr Leu Glu Asp Val Lys Val Lys Glu Lys Gln Ser Val Thr Leu
    2485                2490                2495 act tgt gaa gta aca ggg aat cca gtg cca gaa att aca tgg cac aaa      7774
Thr Cys Glu Val Thr Gly Asn Pro Val Pro Glu Ile Thr Trp His Lys
2500                2505                2510                2515 gat ggg cag ccc ctc caa gaa gat gaa gcc cat cac att ata tct ggt      7822
Asp Gly Gln Pro Leu Gln Glu Asp Glu Ala His His Ile Ile Ser Gly
                2520                2525                2530 ggc cgt ttt ctt caa att acc aat gtc cag gtg cca cac act gga aga      7870
Gly Arg Phe Leu Gln Ile Thr Asn Val Gln Val Pro His Thr Gly Arg
            2535                2540                2545 tat aca tgt ttg gct tcc agt cca gct ggc cac aag agc agg agc ttc      7918
Tyr Thr Cys Leu Ala Ser Ser Pro Ala Gly His Lys Ser Arg Ser Phe
        2550                2555                2560 agt ctt aat gta ttt gta tct cct aca att gct ggt gta ggt agt gat      7966
Ser Leu Asn Val Phe Val Ser Pro Thr Ile Ala Gly Val Gly Ser Asp
    2565                2570                2575 ggc aac cct gaa gat gtc act gtc atc ctt aac agc cct aca tct ttg      8014
Gly Asn Pro Glu Asp Val Thr Val Ile Leu Asn Ser Pro Thr Ser Leu
2580                2585                2590                2595 gtc tgt gaa gct tat tca tat cct cca gct acc atc acc tgg ttt aag      8062
Val Cys Glu Ala Tyr Ser Tyr Pro Pro Ala Thr Ile Thr Trp Phe Lys
                2600                2605                2610 gat ggc act cct tta gaa tct aac cga aat att cgt att ctt cca gga      8110
Asp Gly Thr Pro Leu Glu Ser Asn Arg Asn Ile Arg Ile Leu Pro Gly
            2615                2620                2625 ggc aga act ctg cag atc ctc aat gca cag gag gac aat gct gga aga      8158
Gly Arg Thr Leu Gln Ile Leu Asn Ala Gln Glu Asp Asn Ala Gly Arg
        2630                2635                2640
```

```
                                             -continued
tac tct tgt gta gcc acg aat gag gct gga gaa atg ata aag cac tat      8206
Tyr Ser Cys Val Ala Thr Asn Glu Ala Gly Glu Met Ile Lys His Tyr
    2645                2650                2655 gaa gtg aag gtg tac att cca ccc ata atc aat aaa ggg gac ctt tgg      8254
Glu Val Lys Val Tyr Ile Pro Pro Ile Ile Asn Lys Gly Asp Leu Trp
2660                2665                2670                2675 ggg cca ggt ctt tcc cct aaa gaa gtg aag atc aaa gta aac aac act      8302
Gly Pro Gly Leu Ser Pro Lys Glu Val Lys Ile Lys Val Asn Asn Thr
                2680                2685                2690 ctg acc ttg gaa tgt gaa gcg tat gca att cct tct gcc tcc ctc agc      8350
Leu Thr Leu Glu Cys Glu Ala Tyr Ala Ile Pro Ser Ala Ser Leu Ser
            2695                2700                2705 tgg tac aag gat gga cag ccc ctt aaa tcc gat gat cat gtt aat att      8398
Trp Tyr Lys Asp Gly Gln Pro Leu Lys Ser Asp Asp His Val Asn Ile
        2710                2715                2720 gct gcg aat gga cac aca ctt caa ata aag gag gct caa ata tca gac      8446
Ala Ala Asn Gly His Thr Leu Gln Ile Lys Glu Ala Gln Ile Ser Asp
    2725                2730                2735 acc gga cga tat act tgt gta gca tct aac att gca ggt gaa gat gag      8494
Thr Gly Arg Tyr Thr Cys Val Ala Ser Asn Ile Ala Gly Glu Asp Glu
2740                2745                2750                2755 ttg gat ttt gat gtg aat att caa gtt cct cca agt ttt cag aaa ctc      8542
Leu Asp Phe Asp Val Asn Ile Gln Val Pro Pro Ser Phe Gln Lys Leu
                2760                2765                2770 tgg gaa ata gga aac atg cta gat act ggc agg aat ggt gaa gcc aaa      8590
Trp Glu Ile Gly Asn Met Leu Asp Thr Gly Arg Asn Gly Glu Ala Lys
            2775                2780                2785 gat gtg atc atc aac aat ccc att tct ctt tac tgt gag aca aat gct      8638
Asp Val Ile Ile Asn Asn Pro Ile Ser Leu Tyr Cys Glu Thr Asn Ala
        2790                2795                2800 gct ccc cct cct aca ctg aca tgg tac aaa gat ggc cac cct ctg acc      8686
Ala Pro Pro Pro Thr Leu Thr Trp Tyr Lys Asp Gly His Pro Leu Thr
    2805                2810                2815 tca agt gat aaa gta ttg att ttg cca gga ggg cga gtg ttg cag att      8734
Ser Ser Asp Lys Val Leu Ile Leu Pro Gly Gly Arg Val Leu Gln Ile
2820                2825                2830                2835 cct cgg gct aaa gta gaa gat gct ggg aga tac aca tgt gtg gct gtg      8782
Pro Arg Ala Lys Val Glu Asp Ala Gly Arg Tyr Thr Cys Val Ala Val
                2840                2845                2850 aat gag gct gga gaa gat tcc ctt caa tat gat gtc cgt gta ctc gtg      8830
Asn Glu Ala Gly Glu Asp Ser Leu Gln Tyr Asp Val Arg Val Leu Val
            2855                2860                2865 ccg cca att atc aag gga gca aat agt gat ctc cct gaa gag gtc acc      8878
Pro Pro Ile Ile Lys Gly Ala Asn Ser Asp Leu Pro Glu Glu Val Thr
        2870                2875                2880 gtg ctg gtg aac aag agt gca ctg ata gag tgt tta tcc agt ggc agc      8926
Val Leu Val Asn Lys Ser Ala Leu Ile Glu Cys Leu Ser Ser Gly Ser
    2885                2890                2895 cca gca cca agg aat tcc tgg cag aaa gat gga cag ccc ttg cta gaa      8974
Pro Ala Pro Arg Asn Ser Trp Gln Lys Asp Gly Gln Pro Leu Leu Glu
2900                2905                2910                2915 gat gac cat cat aaa ttt cta tct aat gga cga att ctg cag att ctg      9022
Asp Asp His His Lys Phe Leu Ser Asn Gly Arg Ile Leu Gln Ile Leu
                2920                2925                2930 aat act caa ata aca gat atc ggc agg tat gtg tgt gtt gct gag aac      9070
Asn Thr Gln Ile Thr Asp Ile Gly Arg Tyr Val Cys Val Ala Glu Asn
            2935                2940                2945 aca gct ggg agt gcc aaa aaa tat ttt aac ctc aat gtt cat gtt cct      9118
Thr Ala Gly Ser Ala Lys Lys Tyr Phe Asn Leu Asn Val His Val Pro
        2950                2955                2960
```

-continued

| | |
|---|---|
| cca agt gtc att ggt cct aaa tct gaa aat ctt acc gtc gtg gtg aac<br>Pro Ser Val Ile Gly Pro Lys Ser Glu Asn Leu Thr Val Val Val Asn<br>2965                    2970                    2975 | 9166 |
| aat ttc atc tct ttg acc tgt gag gtc tct ggt ttt cca cct cct gac<br>Asn Phe Ile Ser Leu Thr Cys Glu Val Ser Gly Phe Pro Pro Pro Asp<br>2980                    2985                    2990                    2995 | 9214 |
| ctc agc tgg ctc aag aat gaa cag ccc atc aaa ctg aac aca aat act<br>Leu Ser Trp Leu Lys Asn Glu Gln Pro Ile Lys Leu Asn Thr Asn Thr<br>                3000                    3005                    3010 | 9262 |
| ctc att gtg cct ggt ggt cga act cta cag att att cgg gcc aag gta<br>Leu Ile Val Pro Gly Gly Arg Thr Leu Gln Ile Ile Arg Ala Lys Val<br>                3015                    3020                    3025 | 9310 |
| tca gat ggt ggt gaa tac act tgt ata gct atc aat caa gct ggc gaa<br>Ser Asp Gly Gly Glu Tyr Thr Cys Ile Ala Ile Asn Gln Ala Gly Glu<br>3030                    3035                    3040 | 9358 |
| agc aag aaa aag ttt tcc ctg act gtt tat gtg ccc cca agc att aaa<br>Ser Lys Lys Lys Phe Ser Leu Thr Val Tyr Val Pro Pro Ser Ile Lys<br>3045                    3050                    3055 | 9406 |
| gac cat gac agt gaa tct ctt tct gta gtt aat gta aga gag gga act<br>Asp His Asp Ser Glu Ser Leu Ser Val Val Asn Val Arg Glu Gly Thr<br>3060                    3065                    3070                    3075 | 9454 |
| tct gtg tct ttg gag tgt gag tcg aac gct gtg cca cct cca gtc atc<br>Ser Val Ser Leu Glu Cys Glu Ser Asn Ala Val Pro Pro Pro Val Ile<br>                3080                    3085                    3090 | 9502 |
| act tgg tat aag aat ggg cgg atg ata aca gag tct act cat gtg gag<br>Thr Trp Tyr Lys Asn Gly Arg Met Ile Thr Glu Ser Thr His Val Glu<br>                3095                    3100                    3105 | 9550 |
| att tta gct gat gga caa atg cta cac att aag aaa gct gag gta tct<br>Ile Leu Ala Asp Gly Gln Met Leu His Ile Lys Lys Ala Glu Val Ser<br>3110                    3115                    3120 | 9598 |
| gac aca ggc cag tat gta tgt aga gct ata aat gta gca gga cgg gat<br>Asp Thr Gly Gln Tyr Val Cys Arg Ala Ile Asn Val Ala Gly Arg Asp<br>3125                    3130                    3135 | 9646 |
| gat aaa aat ttc cac ctc aat gta tat gtg cca ccc agt att gaa gga<br>Asp Lys Asn Phe His Leu Asn Val Tyr Val Pro Pro Ser Ile Glu Gly<br>3140                    3145                    3150                    3155 | 9694 |
| cct gaa aga gaa gtg att gtg gag acg atc agc aat cct gtg aca tta<br>Pro Glu Arg Glu Val Ile Val Glu Thr Ile Ser Asn Pro Val Thr Leu<br>                3160                    3165                    3170 | 9742 |
| aca tgt gat gcc act ggg atc cca cct ccc acg ata gca tgg tta aag<br>Thr Cys Asp Ala Thr Gly Ile Pro Pro Pro Thr Ile Ala Trp Leu Lys<br>                3175                    3180                    3185 | 9790 |
| aac cac aag cgc ata gaa aat tct gac tca ctg gaa gtt cgt att ttg<br>Asn His Lys Arg Ile Glu Asn Ser Asp Ser Leu Glu Val Arg Ile Leu<br>3190                    3195                    3200 | 9838 |
| tct gga ggt agc aaa ctc cag att gcc cgg tct cag cat tca gat agt<br>Ser Gly Gly Ser Lys Leu Gln Ile Ala Arg Ser Gln His Ser Asp Ser<br>3205                    3210                    3215 | 9886 |
| gga aac tat aca tgt att gct tca aat atg gag gga aaa gcc cag aaa<br>Gly Asn Tyr Thr Cys Ile Ala Ser Asn Met Glu Gly Lys Ala Gln Lys<br>3220                    3225                    3230                    3235 | 9934 |
| tat tac ttt ctt tca att caa gtt cct cca agt gtt gct ggt gct gaa<br>Tyr Tyr Phe Leu Ser Ile Gln Val Pro Pro Ser Val Ala Gly Ala Glu<br>                3240                    3245                    3250 | 9982 |
| att cca agt gat gtc agt gtc ctt cta gga gaa aat gtt gag ctg gtc<br>Ile Pro Ser Asp Val Ser Val Leu Leu Gly Glu Asn Val Glu Leu Val<br>                3255                    3260                    3265 | 10030 |
| tgc aat gca aat ggc att cct act cca ctt att caa tgg ctt aaa gat<br>Cys Asn Ala Asn Gly Ile Pro Thr Pro Leu Ile Gln Trp Leu Lys Asp | 10078 |

-continued

```
              3270                  3275                  3280
gga aag ccc ata gct agt ggt gaa aca gaa aga atc cga gtg agt gca    10126
Gly Lys Pro Ile Ala Ser Gly Glu Thr Glu Arg Ile Arg Val Ser Ala
    3285                  3290                  3295 aat ggc agc aca tta aac att tat gga gct ctt aca tct gac acg ggg    10174
Asn Gly Ser Thr Leu Asn Ile Tyr Gly Ala Leu Thr Ser Asp Thr Gly
3300                  3305                  3310                  3315 aaa tac aca tgt gtt gct act aat ccc gct gga gaa gaa gac cga att    10222
Lys Tyr Thr Cys Val Ala Thr Asn Pro Ala Gly Glu Glu Asp Arg Ile
                3320                  3325                  3330 ttt aac ttg aat gtc tat gtt aca cct aca att agg ggt aat aaa gat    10270
Phe Asn Leu Asn Val Tyr Val Thr Pro Thr Ile Arg Gly Asn Lys Asp
            3335                  3340                  3345 gaa gca gag aaa cta atg act tta gtg gat act tca ata aat att gaa    10318
Glu Ala Glu Lys Leu Met Thr Leu Val Asp Thr Ser Ile Asn Ile Glu
        3350                  3355                  3360 tgc aga gcc aca ggg acg cct cca cca cag ata aac tgg ctg aag aat    10366
Cys Arg Ala Thr Gly Thr Pro Pro Pro Gln Ile Asn Trp Leu Lys Asn
    3365                  3370                  3375 gga ctt cct ctg cct ctc tcc tcc cat atc cgg tta ctg gca gca gga    10414
Gly Leu Pro Leu Pro Leu Ser Ser His Ile Arg Leu Leu Ala Ala Gly
3380                  3385                  3390                  3395 caa gtt atc agg att gtg aga gct cag gtg tct gat gtc gct gtg tat    10462
Gln Val Ile Arg Ile Val Arg Ala Gln Val Ser Asp Val Ala Val Tyr
                3400                  3405                  3410 act tgt gtg gcc tcc aac aga gct ggg gtg gat aat aag cat tac aat    10510
Thr Cys Val Ala Ser Asn Arg Ala Gly Val Asp Asn Lys His Tyr Asn
            3415                  3420                  3425 ctt caa gtg ttt gca cca cca aat atg gac aat tca atg ggg aca gag    10558
Leu Gln Val Phe Ala Pro Pro Asn Met Asp Asn Ser Met Gly Thr Glu
        3430                  3435                  3440 gaa atc aca gtt ctc aaa ggt agt tcc acc tct atg gca tgc att act    10606
Glu Ile Thr Val Leu Lys Gly Ser Ser Thr Ser Met Ala Cys Ile Thr
    3445                  3450                  3455 gat gga acc cca gct ccc agt atg gcc tgg ctt aga gat ggc cag cct    10654
Asp Gly Thr Pro Ala Pro Ser Met Ala Trp Leu Arg Asp Gly Gln Pro
3460                  3465                  3470                  3475 ctg ggg ctt gat gcc cat ctg aca gtc agc acc cat gga atg gtc ctg    10702
Leu Gly Leu Asp Ala His Leu Thr Val Ser Thr His Gly Met Val Leu
                3480                  3485                  3490 cag ctc ctc aaa gca gag act gaa gat tcg gga aag tac acc tgc att    10750
Gln Leu Leu Lys Ala Glu Thr Glu Asp Ser Gly Lys Tyr Thr Cys Ile
            3495                  3500                  3505 gcc tca aat gaa gct gga gaa gtc agc aag cac ttt atc ctc aag gtc    10798
Ala Ser Asn Glu Ala Gly Glu Val Ser Lys His Phe Ile Leu Lys Val
        3510                  3515                  3520 cta gaa cca cct cac att aat gga tct gaa gaa cat gaa gag ata tca    10846
Leu Glu Pro Pro His Ile Asn Gly Ser Glu Glu His Glu Glu Ile Ser
    3525                  3530                  3535 gta att gtt aat aac cca ctt gaa ctt acc tgc att gct tct gga atc    10894
Val Ile Val Asn Asn Pro Leu Glu Leu Thr Cys Ile Ala Ser Gly Ile
3540                  3545                  3550                  3555 cca gcc cct aaa atg acc tgg atg aaa gat ggc cgg ccc ctt cca cag    10942
Pro Ala Pro Lys Met Thr Trp Met Lys Asp Gly Arg Pro Leu Pro Gln
                3560                  3565                  3570 acg gat caa gtg caa act cta gga gga gga gag gtt ctt cga att tct    10990
Thr Asp Gln Val Gln Thr Leu Gly Gly Gly Glu Val Leu Arg Ile Ser
            3575                  3580                  3585 act gct cag gtg gag gat aca gga aga tat aca tgt ctg gca tcc agt    11038
```

```
                Thr Ala Gln Val Glu Asp Thr Gly Arg Tyr Thr Cys Leu Ala Ser Ser
                        3590                3595                3600 cct gca gga gat gat gat aag gaa tat cta gtg aga gtg cat gta cct        11086
Pro Ala Gly Asp Asp Asp Lys Glu Tyr Leu Val Arg Val His Val Pro
    3605                3610                3615 cct aat att gct gga act gat gag ccc cgg gat atc act gtg tta cgg        11134
Pro Asn Ile Ala Gly Thr Asp Glu Pro Arg Asp Ile Thr Val Leu Arg
3620                3625                3630                3635 aac aga caa gtg aca ttg gaa tgc aag tca gat gca gtg ccc cca cct        11182
Asn Arg Gln Val Thr Leu Glu Cys Lys Ser Asp Ala Val Pro Pro Pro
            3640                3645                3650 gta att act tgg ctc aga aat gga gaa cgg tta cag gca aca cct cga        11230
Val Ile Thr Trp Leu Arg Asn Gly Glu Arg Leu Gln Ala Thr Pro Arg
        3655                3660                3665 gtg cga atc cta tct gga ggg aga tac ttg caa atc aac aat gct gac        11278
Val Arg Ile Leu Ser Gly Gly Arg Tyr Leu Gln Ile Asn Asn Ala Asp
    3670                3675                3680 cta ggt gat aca gcc aat tat acc tgt gtt gcc agc aac att gca gga        11326
Leu Gly Asp Thr Ala Asn Tyr Thr Cys Val Ala Ser Asn Ile Ala Gly
3685                3690                3695 aag act aca aga gaa ttt att ctc act gta aat gtt cct cca aac ata        11374
Lys Thr Thr Arg Glu Phe Ile Leu Thr Val Asn Val Pro Pro Asn Ile
3700                3705                3710                3715 aag ggg ggc ccc cag agc ctt gta att ctt tta aat aag tca act gta        11422
Lys Gly Gly Pro Gln Ser Leu Val Ile Leu Leu Asn Lys Ser Thr Val
            3720                3725                3730 ttg gaa tgc atc gct gaa ggt gtg cca act cca agg ata aca tgg aga        11470
Leu Glu Cys Ile Ala Glu Gly Val Pro Thr Pro Arg Ile Thr Trp Arg
        3735                3740                3745 aag gat gga gct gtt cta gct ggg aat cat gca aga tat tcc atc ttg        11518
Lys Asp Gly Ala Val Leu Ala Gly Asn His Ala Arg Tyr Ser Ile Leu
    3750                3755                3760 gaa aat gga ttc ctt cat att caa tca gca cat gtc act gac act gga        11566
Glu Asn Gly Phe Leu His Ile Gln Ser Ala His Val Thr Asp Thr Gly
3765                3770                3775 cgg tat ttg tgt atg gcc acc aat gct gct gga aca gat cgc agg cga        11614
Arg Tyr Leu Cys Met Ala Thr Asn Ala Ala Gly Thr Asp Arg Arg Arg
3780                3785                3790                3795 ata gat tta cag gtc cat gtt cct cca tct att gct ccg ggt cct acc        11662
Ile Asp Leu Gln Val His Val Pro Pro Ser Ile Ala Pro Gly Pro Thr
            3800                3805                3810 aac atg act gta ata gta aat gtt caa act act ctg gct tgt gag gct        11710
Asn Met Thr Val Ile Val Asn Val Gln Thr Thr Leu Ala Cys Glu Ala
        3815                3820                3825 act ggg ata cca aaa cca tca atc aat tgg aga aaa aat ggg cat ctt        11758
Thr Gly Ile Pro Lys Pro Ser Ile Asn Trp Arg Lys Asn Gly His Leu
    3830                3835                3840 ctt aat gtg gat caa aat cag aac tca tac agg ctc ctt tct tca ggt        11806
Leu Asn Val Asp Gln Asn Gln Asn Ser Tyr Arg Leu Leu Ser Ser Gly
3845                3850                3855 tca cta gta att att tcc cct tct gtg gat gac act gca acc tat gaa        11854
Ser Leu Val Ile Ile Ser Pro Ser Val Asp Asp Thr Ala Thr Tyr Glu
3860                3865                3870                3875 tgt act gtg aca aac ggt gct gga gat gat aaa aga act gtg gat ctc        11902
Cys Thr Val Thr Asn Gly Ala Gly Asp Asp Lys Arg Thr Val Asp Leu
            3880                3885                3890 act gtc caa gtt cca cct tcc ata gct gat gag cct aca gat ttc cta        11950
Thr Val Gln Val Pro Pro Ser Ile Ala Asp Glu Pro Thr Asp Phe Leu
        3895                3900                3905
```

```
gta acc aaa cat gcc cca gca gta att acc tgc act gct tcg gga gtt      11998
Val Thr Lys His Ala Pro Ala Val Ile Thr Cys Thr Ala Ser Gly Val
        3910            3915            3920 cca ttt ccc tca att cac tgg acc aaa aat ggt ata aga ctg ctt ccc      12046
Pro Phe Pro Ser Ile His Trp Thr Lys Asn Gly Ile Arg Leu Leu Pro
3925            3930            3935 agg gga gat ggc tat aga att ctg tcc tca gga gca att gaa ata ctt      12094
Arg Gly Asp Gly Tyr Arg Ile Leu Ser Ser Gly Ala Ile Glu Ile Leu
3940            3945            3950                    3955 gcc acc caa tta aac cat gct gga aga tac act tgt gtc gct agg aat      12142
Ala Thr Gln Leu Asn His Ala Gly Arg Tyr Thr Cys Val Ala Arg Asn
            3960            3965            3970 gcg gct ggc tct gca cat cga cac gtg acc ctt cat gtt cat gag cct      12190
Ala Ala Gly Ser Ala His Arg His Val Thr Leu His Val His Glu Pro
            3975            3980            3985 cca gtc att cag ccc caa cca agt gaa cta cac gtc att ctg aac aat      12238
Pro Val Ile Gln Pro Gln Pro Ser Glu Leu His Val Ile Leu Asn Asn
        3990            3995            4000 cct att tta tta cca tgt gaa gca aca ggg aca ccc agt cct ttc att      12286
Pro Ile Leu Leu Pro Cys Glu Ala Thr Gly Thr Pro Ser Pro Phe Ile
4005            4010            4015 act tgg caa aaa gaa ggc atc aat gtt aac act tca ggc aga aac cat      12334
Thr Trp Gln Lys Glu Gly Ile Asn Val Asn Thr Ser Gly Arg Asn His
4020            4025            4030            4035 gca gtt ctt cct agt ggc ggc tta cag atc tcc aga gct gtc cga gag      12382
Ala Val Leu Pro Ser Gly Gly Leu Gln Ile Ser Arg Ala Val Arg Glu
            4040            4045            4050 gat gct ggc act tac atg tgt gtg gcc cag aac ccg gct ggt aca gcc      12430
Asp Ala Gly Thr Tyr Met Cys Val Ala Gln Asn Pro Ala Gly Thr Ala
            4055            4060            4065 ttg ggc aaa atc aag tta aat gtc caa gtt cct cca gtc att agc cct      12478
Leu Gly Lys Ile Lys Leu Asn Val Gln Val Pro Pro Val Ile Ser Pro
        4070            4075            4080 cat cta aag gaa tat gtt att gct gtg gac aag ccc atc acg tta tcc      12526
His Leu Lys Glu Tyr Val Ile Ala Val Asp Lys Pro Ile Thr Leu Ser
        4085            4090            4095 tgt gaa gca gat ggc ctc cct ccg cct gac att aca tgg cat aaa gat      12574
Cys Glu Ala Asp Gly Leu Pro Pro Pro Asp Ile Thr Trp His Lys Asp
4100            4105            4110            4115 ggg cgt gca att gtg gaa tct atc cgc cag cgc gtc ctc agc tct ggc      12622
Gly Arg Ala Ile Val Glu Ser Ile Arg Gln Arg Val Leu Ser Ser Gly
            4120            4125            4130 tct ctg caa ata gca ttt gtc cag cct ggt gat gct ggc cat tac acg      12670
Ser Leu Gln Ile Ala Phe Val Gln Pro Gly Asp Ala Gly His Tyr Thr
            4135            4140            4145 tgc atg gca gcc aat gta gca gga tca agc agc aca agc acc aag ctc      12718
Cys Met Ala Ala Asn Val Ala Gly Ser Ser Ser Thr Ser Thr Lys Leu
            4150            4155            4160 acc gtc cat gta cca ccc agg atc aga agt aca gaa gga cac tac acg      12766
Thr Val His Val Pro Pro Arg Ile Arg Ser Thr Glu Gly His Tyr Thr
            4165            4170            4175 gtc aat gag aat tca caa gcc att ctt cca tgc gta gct gat gga atc      12814
Val Asn Glu Asn Ser Gln Ala Ile Leu Pro Cys Val Ala Asp Gly Ile
4180            4185            4190            4195 ccc aca cca gca att aac tgg aaa aaa gac aat gtt ctt tta gct aac      12862
Pro Thr Pro Ala Ile Asn Trp Lys Lys Asp Asn Val Leu Leu Ala Asn
            4200            4205            4210 ttg tta gga aaa tac act gct gaa cca tat gga gaa ctc att tta gaa      12910
Leu Leu Gly Lys Tyr Thr Ala Glu Pro Tyr Gly Glu Leu Ile Leu Glu
        4215            4220            4225
```

```
                                                           -continued aat gtt gtg ctg gag gat tct ggc ttc tat acc tgt gtt gct aac aat      12958
Asn Val Val Leu Glu Asp Ser Gly Phe Tyr Thr Cys Val Ala Asn Asn
        4230                4235                4240 gct gca ggt gaa gat aca cac act gtc agc ctg act gtg cat gtt ctc      13006
Ala Ala Gly Glu Asp Thr His Thr Val Ser Leu Thr Val His Val Leu
    4245                4250                4255 ccc act ttt act gaa ctt cct gga gac gtg tca tta aat aaa gga gaa      13054
Pro Thr Phe Thr Glu Leu Pro Gly Asp Val Ser Leu Asn Lys Gly Glu
4260                4265                4270                4275 cag cta cga tta agc tgt aaa gct act ggt att cca ttg ccc aaa tta      13102
Gln Leu Arg Leu Ser Cys Lys Ala Thr Gly Ile Pro Leu Pro Lys Leu
            4280                4285                4290 aca tgg acc ttc aat aac aat att att cca gcc cac ttt gac agt gtg      13150
Thr Trp Thr Phe Asn Asn Asn Ile Ile Pro Ala His Phe Asp Ser Val
        4295                4300                4305 aat gga cac agt gaa ctt gtt att gaa aga gtg tca aaa gag gat tca      13198
Asn Gly His Ser Glu Leu Val Ile Glu Arg Val Ser Lys Glu Asp Ser
    4310                4315                4320 ggt act tat gtg tgc acc gca gag aac agc gtt ggc ttt gtg aag gca      13246
Gly Thr Tyr Val Cys Thr Ala Glu Asn Ser Val Gly Phe Val Lys Ala
4325                4330                4335 att gga ttt gtt tat gtg aaa gaa cct cca gtc ttc aaa ggt gat tat      13294
Ile Gly Phe Val Tyr Val Lys Glu Pro Pro Val Phe Lys Gly Asp Tyr
4340                4345                4350                4355 cct tct aac tgg att gaa cca ctt ggt ggg aat gca atc ctg aat tgt      13342
Pro Ser Asn Trp Ile Glu Pro Leu Gly Gly Asn Ala Ile Leu Asn Cys
            4360                4365                4370 gag gtg aaa gga gac ccc acc cca acc atc cag tgg aac aga aag gga      13390
Glu Val Lys Gly Asp Pro Thr Pro Thr Ile Gln Trp Asn Arg Lys Gly
        4375                4380                4385 gtg gat att gaa att agc cac aga atc cgg caa ctg ggc aat ggc tcc      13438
Val Asp Ile Glu Ile Ser His Arg Ile Arg Gln Leu Gly Asn Gly Ser
    4390                4395                4400 ctg gcc atc tat ggc act gtt aat gaa gat gcc ggt gac tat aca tgt      13486
Leu Ala Ile Tyr Gly Thr Val Asn Glu Asp Ala Gly Asp Tyr Thr Cys
4405                4410                4415 gta gct acc aat gaa gct ggg gtg gtg gag cgc agc atg agt ctg act      13534
Val Ala Thr Asn Glu Ala Gly Val Val Glu Arg Ser Met Ser Leu Thr
4420                4425                4430                4435 ctg caa agt cct cct att atc act ctt gag cca gtg gaa act gtt att      13582
Leu Gln Ser Pro Pro Ile Ile Thr Leu Glu Pro Val Glu Thr Val Ile
            4440                4445                4450 aat gct ggt ggc aaa atc ata ttg aat tgt cag gca act gga gag cct      13630
Asn Ala Gly Gly Lys Ile Ile Leu Asn Cys Gln Ala Thr Gly Glu Pro
        4455                4460                4465 caa cca acc att aca tgg tcc cgt caa ggg cac tct att tcc tgg gat      13678
Gln Pro Thr Ile Thr Trp Ser Arg Gln Gly His Ser Ile Ser Trp Asp
    4470                4475                4480 gac cgg gtt aac gtg ttg tcc aac aac tca tta tat att gct gat gct      13726
Asp Arg Val Asn Val Leu Ser Asn Asn Ser Leu Tyr Ile Ala Asp Ala
4485                4490                4495 cag aaa gaa gat acc tct gaa ttt gaa tgt gtt gct cga aac tta atg      13774
Gln Lys Glu Asp Thr Ser Glu Phe Glu Cys Val Ala Arg Asn Leu Met
4500                4505                4510                4515 ggt tct gtc ctt gtc aga gtg cca gtc ata gtc agg gtt cat ggt gga      13822
Gly Ser Val Leu Val Arg Val Pro Val Ile Val Gln Val His Gly Gly
            4520                4525                4530 ttt tcc cag tgg tct gca tgg aga gcc tgc agt gtc acc tgt gga aaa      13870
Phe Ser Gln Trp Ser Ala Trp Arg Ala Cys Ser Val Thr Cys Gly Lys
```

-continued

|  | | |
|---|---|---|
| ggc atc caa aag agg agt cgt ctg tgc aac cag ccc ctt cca gcc aat<br>Gly Ile Gln Lys Arg Ser Arg Leu Cys Asn Gln Pro Leu Pro Ala Asn<br>       4550                    4555                    4560 | 13918 |
| ggt ggg aag ccc tgc caa ggt tca gat ttg gaa atg cga aac tgt caa<br>Gly Gly Lys Pro Cys Gln Gly Ser Asp Leu Glu Met Arg Asn Cys Gln<br>       4565                    4570                    4575 | 13966 |
| aat aag cct tgt cca gtg gat ggt agc tgg tcg gaa tgg agt ctt tgg<br>Asn Lys Pro Cys Pro Val Asp Gly Ser Trp Ser Glu Trp Ser Leu Trp<br>4580                    4585                    4590                    4595 | 14014 |
| gaa gaa tgc aca agg agc tgt gga cgc ggc aac caa acc agg acc agg<br>Glu Glu Cys Thr Arg Ser Cys Gly Arg Gly Asn Gln Thr Arg Thr Arg<br>                    4600                    4605                    4610 | 14062 |
| act tgc aat aat cca tca gtt cag cat ggt ggg cgg cca tgt gaa ggg<br>Thr Cys Asn Asn Pro Ser Val Gln His Gly Gly Arg Pro Cys Glu Gly<br>       4615                    4620                    4625 | 14110 |
| aat gct gtg gaa ata att atg tgc aac att agg cct tgc cca gtt cat<br>Asn Ala Val Glu Ile Ile Met Cys Asn Ile Arg Pro Cys Pro Val His<br>       4630                    4635                    4640 | 14158 |
| gga gca tgg agc gct tgg cag cct tgg gga aca tgc agc gaa agt tgt<br>Gly Ala Trp Ser Ala Trp Gln Pro Trp Gly Thr Cys Ser Glu Ser Cys<br>       4645                    4650                    4655 | 14206 |
| ggg aaa ggt act cag aca aga gca aga ctt tgt aat aac cca cca cca<br>Gly Lys Gly Thr Gln Thr Arg Ala Arg Leu Cys Asn Asn Pro Pro Pro<br>4660                    4665                    4670                    4675 | 14254 |
| gcg ttt ggt ggg tcc tac tgt gat gga gca gaa aca cag atg caa gtt<br>Ala Phe Gly Gly Ser Tyr Cys Asp Gly Ala Glu Thr Gln Met Gln Val<br>                    4680                    4685                    4690 | 14302 |
| tgc aat gaa aga aat tgt cca att cat ggc aag tgg gcg act tgg gcc<br>Cys Asn Glu Arg Asn Cys Pro Ile His Gly Lys Trp Ala Thr Trp Ala<br>       4695                    4700                    4705 | 14350 |
| agt tgg agt gcc tgt tct gtg tca tgt gga gga ggt gcc aga cag aga<br>Ser Trp Ser Ala Cys Ser Val Ser Cys Gly Gly Gly Ala Arg Gln Arg<br>       4710                    4715                    4720 | 14398 |
| aca agg ggc tgc tcc gac cct gtg ccc cag tat gga gga agg aaa tgc<br>Thr Arg Gly Cys Ser Asp Pro Val Pro Gln Tyr Gly Gly Arg Lys Cys<br>       4725                    4730                    4735 | 14446 |
| gaa ggg agt gat gtc cag agt gat ttt tgc aac agt gac cct tgc cca<br>Glu Gly Ser Asp Val Gln Ser Asp Phe Cys Asn Ser Asp Pro Cys Pro<br>4740                    4745                    4750                    4755 | 14494 |
| acc cat ggt aac tgg agt cct tgg agt ggc tgg gga aca tgc agc cgg<br>Thr His Gly Asn Trp Ser Pro Trp Ser Gly Trp Gly Thr Cys Ser Arg<br>                    4760                    4765                    4770 | 14542 |
| acg tgt aac gga ggg cag atg cgg cgg tac cgc aca tgt gat aac cct<br>Thr Cys Asn Gly Gly Gln Met Arg Arg Tyr Arg Thr Cys Asp Asn Pro<br>       4775                    4780                    4785 | 14590 |
| cct ccc tcc aat ggg gga aga gct tgt ggg gga cca gac tcc cag atc<br>Pro Pro Ser Asn Gly Gly Arg Ala Cys Gly Gly Pro Asp Ser Gln Ile<br>       4790                    4795                    4800 | 14638 |
| cag agg tgc aac act gac atg tgt cct gtg gat gga agt tgg gga agc<br>Gln Arg Cys Asn Thr Asp Met Cys Pro Val Asp Gly Ser Trp Gly Ser<br>       4805                    4810                    4815 | 14686 |
| tgg cat agt tgg agc cag tgc tct gcc tcc tgt gga gga ggt gaa aag<br>Trp His Ser Trp Ser Gln Cys Ser Ala Ser Cys Gly Gly Gly Glu Lys<br>4820                    4825                    4830                    4835 | 14734 |
| act cgg aag cgg ctg tgc gac cat cct gtg cca gtt aaa ggt ggc cgt<br>Thr Arg Lys Arg Leu Cys Asp His Pro Val Pro Val Lys Gly Gly Arg<br>                    4840                    4845                    4850 | 14782 |
| ccc tgt ccc gga gac act act cag gtg acc agg tgc aat gta caa gca | 14830 |

```
Pro Cys Pro Gly Asp Thr Thr Gln Val Thr Arg Cys Asn Val Gln Ala
            4855                4860                4865 tgt cca ggt ggg ccc cag cga gcc aga gga agt gtt att gga aat att    14878
Cys Pro Gly Gly Pro Gln Arg Ala Arg Gly Ser Val Ile Gly Asn Ile
        4870                4875                4880 aat gat gtt gaa ttt gga att gct ttc ctt aat gcc aca ata act gat    14926
Asn Asp Val Glu Phe Gly Ile Ala Phe Leu Asn Ala Thr Ile Thr Asp
        4885                4890                4895 agc cct aac tct gat act aga ata ata cgt gcc aaa att acc aat gta    14974
Ser Pro Asn Ser Asp Thr Arg Ile Ile Arg Ala Lys Ile Thr Asn Val
4900            4905                4910                4915 cct cgt agt ctt ggt tca gca atg aga aag ata gtt tct att cta aat    15022
Pro Arg Ser Leu Gly Ser Ala Met Arg Lys Ile Val Ser Ile Leu Asn
            4920                4925                4930 ccc att tat tgg aca aca gca aag gaa ata gga gaa gca gtc aat ggc    15070
Pro Ile Tyr Trp Thr Thr Ala Lys Glu Ile Gly Glu Ala Val Asn Gly
            4935                4940                4945 ttt acc ctc acc aat gca gtc ttc aaa aga gaa act caa gtg gaa ttt    15118
Phe Thr Leu Thr Asn Ala Val Phe Lys Arg Glu Thr Gln Val Glu Phe
            4950                4955                4960 gca act gga gaa atc ttg cag atg agt cat att gcc cgg ggc ttg gat    15166
Ala Thr Gly Glu Ile Leu Gln Met Ser His Ile Ala Arg Gly Leu Asp
        4965                4970                4975 tcc gat ggt tct ttg ctg cta gat atc gtt gtg agt ggc tat gtc cta    15214
Ser Asp Gly Ser Leu Leu Leu Asp Ile Val Val Ser Gly Tyr Val Leu
4980            4985                4990                4995 cag ctt cag tca cct gct gaa gtc act gta aag gat tac aca gag gac    15262
Gln Leu Gln Ser Pro Ala Glu Val Thr Val Lys Asp Tyr Thr Glu Asp
                5000                5005                5010 tac att caa aca ggt cct ggg cag ctg tac gcc tac tca acc cgg ctg    15310
Tyr Ile Gln Thr Gly Pro Gly Gln Leu Tyr Ala Tyr Ser Thr Arg Leu
            5015                5020                5025 ttc acc att gat ggc atc agc atc cca tac aca tgg aac cac acc gtt    15358
Phe Thr Ile Asp Gly Ile Ser Ile Pro Tyr Thr Trp Asn His Thr Val
            5030                5035                5040 ttc tat gat cag gca cag gga aga atg cct ttc ttg gtt gaa aca ctt    15406
Phe Tyr Asp Gln Ala Gln Gly Arg Met Pro Phe Leu Val Glu Thr Leu
            5045                5050                5055 cat gca tcc tct gtg gaa tct gac tat aac cag ata gaa gag aca ctg    15454
His Ala Ser Ser Val Glu Ser Asp Tyr Asn Gln Ile Glu Glu Thr Leu
5060            5065                5070                5075 ggt ttt aaa att cat gct tca ata tcc aaa gga gat cgc agt aat cag    15502
Gly Phe Lys Ile His Ala Ser Ile Ser Lys Gly Asp Arg Ser Asn Gln
            5080                5085                5090 tgc ccc tcc ggg ttt acc tta gac tca gtt gga cct ttt tgt gct gat    15550
Cys Pro Ser Gly Phe Thr Leu Asp Ser Val Gly Pro Phe Cys Ala Asp
        5095                5100                5105 gag gat gaa tgt gca gca ggg aat ccc tgc tcc cat agc tgc cac aat    15598
Glu Asp Glu Cys Ala Ala Gly Asn Pro Cys Ser His Ser Cys His Asn
            5110                5115                5120 gcc atg ggg act tac tac tgc tcc tgc cct aaa ggc ctc acc ata gct    15646
Ala Met Gly Thr Tyr Tyr Cys Ser Cys Pro Lys Gly Leu Thr Ile Ala
            5125                5130                5135 gca gat gga aga act tgt caa gat att gat gag tgt gct ttg ggt agg    15694
Ala Asp Gly Arg Thr Cys Gln Asp Ile Asp Glu Cys Ala Leu Gly Arg
5140            5145                5150                5155 cat acc tgc cac gct ggt cag gac tgt gac aat acg att gga tct tat    15742
His Thr Cys His Ala Gly Gln Asp Cys Asp Asn Thr Ile Gly Ser Tyr
        5160                5165                5170
```

```
cgc tgt gtg gtc cgt tgt gga agt ggc ttt cga aga acc tct gat ggg   15790
Arg Cys Val Val Arg Cys Gly Ser Gly Phe Arg Arg Thr Ser Asp Gly
        5175                5180                5185 ctg agt tgt caa gat att aat gaa tgt caa gaa tcc agc ccc tgt cac   15838
Leu Ser Cys Gln Asp Ile Asn Glu Cys Gln Glu Ser Ser Pro Cys His
            5190                5195                5200 cag cgc tgt ttc aat gcc ata gga agt ttc cat tgt gga tgt gaa cct   15886
Gln Arg Cys Phe Asn Ala Ile Gly Ser Phe His Cys Gly Cys Glu Pro
    5205                5210                5215 ggg tat cag ctc aaa ggc aga aaa tgc atg gat gtg aac gag tgt aga   15934
Gly Tyr Gln Leu Lys Gly Arg Lys Cys Met Asp Val Asn Glu Cys Arg
5220                5225                5230                5235 caa aat gta tgc aga cca gat cag cac tgt aag aac acc cgt ggt ggc   15982
Gln Asn Val Cys Arg Pro Asp Gln His Cys Lys Asn Thr Arg Gly Gly
                5240                5245                5250 tat aag tgc att gat ctt tgt cca aat gga atg acc aag gca gaa aat   16030
Tyr Lys Cys Ile Asp Leu Cys Pro Asn Gly Met Thr Lys Ala Glu Asn
        5255                5260                5265 gga acc tgt att gat att gat gaa tgt aaa gat ggg acc cat cag tgc   16078
Gly Thr Cys Ile Asp Ile Asp Glu Cys Lys Asp Gly Thr His Gln Cys
            5270                5275                5280 aga tat aac cag ata tgt gag aat aca aga ggc agc tat cgt tgt gta   16126
Arg Tyr Asn Gln Ile Cys Glu Asn Thr Arg Gly Ser Tyr Arg Cys Val
    5285                5290                5295 tgc cca aga ggt tat cgg tct caa gga gtt gga aga ccc tgc atg gac   16174
Cys Pro Arg Gly Tyr Arg Ser Gln Gly Val Gly Arg Pro Cys Met Asp
5300                5305                5310                5315 att aat gaa tgt gaa caa gtg cct aaa cct tgt gca cat cag tgc tcc   16222
Ile Asn Glu Cys Glu Gln Val Pro Lys Pro Cys Ala His Gln Cys Ser
                5320                5325                5330 aac acc ccc ggc agc ttc aag tgt atc tgt cca cca gga caa cat tta   16270
Asn Thr Pro Gly Ser Phe Lys Cys Ile Cys Pro Pro Gly Gln His Leu
        5335                5340                5345 tta ggg gac ggg aaa tct tgc gct gga ttg gag agg ctg cca aat tat   16318
Leu Gly Asp Gly Lys Ser Cys Ala Gly Leu Glu Arg Leu Pro Asn Tyr
            5350                5355                5360 ggc act caa tac agt agc tat aac ctt gca cgg ttc tcc cct gtg aga   16366
Gly Thr Gln Tyr Ser Ser Tyr Asn Leu Ala Arg Phe Ser Pro Val Arg
    5365                5370                5375 aac aac tat caa cct caa cag cat tac aga cag tac tca cat ctc tac   16414
Asn Asn Tyr Gln Pro Gln Gln His Tyr Arg Gln Tyr Ser His Leu Tyr
5380                5385                5390                5395 agc tcc tac tca gag tat aga aac agc aga aca tct ctc tcc agg act   16462
Ser Ser Tyr Ser Glu Tyr Arg Asn Ser Arg Thr Ser Leu Ser Arg Thr
                5400                5405                5410 aga agg act att agg aaa act tgc cct gaa ggc tct gag gca agc cat   16510
Arg Arg Thr Ile Arg Lys Thr Cys Pro Glu Gly Ser Glu Ala Ser His
        5415                5420                5425 gac aca tgt gta gat att gat gaa tgt gaa aat aca gat gcc tgc cag   16558
Asp Thr Cys Val Asp Ile Asp Glu Cys Glu Asn Thr Asp Ala Cys Gln
            5430                5435                5440 cat gag tgt aag aat acc ttt gga agt tat cag tgc atc tgc cca cct   16606
His Glu Cys Lys Asn Thr Phe Gly Ser Tyr Gln Cys Ile Cys Pro Pro
    5445                5450                5455 ggc tat caa ctc aca cac aat gga aag aca tgc caa gat atc gat gaa   16654
Gly Tyr Gln Leu Thr His Asn Gly Lys Thr Cys Gln Asp Ile Asp Glu
5460                5465                5470                5475 tgt ctg gag cag aat gtg cac tgt gga ccc aat cgc atg tgc ttc aac   16702
Cys Leu Glu Gln Asn Val His Cys Gly Pro Asn Arg Met Cys Phe Asn
                5480                5485                5490
```

```
atg aga gga agc tac cag tgc atc gat aca ccc tgt cca ccc aac tac        16750
Met Arg Gly Ser Tyr Gln Cys Ile Asp Thr Pro Cys Pro Pro Asn Tyr
        5495                5500                5505 caa cgg gat cct gtt tca ggg ttc tgc ctc aag aac tgt cca ccc aat        16798
Gln Arg Asp Pro Val Ser Gly Phe Cys Leu Lys Asn Cys Pro Pro Asn
            5510                5515                5520 gat ttg gaa tgt gcc ttg agc cca tat gcc ttg gaa tac aaa ctc gtc        16846
Asp Leu Glu Cys Ala Leu Ser Pro Tyr Ala Leu Glu Tyr Lys Leu Val
        5525                5530                5535 tcc ctc cca ttt gga ata gcc acc aat caa gat tta atc cgg ctg gtt        16894
Ser Leu Pro Phe Gly Ile Ala Thr Asn Gln Asp Leu Ile Arg Leu Val
5540                5545                5550                5555 gca tac aca cag gat gga gtg atg cat ccc agg aca act ttc ctc atg        16942
Ala Tyr Thr Gln Asp Gly Val Met His Pro Arg Thr Thr Phe Leu Met
        5560                5565                5570 gta gat gag gaa cag act gtt cct ttt gcc ttg agg gat gaa aac ctg        16990
Val Asp Glu Glu Gln Thr Val Pro Phe Ala Leu Arg Asp Glu Asn Leu
        5575                5580                5585 aaa gga gtg gtg tat aca aca cga cca cta cga gaa gca gag acc tac        17038
Lys Gly Val Val Tyr Thr Thr Arg Pro Leu Arg Glu Ala Glu Thr Tyr
            5590                5595                5600 cgc atg agg gtc cga gcc tca tcc tac agt gcc aat ggg acc att gaa        17086
Arg Met Arg Val Arg Ala Ser Ser Tyr Ser Ala Asn Gly Thr Ile Glu
        5605                5610                5615 tat cag acc aca ttc ata gtt tat ata gct gtg tcc gcc tat cca tac        17134
Tyr Gln Thr Thr Phe Ile Val Tyr Ile Ala Val Ser Ala Tyr Pro Tyr
5620                5625                5630                5635 taa ggaactctcc aaagcctatt ccacatattt aaaccgcatt aatcatggca             17187
* atcaagcccc cttccagatt actgtctctt gaacagttgc aatcttggca gcttgaaaat      17247
ggtgctacac tctgttttgt gtgccttcct tggtacttct gaggtatttt catgatccca      17307
ccatggtcat atcttgaagt atggtctaga aaagtccctt attatttat ttattacact       17367 ggagcagtta cttcccaaag attattctga acatctaaca ggacatatca gtgatggttt      17427
acagtagtgt agtacctaag atcatttcc tgaaagccaa accaaacaac gaaaacaag        17487 aacaactaat tcagaatcaa atagagtttt tgagcatttg actattttta gaatcataaa     17547
attagttact aagtattttg atcaaagctt ataaaataac ttacggagat ttttgtaagt     17607
attgatacat tataatagga cttgcctatt tcattttta agaagaaaaa caccactcat      17667
tttataaaat atagtacagc tactataagg cttgtttgat cccaaatggt gcttatcttg     17727
attgaacatt cagaacaagg atattatttt cagtgatttt gtgagatcag ctgaaccact     17787
tatgataata ataataaaaa agactgcttt gccctcacgt cagttgtaca tggcatggaa     17847
ctttaaaaat tttaatataa actttcatcc agttagcttc ataactttta cgttccagaa     17907
ttttgtttat tttcctgtca atgaaagcaa ttttaaaga taccagtggg acagatttgg     17967
ttttttaaaa atctcatgtg ttcaaattaa cataaatatt acacgtcaat acactgtaca     18027
tggtggtaat agactctaag caattgccaa gatgtattct atttttatga agtgtatata     18087
tattacctta gtgtgcattt tctatataat atcttgatgg actctttat aaaattattt     18147 tataaaaaac aatgttacac taaaatcagc ctaaataaat tttcacaact tttttcat     18206

<210> SEQ ID NO 2
<211> LENGTH: 5635
<212> TYPE: PRT
<213> ORGANISM: Homo sapiens
```

```
<400> SEQUENCE: 2

Met Ile Ser Trp Glu Val Val His Thr Val Phe Leu Phe Ala Leu Leu
 1               5                  10                  15

Tyr Ser Ser Leu Ala Gln Asp Ala Ser Pro Gln Ser Glu Ile Arg Ala
            20                  25                  30

Glu Glu Ile Pro Glu Gly Ala Ser Thr Leu Ala Phe Val Phe Asp Val
        35                  40                  45

Thr Gly Ser Met Tyr Asp Asp Leu Val Gln Val Ile Glu Gly Ala Ser
50                  55                  60

Lys Ile Leu Glu Thr Ser Leu Lys Arg Pro Lys Arg Pro Leu Phe Asn
65                  70                  75                  80

Phe Ala Leu Val Pro Phe His Asp Pro Glu Ile Gly Pro Val Thr Ile
                85                  90                  95

Thr Thr Asp Pro Lys Lys Phe Gln Tyr Glu Leu Arg Glu Leu Tyr Val
            100                 105                 110

Gln Gly Gly Gly Asp Cys Pro Glu Met Ser Ile Gly Ala Ile Lys Ile
        115                 120                 125

Ala Leu Glu Ile Ser Leu Pro Gly Ser Phe Ile Tyr Val Phe Thr Asp
130                 135                 140

Ala Arg Ser Lys Asp Tyr Arg Leu Thr His Glu Val Leu Gln Leu Ile
145                 150                 155                 160

Gln Gln Lys Gln Ser Gln Val Val Phe Val Leu Thr Gly Asp Cys Asp
                165                 170                 175

Asp Arg Thr His Ile Gly Tyr Lys Val Tyr Glu Ile Ala Ser Thr
            180                 185                 190

Ser Ser Gly Gln Val Phe His Leu Asp Lys Lys Gln Val Asn Glu Val
        195                 200                 205

Leu Lys Trp Val Glu Glu Ala Val Gln Ala Ser Lys Val His Leu Leu
210                 215                 220

Ser Thr Asp His Leu Glu Gln Ala Val Asn Thr Trp Arg Ile Pro Phe
225                 230                 235                 240

Asp Pro Ser Leu Lys Glu Val Thr Val Ser Leu Ser Gly Pro Ser Pro
                245                 250                 255

Met Ile Glu Ile Arg Asn Pro Leu Gly Lys Leu Ile Lys Lys Gly Phe
            260                 265                 270

Gly Leu His Glu Leu Leu Asn Ile His Asn Ser Ala Lys Val Val Asn
        275                 280                 285

Val Lys Glu Pro Glu Ala Gly Met Trp Thr Val Lys Thr Ser Ser Ser
290                 295                 300

Gly Arg His Ser Val Arg Ile Thr Gly Leu Ser Thr Ile Asp Phe Arg
305                 310                 315                 320

Ala Gly Phe Ser Arg Lys Pro Thr Leu Asp Phe Lys Lys Thr Val Ser
                325                 330                 335

Arg Pro Val Gln Gly Ile Pro Thr Tyr Val Leu Leu Asn Thr Ser Gly
            340                 345                 350

Ile Ser Thr Pro Ala Arg Ile Asp Leu Leu Glu Leu Leu Ser Ile Ser
        355                 360                 365

Gly Ser Ser Leu Lys Thr Ile Pro Val Lys Tyr Tyr Pro His Arg Lys
370                 375                 380

Pro Tyr Gly Ile Trp Asn Ile Ser Asp Phe Val Pro Pro Asn Glu Ala
385                 390                 395                 400

Phe Phe Leu Lys Val Thr Gly Tyr Asp Lys Asp Asp Tyr Leu Phe Gln
```

-continued

```
                405                 410                 415
Arg Val Ser Ser Val Ser Phe Ser Ile Val Pro Asp Ala Pro Lys
                420                 425                 430
Val Thr Met Pro Glu Lys Thr Pro Gly Tyr Tyr Leu Gln Pro Gly Gln
            435                 440                 445
Ile Pro Cys Ser Val Asp Ser Leu Leu Pro Phe Thr Leu Ser Phe Val
        450                 455                 460
Arg Asn Gly Val Thr Leu Gly Val Asp Gln Tyr Leu Lys Glu Ser Ala
465                 470                 475                 480
Ser Val Asn Leu Asp Ile Ala Lys Val Thr Leu Ser Asp Glu Gly Phe
                485                 490                 495
Tyr Glu Cys Ile Ala Val Ser Ser Ala Gly Thr Gly Arg Ala Gln Thr
                500                 505                 510
Phe Phe Asp Val Ser Glu Pro Pro Val Ile Gln Val Pro Asn Asn
        515                 520                 525
Val Thr Val Thr Pro Gly Glu Arg Ala Val Leu Thr Cys Leu Ile Ile
        530                 535                 540
Ser Ala Val Asp Tyr Asn Leu Thr Trp Gln Arg Asn Asp Arg Asp Val
545                 550                 555                 560
Arg Leu Ala Glu Pro Ala Arg Ile Arg Thr Leu Ala Asn Leu Ser Leu
                565                 570                 575
Glu Leu Lys Ser Val Lys Phe Asn Asp Ala Gly Glu Tyr His Cys Met
                580                 585                 590
Val Ser Ser Glu Gly Gly Ser Ser Ala Ala Ser Val Phe Leu Thr Val
                595                 600                 605
Gln Glu Pro Pro Lys Val Thr Val Met Pro Lys Asn Gln Ser Phe Thr
        610                 615                 620
Gly Gly Ser Glu Val Ser Ile Met Cys Ser Ala Thr Gly Tyr Pro Lys
625                 630                 635                 640
Pro Lys Ile Ala Trp Thr Val Asn Asp Met Phe Ile Val Gly Ser His
                645                 650                 655
Arg Tyr Arg Met Thr Ser Asp Gly Thr Leu Phe Ile Lys Asn Ala Ala
                660                 665                 670
Pro Lys Asp Ala Gly Ile Tyr Gly Cys Leu Ala Ser Asn Ser Ala Gly
        675                 680                 685
Thr Asp Lys Gln Asn Ser Thr Leu Arg Tyr Ile Glu Ala Pro Lys Leu
        690                 695                 700
Met Val Val Gln Ser Glu Leu Leu Val Ala Leu Gly Asp Ile Thr Val
705                 710                 715                 720
Met Glu Cys Lys Thr Ser Gly Ile Pro Pro Pro Gln Val Lys Trp Phe
                725                 730                 735
Lys Gly Asp Leu Glu Leu Arg Pro Ser Thr Phe Leu Ile Ile Asp Pro
                740                 745                 750
Leu Leu Gly Leu Leu Lys Ile Gln Glu Thr Gln Asp Leu Asp Ala Gly
                755                 760                 765
Asp Tyr Thr Cys Val Ala Ile Asn Glu Ala Gly Arg Ala Thr Gly Lys
        770                 775                 780
Ile Thr Leu Asp Val Gly Ser Pro Val Phe Ile Gln Glu Pro Ala
785                 790                 795                 800
Asp Val Ser Met Glu Ile Gly Ser Asn Val Thr Leu Pro Cys Tyr Val
                805                 810                 815
Gln Gly Tyr Pro Glu Pro Thr Ile Lys Trp Arg Arg Leu Asp Asn Met
        820                 825                 830
```

-continued

```
Pro Ile Phe Ser Arg Pro Phe Ser Val Ser Ser Ile Ser Gln Leu Arg
        835                 840                 845

Thr Gly Ala Leu Phe Ile Leu Asn Leu Trp Ala Ser Asp Lys Gly Thr
    850                 855                 860

Tyr Ile Cys Glu Ala Glu Asn Gln Phe Gly Lys Ile Gln Ser Glu Thr
865                 870                 875                 880

Thr Val Thr Val Thr Gly Leu Val Ala Pro Leu Ile Gly Ile Ser Pro
                885                 890                 895

Ser Val Ala Asn Val Ile Glu Gly Gln Gln Leu Thr Leu Pro Cys Thr
            900                 905                 910

Leu Leu Ala Gly Asn Pro Ile Pro Glu Arg Arg Trp Ile Lys Asn Ser
        915                 920                 925

Ala Met Leu Leu Gln Asn Pro Tyr Ile Thr Val Arg Ser Asp Gly Ser
    930                 935                 940

Leu His Ile Glu Arg Val Gln Leu Gln Asp Gly Gly Glu Tyr Thr Cys
945                 950                 955                 960

Val Ala Ser Asn Val Ala Gly Thr Asn Asn Lys Thr Thr Ser Val Val
                965                 970                 975

Val His Val Leu Pro Thr Ile Gln His Gly Gln Gln Ile Leu Ser Thr
            980                 985                 990

Ile Glu Gly Ile Pro Val Thr Leu Pro Cys Lys Ala Ser Gly Asn Pro
        995                 1000                1005

Lys Pro Ser Val Ile Trp Ser Lys Lys Gly Glu Leu Ile Ser Thr Ser
    1010                1015                1020

Ser Ala Lys Phe Ser Ala Gly Ala Asp Gly Ser Leu Tyr Val Val Ser
1025                1030                1035                1040

Pro Gly Gly Glu Glu Ser Gly Glu Tyr Val Cys Thr Ala Thr Asn Thr
                1045                1050                1055

Ala Gly Tyr Ala Lys Arg Lys Val Gln Leu Thr Val Tyr Val Arg Pro
            1060                1065                1070

Arg Val Phe Gly Asp Gln Arg Gly Leu Ser Gln Asp Lys Pro Val Glu
        1075                1080                1085

Ile Ser Val Leu Ala Gly Glu Glu Val Thr Leu Pro Cys Glu Val Lys
    1090                1095                1100

Ser Leu Pro Pro Pro Ile Ile Thr Trp Ala Lys Glu Thr Gln Leu Ile
1105                1110                1115                1120

Ser Pro Phe Ser Pro Arg His Thr Phe Leu Pro Ser Gly Ser Met Lys
                1125                1130                1135

Ile Thr Glu Thr Arg Thr Ser Asp Ser Gly Met Tyr Leu Cys Val Ala
            1140                1145                1150

Thr Asn Ile Ala Gly Asn Val Thr Gln Ala Val Lys Leu Asn Val His
        1155                1160                1165

Val Pro Pro Lys Ile Gln Arg Gly Pro Lys His Leu Lys Val Gln Val
    1170                1175                1180

Gly Gln Arg Val Asp Ile Pro Cys Asn Ala Gln Gly Thr Pro Leu Pro
1185                1190                1195                1200

Val Ile Thr Trp Ser Lys Gly Gly Ser Thr Met Leu Val Asp Gly Glu
                1205                1210                1215

His His Val Ser Asn Pro Asp Gly Thr Leu Ser Ile Asp Gln Ala Thr
            1220                1225                1230

Pro Ser Asp Ala Gly Ile Tyr Thr Cys Val Ala Thr Asn Ile Ala Gly
        1235                1240                1245
```

```
Thr Asp Glu Thr Glu Ile Thr Leu His Val Gln Glu Pro Pro Thr Val
    1250                1255                1260

Glu Asp Leu Glu Pro Pro Tyr Asn Thr Thr Phe Gln Glu Arg Val Ala
1265                1270                1275                1280

Asn Gln Arg Ile Glu Phe Pro Cys Pro Ala Lys Gly Thr Pro Lys Pro
                1285                1290                1295

Thr Ile Lys Trp Leu His Asn Gly Arg Glu Leu Thr Gly Arg Glu Pro
            1300                1305                1310

Gly Ile Ser Ile Leu Glu Asp Gly Thr Leu Leu Val Ile Ala Ser Val
        1315                1320                1325

Thr Pro Tyr Asp Asn Gly Glu Tyr Ile Cys Val Ala Val Asn Glu Ala
    1330                1335                1340

Gly Thr Thr Glu Arg Lys Tyr Asn Leu Lys Val His Val Pro Pro Val
1345                1350                1355                1360

Ile Lys Asp Lys Glu Gln Val Thr Asn Val Ser Val Leu Leu Asn Gln
                1365                1370                1375

Leu Thr Asn Leu Phe Cys Glu Val Glu Gly Thr Pro Ser Pro Ile Ile
            1380                1385                1390

Met Trp Tyr Lys Asp Asn Val Gln Val Thr Glu Ser Ser Thr Ile Gln
        1395                1400                1405

Thr Val Asn Asn Gly Lys Ile Leu Lys Leu Phe Arg Ala Thr Pro Glu
    1410                1415                1420

Asp Ala Gly Arg Tyr Ser Cys Lys Ala Ile Asn Ile Ala Gly Thr Ser
1425                1430                1435                1440

Gln Lys Tyr Phe Asn Ile Asp Val Leu Val Pro Pro Thr Ile Ile Gly
                1445                1450                1455

Thr Asn Phe Pro Asn Glu Val Ser Val Val Leu Asn Arg Asp Val Ala
            1460                1465                1470

Leu Glu Cys Gln Val Lys Gly Thr Pro Phe Pro Asp Ile His Trp Phe
        1475                1480                1485

Lys Asp Gly Lys Pro Leu Phe Leu Gly Asp Pro Asn Val Glu Leu Leu
    1490                1495                1500

Asp Arg Gly Gln Val Leu His Leu Lys Asn Ala Arg Arg Asn Asp Lys
1505                1510                1515                1520

Gly Arg Tyr Gln Cys Thr Val Ser Asn Ala Ala Gly Lys Gln Ala Lys
                1525                1530                1535

Asp Ile Lys Leu Thr Ile Tyr Asn Pro Pro Ser Ile Lys Gly Gly Asn
            1540                1545                1550

Val Thr Thr Asp Ile Ser Val Leu Ile Asn Ser Leu Ile Lys Leu Glu
        1555                1560                1565

Cys Glu Thr Arg Gly Leu Pro Met Pro Ala Ile Thr Trp Tyr Lys Asp
    1570                1575                1580

Gly Gln Pro Ile Met Ser Ser Ser Gln Ala Leu Tyr Ile Asp Lys Gly
1585                1590                1595                1600

Gln Tyr Leu His Ile Pro Arg Ala Gln Val Ser Asp Ser Ala Thr Tyr
                1605                1610                1615

Thr Cys His Val Ala Asn Val Ala Gly Thr Ala Glu Lys Ser Phe His
            1620                1625                1630

Val Asp Val Tyr Val Pro Pro Met Ile Glu Gly Asn Leu Ala Thr Pro
        1635                1640                1645

Leu Asn Lys Gln Val Val Ile Ala His Ser Leu Thr Leu Glu Cys Lys
    1650                1655                1660

Ala Ala Gly Asn Pro Ser Pro Ile Leu Thr Trp Leu Lys Asp Gly Val
```

```
                1665                1670                1675                1680

Pro Val Lys Ala Asn Asp Asn Ile Arg Ile Glu Ala Gly Gly Lys Lys
                1685                1690                1695

Leu Glu Ile Met Ser Ala Gln Glu Ile Asp Arg Gly Gln Tyr Ile Cys
                1700                1705                1710

Val Ala Thr Ser Val Ala Gly Glu Lys Glu Ile Lys Tyr Glu Val Asp
                1715                1720                1725

Val Leu Val Pro Pro Ala Ile Glu Gly Gly Asp Glu Thr Ser Tyr Phe
                1730                1735                1740

Ile Val Met Val Asn Asn Leu Leu Glu Leu Asp Cys His Val Thr Gly
1745                1750                1755                1760

Ser Pro Pro Pro Thr Ile Met Trp Leu Lys Asp Gly Gln Leu Ile Asp
                1765                1770                1775

Glu Arg Asp Gly Phe Lys Ile Leu Leu Asn Gly Arg Lys Leu Val Ile
                1780                1785                1790

Ala Gln Ala Gln Val Ser Asn Thr Gly Leu Tyr Arg Cys Met Ala Ala
                1795                1800                1805

Asn Thr Ala Gly Asp His Lys Lys Glu Phe Glu Val Thr Val His Val
                1810                1815                1820

Pro Pro Thr Ile Lys Ser Ser Gly Leu Ser Glu Arg Val Val Lys
1825                1830                1835                1840

Tyr Lys Pro Val Ala Leu Gln Cys Ile Ala Asn Gly Ile Pro Asn Pro
                1845                1850                1855

Ser Ile Thr Trp Leu Lys Asp Asp Gln Pro Val Asn Thr Ala Gln Gly
                1860                1865                1870

Asn Leu Lys Ile Gln Ser Ser Gly Arg Val Leu Gln Ile Ala Lys Thr
                1875                1880                1885

Leu Leu Glu Asp Ala Gly Arg Tyr Thr Cys Val Ala Thr Asn Ala Ala
                1890                1895                1900

Gly Glu Thr Gln Gln His Ile Gln Leu His Val His Glu Pro Pro Ser
1905                1910                1915                1920

Leu Glu Asp Ala Gly Lys Met Leu Asn Glu Thr Val Leu Val Ser Asn
                1925                1930                1935

Pro Val Gln Leu Glu Cys Lys Ala Ala Gly Asn Pro Val Pro Val Ile
                1940                1945                1950

Thr Trp Tyr Lys Asp Asn Arg Leu Leu Ser Gly Ser Thr Ser Met Thr
                1955                1960                1965

Phe Leu Asn Arg Gly Gln Ile Ile Asp Ile Glu Ser Ala Gln Ile Ser
                1970                1975                1980

Asp Ala Gly Ile Tyr Lys Cys Val Ala Ile Asn Ser Ala Gly Ala Thr
1985                1990                1995                2000

Glu Leu Phe Tyr Ser Leu Gln Val His Val Ala Pro Ser Ile Ser Gly
                2005                2010                2015

Ser Asn Asn Met Val Ala Val Val Asn Asn Pro Val Arg Leu Glu
                2020                2025                2030

Cys Glu Ala Arg Gly Ile Pro Ala Pro Ser Leu Thr Trp Leu Lys Asp
                2035                2040                2045

Gly Ser Pro Val Ser Ser Phe Ser Asn Gly Leu Gln Val Leu Ser Gly
                2050                2055                2060

Gly Arg Ile Leu Ala Leu Thr Ser Ala Gln Ile Ser Asp Thr Gly Arg
2065                2070                2075                2080

Tyr Thr Cys Val Ala Val Asn Ala Ala Gly Glu Lys Gln Arg Asp Ile
                2085                2090                2095
```

```
Asp Leu Arg Val Tyr Val Pro Pro Asn Ile Met Gly Glu Glu Gln Asn
            2100                2105                2110

Val Ser Val Leu Ile Ser Gln Ala Val Glu Leu Leu Cys Gln Ser Asp
        2115                2120                2125

Ala Ile Pro Pro Pro Thr Leu Thr Trp Leu Lys Asp Gly His Pro Leu
    2130                2135                2140

Leu Lys Lys Pro Gly Leu Ser Ile Ser Glu Asn Arg Ser Val Leu Lys
2145                2150                2155                2160

Ile Glu Asp Ala Gln Val Gln Asp Thr Gly Arg Tyr Thr Cys Glu Ala
                2165                2170                2175

Thr Asn Val Ala Gly Lys Thr Glu Lys Asn Tyr Asn Val Asn Ile Trp
            2180                2185                2190

Val Pro Pro Asn Ile Gly Gly Ser Asp Glu Leu Thr Gln Leu Thr Val
        2195                2200                2205

Ile Glu Gly Asn Leu Ile Ser Leu Leu Cys Glu Ser Ser Gly Ile Pro
    2210                2215                2220

Pro Pro Asn Leu Ile Trp Lys Lys Gly Ser Pro Val Leu Thr Asp
2225                2230                2235                2240

Ser Met Gly Arg Val Arg Ile Leu Ser Gly Gly Arg Gln Leu Gln Ile
                2245                2250                2255

Ser Ile Ala Glu Lys Ser Asp Ala Ala Leu Tyr Ser Cys Val Ala Ser
            2260                2265                2270

Asn Val Ala Gly Thr Ala Lys Lys Glu Tyr Asn Leu Gln Val Tyr Ile
        2275                2280                2285

Arg Pro Thr Ile Thr Asn Ser Gly Ser His Pro Thr Glu Ile Ile Val
    2290                2295                2300

Thr Arg Gly Lys Ser Ile Ser Leu Glu Cys Glu Val Gln Gly Ile Pro
2305                2310                2315                2320

Pro Pro Thr Val Thr Trp Met Lys Asp Gly His Pro Leu Ile Lys Ala
                2325                2330                2335

Lys Gly Val Glu Ile Leu Asp Glu Gly His Ile Leu Gln Leu Lys Asn
            2340                2345                2350

Ile His Val Ser Asp Thr Gly Arg Tyr Val Cys Val Ala Val Asn Val
        2355                2360                2365

Ala Gly Met Thr Asp Lys Lys Tyr Asp Leu Ser Val His Ala Pro Pro
    2370                2375                2380

Ser Ile Ile Gly Asn His Arg Ser Pro Glu Asn Ile Ser Val Val Glu
2385                2390                2395                2400

Lys Asn Ser Val Ser Leu Thr Cys Glu Ala Ser Gly Ile Pro Leu Pro
                2405                2410                2415

Ser Ile Thr Trp Phe Lys Asp Gly Trp Pro Val Ser Leu Ser Asn Ser
            2420                2425                2430

Val Arg Ile Leu Ser Gly Gly Arg Met Leu Arg Leu Met Gln Thr Thr
        2435                2440                2445

Met Glu Asp Ala Gly Gln Tyr Thr Cys Val Val Arg Asn Ala Ala Gly
    2450                2455                2460

Glu Glu Arg Lys Ile Phe Gly Leu Ser Val Leu Val Pro Pro His Ile
2465                2470                2475                2480

Val Gly Glu Asn Thr Leu Glu Asp Val Lys Val Lys Glu Lys Gln Ser
                2485                2490                2495

Val Thr Leu Thr Cys Glu Val Thr Gly Asn Pro Val Pro Glu Ile Thr
            2500                2505                2510
```

-continued

```
Trp His Lys Asp Gly Gln Pro Leu Gln Glu Asp Glu Ala His His Ile
        2515                2520                2525
Ile Ser Gly Gly Arg Phe Leu Gln Ile Thr Asn Val Gln Val Pro His
        2530                2535                2540
Thr Gly Arg Tyr Thr Cys Leu Ala Ser Ser Pro Ala Gly His Lys Ser
2545                2550                2555                2560
Arg Ser Phe Ser Leu Asn Val Phe Val Ser Pro Thr Ile Ala Gly Val
            2565                2570                2575
Gly Ser Asp Gly Asn Pro Glu Asp Val Thr Val Ile Leu Asn Ser Pro
            2580                2585                2590
Thr Ser Leu Val Cys Glu Ala Tyr Ser Tyr Pro Pro Ala Thr Ile Thr
        2595                2600                2605
Trp Phe Lys Asp Gly Thr Pro Leu Glu Ser Asn Arg Asn Ile Arg Ile
        2610                2615                2620
Leu Pro Gly Gly Arg Thr Leu Gln Ile Leu Asn Ala Gln Glu Asp Asn
2625                2630                2635                2640
Ala Gly Arg Tyr Ser Cys Val Ala Thr Asn Glu Ala Gly Glu Met Ile
            2645                2650                2655
Lys His Tyr Glu Val Lys Val Tyr Ile Pro Pro Ile Ile Asn Lys Gly
            2660                2665                2670
Asp Leu Trp Gly Pro Gly Leu Ser Pro Lys Glu Val Lys Ile Lys Val
        2675                2680                2685
Asn Asn Thr Leu Thr Leu Glu Cys Glu Ala Tyr Ala Ile Pro Ser Ala
        2690                2695                2700
Ser Leu Ser Trp Tyr Lys Asp Gly Gln Pro Leu Lys Ser Asp Asp His
2705                2710                2715                2720
Val Asn Ile Ala Ala Asn Gly His Thr Leu Gln Ile Lys Glu Ala Gln
            2725                2730                2735
Ile Ser Asp Thr Gly Arg Tyr Thr Cys Val Ala Ser Asn Ile Ala Gly
            2740                2745                2750
Glu Asp Glu Leu Asp Phe Asp Val Asn Ile Gln Val Pro Pro Ser Phe
        2755                2760                2765
Gln Lys Leu Trp Glu Ile Gly Asn Met Leu Asp Thr Gly Arg Asn Gly
        2770                2775                2780
Glu Ala Lys Asp Val Ile Ile Asn Asn Pro Ile Ser Leu Tyr Cys Glu
2785                2790                2795                2800
Thr Asn Ala Ala Pro Pro Pro Thr Leu Thr Trp Tyr Lys Asp Gly His
            2805                2810                2815
Pro Leu Thr Ser Ser Asp Lys Val Leu Ile Leu Pro Gly Gly Arg Val
            2820                2825                2830
Leu Gln Ile Pro Arg Ala Lys Val Glu Asp Ala Gly Arg Tyr Thr Cys
        2835                2840                2845
Val Ala Val Asn Glu Ala Gly Glu Asp Ser Leu Gln Tyr Asp Val Arg
        2850                2855                2860
Val Leu Val Pro Pro Ile Ile Lys Gly Ala Asn Ser Asp Leu Pro Glu
2865                2870                2875                2880
Glu Val Thr Val Leu Val Asn Lys Ser Ala Leu Ile Glu Cys Leu Ser
            2885                2890                2895
Ser Gly Ser Pro Ala Pro Arg Asn Ser Trp Gln Lys Asp Gly Gln Pro
            2900                2905                2910
Leu Leu Glu Asp Asp His His Lys Phe Leu Ser Asn Gly Arg Ile Leu
        2915                2920                2925
Gln Ile Leu Asn Thr Gln Ile Thr Asp Ile Gly Arg Tyr Val Cys Val
```

-continued

```
                2930                2935                2940
Ala Glu Asn Thr Ala Gly Ser Ala Lys Lys Tyr Phe Asn Leu Asn Val
2945                2950                2955                2960

His Val Pro Pro Ser Val Ile Gly Pro Lys Ser Glu Asn Leu Thr Val
                2965                2970                2975

Val Val Asn Asn Phe Ile Ser Leu Thr Cys Glu Val Ser Gly Phe Pro
                2980                2985                2990

Pro Pro Asp Leu Ser Trp Leu Lys Asn Glu Gln Pro Ile Lys Leu Asn
                2995                3000                3005

Thr Asn Thr Leu Ile Val Pro Gly Gly Arg Thr Leu Gln Ile Ile Arg
                3010                3015                3020

Ala Lys Val Ser Asp Gly Gly Glu Tyr Thr Cys Ile Ala Ile Asn Gln
3025                3030                3035                3040

Ala Gly Glu Ser Lys Lys Lys Phe Ser Leu Thr Val Tyr Val Pro Pro
                3045                3050                3055

Ser Ile Lys Asp His Asp Ser Glu Ser Leu Ser Val Val Asn Val Arg
                3060                3065                3070

Glu Gly Thr Ser Val Ser Leu Glu Cys Glu Ser Asn Ala Val Pro Pro
                3075                3080                3085

Pro Val Ile Thr Trp Tyr Lys Asn Gly Arg Met Ile Thr Glu Ser Thr
                3090                3095                3100

His Val Glu Ile Leu Ala Asp Gly Gln Met Leu His Ile Lys Lys Ala
3105                3110                3115                3120

Glu Val Ser Asp Thr Gly Gln Tyr Val Cys Arg Ala Ile Asn Val Ala
                3125                3130                3135

Gly Arg Asp Asp Lys Asn Phe His Leu Asn Val Tyr Val Pro Pro Ser
                3140                3145                3150

Ile Glu Gly Pro Glu Arg Glu Val Ile Val Glu Thr Ile Ser Asn Pro
                3155                3160                3165

Val Thr Leu Thr Cys Asp Ala Thr Gly Ile Pro Pro Pro Thr Ile Ala
                3170                3175                3180

Trp Leu Lys Asn His Lys Arg Ile Glu Asn Ser Asp Ser Leu Glu Val
3185                3190                3195                3200

Arg Ile Leu Ser Gly Gly Ser Lys Leu Gln Ile Ala Arg Ser Gln His
                3205                3210                3215

Ser Asp Ser Gly Asn Tyr Thr Cys Ile Ala Ser Asn Met Glu Gly Lys
                3220                3225                3230

Ala Gln Lys Tyr Tyr Phe Leu Ser Ile Gln Val Pro Pro Ser Val Ala
                3235                3240                3245

Gly Ala Glu Ile Pro Ser Asp Val Ser Val Leu Leu Gly Glu Asn Val
                3250                3255                3260

Glu Leu Val Cys Asn Ala Asn Gly Ile Pro Thr Pro Leu Ile Gln Trp
3265                3270                3275                3280

Leu Lys Asp Gly Lys Pro Ile Ala Ser Gly Glu Thr Glu Arg Ile Arg
                3285                3290                3295

Val Ser Ala Asn Gly Ser Thr Leu Asn Ile Tyr Gly Ala Leu Thr Ser
                3300                3305                3310

Asp Thr Gly Lys Tyr Thr Cys Val Ala Thr Asn Pro Ala Gly Glu Glu
                3315                3320                3325

Asp Arg Ile Phe Asn Leu Asn Val Tyr Val Thr Pro Thr Ile Arg Gly
                3330                3335                3340

Asn Lys Asp Glu Ala Glu Lys Leu Met Thr Leu Val Asp Thr Ser Ile
3345                3350                3355                3360
```

-continued

```
Asn Ile Glu Cys Arg Ala Thr Gly Thr Pro Pro Gln Ile Asn Trp
            3365                3370                3375

Leu Lys Asn Gly Leu Pro Leu Pro Leu Ser Ser His Ile Arg Leu Leu
            3380                3385                3390

Ala Ala Gly Gln Val Ile Arg Ile Val Arg Ala Gln Val Ser Asp Val
            3395                3400                3405

Ala Val Tyr Thr Cys Val Ala Ser Asn Arg Ala Gly Val Asp Asn Lys
            3410                3415                3420

His Tyr Asn Leu Gln Val Phe Ala Pro Pro Asn Met Asp Asn Ser Met
3425                3430                3435                3440

Gly Thr Glu Glu Ile Thr Val Leu Lys Gly Ser Ser Thr Ser Met Ala
            3445                3450                3455

Cys Ile Thr Asp Gly Thr Pro Ala Pro Ser Met Ala Trp Leu Arg Asp
            3460                3465                3470

Gly Gln Pro Leu Gly Leu Asp Ala His Leu Thr Val Ser Thr His Gly
            3475                3480                3485

Met Val Leu Gln Leu Leu Lys Ala Glu Thr Glu Asp Ser Gly Lys Tyr
            3490                3495                3500

Thr Cys Ile Ala Ser Asn Glu Ala Gly Glu Val Ser Lys His Phe Ile
3505                3510                3515                3520

Leu Lys Val Leu Glu Pro Pro His Ile Asn Gly Ser Glu Glu His Glu
            3525                3530                3535

Glu Ile Ser Val Ile Val Asn Asn Pro Leu Glu Leu Thr Cys Ile Ala
            3540                3545                3550

Ser Gly Ile Pro Ala Pro Lys Met Thr Trp Met Lys Asp Gly Arg Pro
            3555                3560                3565

Leu Pro Gln Thr Asp Gln Val Gln Thr Leu Gly Gly Gly Glu Val Leu
            3570                3575                3580

Arg Ile Ser Thr Ala Gln Val Glu Asp Thr Gly Arg Tyr Thr Cys Leu
3585                3590                3595                3600

Ala Ser Ser Pro Ala Gly Asp Asp Lys Glu Tyr Leu Val Arg Val
            3605                3610                3615

His Val Pro Pro Asn Ile Ala Gly Thr Asp Glu Pro Arg Asp Ile Thr
            3620                3625                3630

Val Leu Arg Asn Arg Gln Val Thr Leu Glu Cys Lys Ser Asp Ala Val
            3635                3640                3645

Pro Pro Pro Val Ile Thr Trp Leu Arg Asn Gly Glu Arg Leu Gln Ala
            3650                3655                3660

Thr Pro Arg Val Arg Ile Leu Ser Gly Gly Arg Tyr Leu Gln Ile Asn
3665                3670                3675                3680

Asn Ala Asp Leu Gly Asp Thr Ala Asn Tyr Thr Cys Val Ala Ser Asn
            3685                3690                3695

Ile Ala Gly Lys Thr Thr Arg Glu Phe Ile Leu Thr Val Asn Val Pro
            3700                3705                3710

Pro Asn Ile Lys Gly Gly Pro Gln Ser Leu Val Ile Leu Leu Asn Lys
            3715                3720                3725

Ser Thr Val Leu Glu Cys Ile Ala Glu Gly Val Pro Thr Pro Arg Ile
            3730                3735                3740

Thr Trp Arg Lys Asp Gly Ala Val Leu Ala Gly Asn His Ala Arg Tyr
3745                3750                3755                3760

Ser Ile Leu Glu Asn Gly Phe Leu His Ile Gln Ser Ala His Val Thr
            3765                3770                3775
```

-continued

```
Asp Thr Gly Arg Tyr Leu Cys Met Ala Thr Asn Ala Ala Gly Thr Asp
            3780                3785                3790

Arg Arg Arg Ile Asp Leu Gln Val His Val Pro Pro Ser Ile Ala Pro
        3795                3800                3805

Gly Pro Thr Asn Met Thr Val Ile Val Asn Val Gln Thr Leu Ala
    3810                3815                3820

Cys Glu Ala Thr Gly Ile Pro Lys Pro Ser Ile Asn Trp Arg Lys Asn
3825            3830                3835                3840

Gly His Leu Leu Asn Val Asp Gln Asn Gln Asn Ser Tyr Arg Leu Leu
            3845                3850                3855

Ser Ser Gly Ser Leu Val Ile Ile Ser Pro Ser Val Asp Asp Thr Ala
        3860                3865                3870

Thr Tyr Glu Cys Thr Val Thr Asn Gly Ala Gly Asp Asp Lys Arg Thr
    3875                3880                3885

Val Asp Leu Thr Val Gln Val Pro Pro Ser Ile Ala Asp Glu Pro Thr
3890                3895                3900

Asp Phe Leu Val Thr Lys His Ala Pro Ala Val Ile Thr Cys Thr Ala
3905            3910                3915                3920

Ser Gly Val Pro Phe Pro Ser Ile His Trp Thr Lys Asn Gly Ile Arg
            3925                3930                3935

Leu Leu Pro Arg Gly Asp Gly Tyr Arg Ile Leu Ser Ser Gly Ala Ile
        3940                3945                3950

Glu Ile Leu Ala Thr Gln Leu Asn His Ala Gly Arg Tyr Thr Cys Val
    3955                3960                3965

Ala Arg Asn Ala Ala Gly Ser Ala His Arg His Val Thr Leu His Val
    3970                3975                3980

His Glu Pro Pro Val Ile Gln Pro Gln Pro Ser Glu Leu His Val Ile
3985            3990                3995                4000

Leu Asn Asn Pro Ile Leu Leu Pro Cys Glu Ala Thr Gly Thr Pro Ser
            4005                4010                4015

Pro Phe Ile Thr Trp Gln Lys Glu Gly Ile Asn Val Asn Thr Ser Gly
        4020                4025                4030

Arg Asn His Ala Val Leu Pro Ser Gly Gly Leu Gln Ile Ser Arg Ala
    4035                4040                4045

Val Arg Glu Asp Ala Gly Thr Tyr Met Cys Val Ala Gln Asn Pro Ala
    4050                4055                4060

Gly Thr Ala Leu Gly Lys Ile Lys Leu Asn Val Gln Val Pro Pro Val
4065            4070                4075                4080

Ile Ser Pro His Leu Lys Glu Tyr Val Ile Ala Val Asp Lys Pro Ile
            4085                4090                4095

Thr Leu Ser Cys Glu Ala Asp Gly Leu Pro Pro Pro Asp Ile Thr Trp
        4100                4105                4110

His Lys Asp Gly Arg Ala Ile Val Glu Ser Ile Arg Gln Arg Val Leu
    4115                4120                4125

Ser Ser Gly Ser Leu Gln Ile Ala Phe Val Gln Pro Gly Asp Ala Gly
    4130                4135                4140

His Tyr Thr Cys Met Ala Ala Asn Val Ala Gly Ser Ser Ser Thr Ser
4145            4150                4155                4160

Thr Lys Leu Thr Val His Val Pro Pro Arg Ile Arg Ser Thr Glu Gly
            4165                4170                4175

His Tyr Thr Val Asn Glu Asn Ser Gln Ala Ile Leu Pro Cys Val Ala
        4180                4185                4190

Asp Gly Ile Pro Thr Pro Ala Ile Asn Trp Lys Lys Asp Asn Val Leu
```

-continued

```
            4195                4200                4205
Leu Ala Asn Leu Leu Gly Lys Tyr Thr Ala Glu Pro Tyr Gly Glu Leu
        4210                4215                4220
Ile Leu Glu Asn Val Val Leu Glu Asp Ser Gly Phe Tyr Thr Cys Val
4225                4230                4235                4240
Ala Asn Asn Ala Ala Gly Glu Asp Thr His Thr Val Ser Leu Thr Val
            4245                4250                4255
His Val Leu Pro Thr Phe Thr Glu Leu Pro Gly Asp Val Ser Leu Asn
        4260                4265                4270
Lys Gly Glu Gln Leu Arg Leu Ser Cys Lys Ala Thr Gly Ile Pro Leu
        4275                4280                4285
Pro Lys Leu Thr Trp Thr Phe Asn Asn Asn Ile Ile Pro Ala His Phe
        4290                4295                4300
Asp Ser Val Asn Gly His Ser Glu Leu Val Ile Glu Arg Val Ser Lys
4305                4310                4315                4320
Glu Asp Ser Gly Thr Tyr Val Cys Thr Ala Glu Asn Ser Val Gly Phe
            4325                4330                4335
Val Lys Ala Ile Gly Phe Val Tyr Val Lys Glu Pro Pro Val Phe Lys
        4340                4345                4350
Gly Asp Tyr Pro Ser Asn Trp Ile Glu Pro Leu Gly Gly Asn Ala Ile
        4355                4360                4365
Leu Asn Cys Glu Val Lys Gly Asp Pro Thr Pro Thr Ile Gln Trp Asn
    4370                4375                4380
Arg Lys Gly Val Asp Ile Glu Ile Ser His Arg Ile Arg Gln Leu Gly
4385                4390                4395                4400
Asn Gly Ser Leu Ala Ile Tyr Gly Thr Val Asn Glu Asp Ala Gly Asp
            4405                4410                4415
Tyr Thr Cys Val Ala Thr Asn Glu Ala Gly Val Val Glu Arg Ser Met
            4420                4425                4430
Ser Leu Thr Leu Gln Ser Pro Pro Ile Ile Thr Leu Glu Pro Val Glu
        4435                4440                4445
Thr Val Ile Asn Ala Gly Gly Lys Ile Ile Leu Asn Cys Gln Ala Thr
        4450                4455                4460
Gly Glu Pro Gln Pro Thr Ile Thr Trp Ser Arg Gln Gly His Ser Ile
4465                4470                4475                4480
Ser Trp Asp Asp Arg Val Asn Val Leu Ser Asn Asn Ser Leu Tyr Ile
                4485                4490                4495
Ala Asp Ala Gln Lys Glu Asp Thr Ser Glu Phe Glu Cys Val Ala Arg
            4500                4505                4510
Asn Leu Met Gly Ser Val Leu Val Arg Val Pro Val Ile Val Gln Val
        4515                4520                4525
His Gly Gly Phe Ser Gln Trp Ser Ala Trp Arg Ala Cys Ser Val Thr
        4530                4535                4540
Cys Gly Lys Gly Ile Gln Lys Arg Ser Arg Leu Cys Asn Gln Pro Leu
4545                4550                4555                4560
Pro Ala Asn Gly Gly Lys Pro Cys Gln Gly Ser Asp Leu Glu Met Arg
            4565                4570                4575
Asn Cys Gln Asn Lys Pro Cys Pro Val Asp Gly Ser Trp Ser Glu Trp
            4580                4585                4590
Ser Leu Trp Glu Glu Cys Thr Arg Ser Cys Gly Arg Gly Asn Gln Thr
        4595                4600                4605
Arg Thr Arg Thr Cys Asn Asn Pro Ser Val Gln His Gly Gly Arg Pro
        4610                4615                4620
```

-continued

```
Cys Glu Gly Asn Ala Val Glu Ile Ile Met Cys Asn Ile Arg Pro Cys
4625                4630                4635                4640

Pro Val His Gly Ala Trp Ser Ala Trp Gln Pro Trp Gly Thr Cys Ser
            4645                4650                4655

Glu Ser Cys Gly Lys Gly Thr Gln Thr Arg Ala Arg Leu Cys Asn Asn
            4660                4665                4670

Pro Pro Pro Ala Phe Gly Gly Ser Tyr Cys Asp Gly Ala Glu Thr Gln
            4675                4680                4685

Met Gln Val Cys Asn Glu Arg Asn Cys Pro Ile His Gly Lys Trp Ala
            4690                4695                4700

Thr Trp Ala Ser Trp Ser Ala Cys Ser Val Ser Cys Gly Gly Gly Ala
4705                4710                4715                4720

Arg Gln Arg Thr Arg Gly Cys Ser Asp Pro Val Pro Gln Tyr Gly Gly
            4725                4730                4735

Arg Lys Cys Glu Gly Ser Asp Val Gln Ser Asp Phe Cys Asn Ser Asp
            4740                4745                4750

Pro Cys Pro Thr His Gly Asn Trp Ser Pro Trp Ser Gly Trp Gly Thr
            4755                4760                4765

Cys Ser Arg Thr Cys Asn Gly Gly Gln Met Arg Arg Tyr Arg Thr Cys
4770                4775                4780

Asp Asn Pro Pro Pro Ser Asn Gly Gly Arg Ala Cys Gly Gly Pro Asp
4785                4790                4795                4800

Ser Gln Ile Gln Arg Cys Asn Thr Asp Met Cys Pro Val Asp Gly Ser
            4805                4810                4815

Trp Gly Ser Trp His Ser Trp Ser Gln Cys Ser Ala Ser Cys Gly Gly
            4820                4825                4830

Gly Glu Lys Thr Arg Lys Arg Leu Cys Asp His Pro Val Pro Val Lys
            4835                4840                4845

Gly Gly Arg Pro Cys Pro Gly Asp Thr Thr Gln Val Thr Arg Cys Asn
4850                4855                4860

Val Gln Ala Cys Pro Gly Gly Pro Gln Arg Ala Arg Gly Ser Val Ile
4865                4870                4875                4880

Gly Asn Ile Asn Asp Val Glu Phe Gly Ile Ala Phe Leu Asn Ala Thr
            4885                4890                4895

Ile Thr Asp Ser Pro Asn Ser Asp Thr Arg Ile Ile Arg Ala Lys Ile
            4900                4905                4910

Thr Asn Val Pro Arg Ser Leu Gly Ser Ala Met Arg Lys Ile Val Ser
            4915                4920                4925

Ile Leu Asn Pro Ile Tyr Trp Thr Thr Ala Lys Glu Ile Gly Glu Ala
            4930                4935                4940

Val Asn Gly Phe Thr Leu Thr Asn Ala Val Phe Lys Arg Glu Thr Gln
4945                4950                4955                4960

Val Glu Phe Ala Thr Gly Glu Ile Leu Gln Met Ser His Ile Ala Arg
            4965                4970                4975

Gly Leu Asp Ser Asp Gly Ser Leu Leu Leu Asp Ile Val Val Ser Gly
            4980                4985                4990

Tyr Val Leu Gln Leu Gln Ser Pro Ala Glu Val Thr Val Lys Asp Tyr
            4995                5000                5005

Thr Glu Asp Tyr Ile Gln Thr Gly Pro Gly Gln Leu Tyr Ala Tyr Ser
            5010                5015                5020

Thr Arg Leu Phe Thr Ile Asp Gly Ile Ser Ile Pro Tyr Thr Trp Asn
5025                5030                5035                5040
```

-continued

His Thr Val Phe Tyr Asp Gln Ala Gln Gly Arg Met Pro Phe Leu Val
            5045                5050                5055

Glu Thr Leu His Ala Ser Ser Val Glu Ser Asp Tyr Asn Gln Ile Glu
            5060                5065                5070

Glu Thr Leu Gly Phe Lys Ile His Ala Ser Ile Ser Lys Gly Asp Arg
            5075                5080                5085

Ser Asn Gln Cys Pro Ser Gly Phe Thr Leu Asp Ser Val Gly Pro Phe
            5090                5095                5100

Cys Ala Asp Glu Asp Glu Cys Ala Ala Gly Asn Pro Cys Ser His Ser
5105                5110                5115                5120

Cys His Asn Ala Met Gly Thr Tyr Tyr Cys Ser Cys Pro Lys Gly Leu
            5125                5130                5135

Thr Ile Ala Ala Asp Gly Arg Thr Cys Gln Asp Ile Asp Glu Cys Ala
            5140                5145                5150

Leu Gly Arg His Thr Cys His Ala Gly Gln Asp Cys Asp Asn Thr Ile
            5155                5160                5165

Gly Ser Tyr Arg Cys Val Val Arg Cys Gly Ser Gly Phe Arg Arg Thr
            5170                5175                5180

Ser Asp Gly Leu Ser Cys Gln Asp Ile Asn Glu Cys Gln Glu Ser Ser
5185                5190                5195                5200

Pro Cys His Gln Arg Cys Phe Asn Ala Ile Gly Ser Phe His Cys Gly
            5205                5210                5215

Cys Glu Pro Gly Tyr Gln Leu Lys Gly Arg Lys Cys Met Asp Val Asn
            5220                5225                5230

Glu Cys Arg Gln Asn Val Cys Arg Pro Asp Gln His Cys Lys Asn Thr
            5235                5240                5245

Arg Gly Gly Tyr Lys Cys Ile Asp Leu Cys Pro Asn Gly Met Thr Lys
            5250                5255                5260

Ala Glu Asn Gly Thr Cys Ile Asp Ile Asp Glu Cys Lys Asp Gly Thr
5265                5270                5275                5280

His Gln Cys Arg Tyr Asn Gln Ile Cys Glu Asn Thr Arg Gly Ser Tyr
            5285                5290                5295

Arg Cys Val Cys Pro Arg Gly Tyr Arg Ser Gln Gly Val Gly Arg Pro
            5300                5305                5310

Cys Met Asp Ile Asn Glu Cys Glu Gln Val Pro Lys Pro Cys Ala His
            5315                5320                5325

Gln Cys Ser Asn Thr Pro Gly Ser Phe Lys Cys Ile Cys Pro Pro Gly
            5330                5335                5340

Gln His Leu Leu Gly Asp Gly Lys Ser Cys Ala Gly Leu Glu Arg Leu
5345                5350                5355                5360

Pro Asn Tyr Gly Thr Gln Tyr Ser Ser Tyr Asn Leu Ala Arg Phe Ser
            5365                5370                5375

Pro Val Arg Asn Asn Tyr Gln Pro Gln His Tyr Arg Gln Tyr Ser
            5380                5385                5390

His Leu Tyr Ser Ser Tyr Ser Glu Tyr Arg Asn Ser Arg Thr Ser Leu
            5395                5400                5405

Ser Arg Thr Arg Arg Thr Ile Arg Lys Thr Cys Pro Glu Gly Ser Glu
            5410                5415                5420

Ala Ser His Asp Thr Cys Val Asp Ile Asp Glu Cys Glu Asn Thr Asp
5425                5430                5435                5440

Ala Cys Gln His Glu Cys Lys Asn Thr Phe Gly Ser Tyr Gln Cys Ile
            5445                5450                5455

Cys Pro Pro Gly Tyr Gln Leu Thr His Asn Gly Lys Thr Cys Gln Asp

-continued

```
                   5460                5465                5470
Ile Asp Glu Cys Leu Glu Gln Asn Val His Cys Gly Pro Asn Arg Met
        5475                5480                5485
Cys Phe Asn Met Arg Gly Ser Tyr Gln Cys Ile Asp Thr Pro Cys Pro
        5490                5495                5500
Pro Asn Tyr Gln Arg Asp Pro Val Ser Gly Phe Cys Leu Lys Asn Cys
5505                5510                5515                5520
Pro Pro Asn Asp Leu Glu Cys Ala Leu Ser Pro Tyr Ala Leu Glu Tyr
                5525                5530                5535
Lys Leu Val Ser Leu Pro Phe Gly Ile Ala Thr Asn Gln Asp Leu Ile
        5540                5545                5550
Arg Leu Val Ala Tyr Thr Gln Asp Gly Val Met His Pro Arg Thr Thr
        5555                5560                5565
Phe Leu Met Val Asp Glu Glu Gln Thr Val Pro Phe Ala Leu Arg Asp
        5570                5575                5580
Glu Asn Leu Lys Gly Val Val Tyr Thr Thr Arg Pro Leu Arg Glu Ala
5585                5590                5595                5600
Glu Thr Tyr Arg Met Arg Val Arg Ala Ser Ser Tyr Ser Ala Asn Gly
                5605                5610                5615
Thr Ile Glu Tyr Gln Thr Thr Phe Ile Val Tyr Ile Ala Val Ser Ala
                5620                5625                5630
Tyr Pro Tyr
        5635

<210> SEQ ID NO 3
<211> LENGTH: 22
<212> TYPE: DNA
<213> ORGANISM: Artificial Sequence
<220> FEATURE:
<223> OTHER INFORMATION: FIBL-6 exon 104-specific forward primer used
      for DHPLC assay

<400> SEQUENCE: 3
ccgtgcaagg ttatagctac tg                                            22

<210> SEQ ID NO 4
<211> LENGTH: 20
<212> TYPE: DNA
<213> ORGANISM: Artificial Sequence
<220> FEATURE:
<223> OTHER INFORMATION: FIBL-6 exon 104-specific reverse primer used
      for DHPLC assay

<400> SEQUENCE: 4
atggcatacg agcagacatt                                               20

<210> SEQ ID NO 5
<211> LENGTH: 21
<212> TYPE: DNA
<213> ORGANISM: Artificial Sequence
<220> FEATURE:
<223> OTHER INFORMATION: FIBL-6 exon 104-specific forward primer used
      for ASO assay

<400> SEQUENCE: 5
tatcatggca tacgagcaga c                                             21

<210> SEQ ID NO 6
<211> LENGTH: 22
<212> TYPE: DNA
<213> ORGANISM: Artificial Sequence
```

```
<220> FEATURE:
<223> OTHER INFORMATION: FIBL-6 exon 104-specific reverse primer used
      for ASO assay

<400> SEQUENCE: 6
ttcactgcac tcaaacaatc ac                                              22

<210> SEQ ID NO 7
<211> LENGTH: 17
<212> TYPE: DNA
<213> ORGANISM: Artificial Sequence
<220> FEATURE:
<223> OTHER INFORMATION: Oligonucleotide probe specific for wildtype A
      allele at nucleotide position 16,263 of FIBL-6
      cDNA sequence (SEQ ID NO:1)

<400> SEQUENCE: 7
accaggacaa catttat                                                    17

<210> SEQ ID NO 8
<211> LENGTH: 17
<212> TYPE: DNA
<213> ORGANISM: Artificial Sequence
<220> FEATURE:
<223> OTHER INFORMATION: Oligonucleotide probe specific for mutant G
      variant at nucleotide position 16,263 of FIBL-6
      cDNA sequence (SEQ ID NO:1)

<400> SEQUENCE: 8
accaggacga catttat                                                    17

<210> SEQ ID NO 9
<211> LENGTH: 21
<212> TYPE: DNA
<213> ORGANISM: Artificial Sequence
<220> FEATURE:
<223> OTHER INFORMATION: FIBL-6 exon 103-specific common upstream
      forward primer used to differentiate alternative splicing
      involving exon 104

<400> SEQUENCE: 9
caagaagcag ctatcgttgt g                                               21

<210> SEQ ID NO 10
<211> LENGTH: 23
<212> TYPE: DNA
<213> ORGANISM: Artificial Sequence
<220> FEATURE:
<223> OTHER INFORMATION: FIBL-6 exon 104-specific common upstream
      reverse primer used to differentiate alternative splicing
      involving exon 104

<400> SEQUENCE: 10
actgtctgta atgctgttga ggt                                             23

<210> SEQ ID NO 11
<211> LENGTH: 21
<212> TYPE: DNA
<213> ORGANISM: Artificial Sequence
<220> FEATURE:
<223> OTHER INFORMATION: FIBL-6 exon 105-specific common upstream
      reverse primer used to differentiate alternative splicing
      involving exon 104

<400> SEQUENCE: 11
gcatgtcttt ccattgtgtg t                                               21
```

```
<210> SEQ ID NO 12
<211> LENGTH: 15
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 12
gacaacattt attag                                                          15

<210> SEQ ID NO 13
<211> LENGTH: 15
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 13
ggacaacatt tatta                                                          15

<210> SEQ ID NO 14
<211> LENGTH: 15
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 14
aggacaacat ttatt                                                          15

<210> SEQ ID NO 15
<211> LENGTH: 15
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 15
caggacaaca tttat                                                          15

<210> SEQ ID NO 16
<211> LENGTH: 15
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 16
ccaggacaac attta                                                          15

<210> SEQ ID NO 17
<211> LENGTH: 15
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 17
accaggacaa cattt                                                          15

<210> SEQ ID NO 18
```

```
<211> LENGTH: 15
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 18
caccaggaca acatt                                                      15

<210> SEQ ID NO 19
<211> LENGTH: 15
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 19
ccaccaggac aacat                                                      15

<210> SEQ ID NO 20
<211> LENGTH: 15
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 20
tccaccagga caaca                                                      15

<210> SEQ ID NO 21
<211> LENGTH: 16
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 21
gacaacattt attagg                                                     16

<210> SEQ ID NO 22
<211> LENGTH: 16
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 22
ggacaacatt tattag                                                     16

<210> SEQ ID NO 23
<211> LENGTH: 16
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 23
aggacaacat ttatta                                                     16

<210> SEQ ID NO 24
<211> LENGTH: 16
```

```
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 24
caggacaaca tttatt                                                       16

<210> SEQ ID NO 25
<211> LENGTH: 16
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 25
ccaggacaac atttat                                                       16

<210> SEQ ID NO 26
<211> LENGTH: 16
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 26
accaggacaa cattta                                                       16

<210> SEQ ID NO 27
<211> LENGTH: 16
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 27
caccaggaca acattt                                                       16

<210> SEQ ID NO 28
<211> LENGTH: 16
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 28
ccaccaggac aacatt                                                       16

<210> SEQ ID NO 29
<211> LENGTH: 16
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 29
tccaccagga caacat                                                       16

<210> SEQ ID NO 30
<211> LENGTH: 16
<212> TYPE: DNA
```

```
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 30
gtccaccagg acaaca                                                         16

<210> SEQ ID NO 31
<211> LENGTH: 17
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 31
gacaacattt attaggg                                                        17

<210> SEQ ID NO 32
<211> LENGTH: 17
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 32
ggacaacatt tattagg                                                        17

<210> SEQ ID NO 33
<211> LENGTH: 17
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 33
aggacaacat ttattag                                                        17

<210> SEQ ID NO 34
<211> LENGTH: 17
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 34
caggacaaca tttatta                                                        17

<210> SEQ ID NO 35
<211> LENGTH: 17
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 35
ccaggacaac atttatt                                                        17

<210> SEQ ID NO 36
<211> LENGTH: 17
<212> TYPE: DNA
<213> ORGANISM: Artificial Sequence
```

```
<220> FEATURE:
<223> OTHER INFORMATION: Exemplary wild-type oligo with an A at position
      16,263 of SEQ ID NO:1

<400> SEQUENCE: 36
caccaggaca acattta                                                          17

<210> SEQ ID NO 37
<211> LENGTH: 17
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 37
ccaccaggac aacattt                                                          17

<210> SEQ ID NO 38
<211> LENGTH: 17
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 38
tccaccagga caacatt                                                          17

<210> SEQ ID NO 39
<211> LENGTH: 17
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 39
gtccaccagg acaacat                                                          17

<210> SEQ ID NO 40
<211> LENGTH: 17
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 40
tgtccaccag gacaaca                                                          17

<210> SEQ ID NO 41
<211> LENGTH: 18
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 41
gacaacattt attagggg                                                         18

<210> SEQ ID NO 42
<211> LENGTH: 18
<212> TYPE: DNA
<213> ORGANISM: Artificial Sequence
<220> FEATURE:
```

<223> OTHER INFORMATION: Exemplary wild-type oligo with an A at position
      16,263 of SEQ ID NO:1

<400> SEQUENCE: 42
ggacaacatt tattaggg                                                   18

<210> SEQ ID NO 43
<211> LENGTH: 18
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 43
aggacaacat ttattagg                                                   18

<210> SEQ ID NO 44
<211> LENGTH: 18
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 44
caggacaaca tttattag                                                   18

<210> SEQ ID NO 45
<211> LENGTH: 18
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 45
ccaggacaac atttatta                                                   18

<210> SEQ ID NO 46
<211> LENGTH: 18
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 46
accaggacaa catttatt                                                   18

<210> SEQ ID NO 47
<211> LENGTH: 18
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 47
caccaggaca acatttat                                                   18

<210> SEQ ID NO 48
<211> LENGTH: 18
<212> TYPE: DNA
<213> ORGANISM: Artificial Sequence
<220> FEATURE:
<223> OTHER INFORMATION: Exemplary wild-type oligo with an A at position 16,263 of SEQ ID NO:1

<400> SEQUENCE: 48
ccaccaggac aacattta                                               18

<210> SEQ ID NO 49
<211> LENGTH: 18
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 49
tccaccagga caacattt                                               18

<210> SEQ ID NO 50
<211> LENGTH: 18
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 50
gtccaccagg acaacatt                                               18

<210> SEQ ID NO 51
<211> LENGTH: 18
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 51
tgtccaccag gacaacat                                               18

<210> SEQ ID NO 52
<211> LENGTH: 18
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 52
ctgtccacca ggacaaca                                               18

<210> SEQ ID NO 53
<211> LENGTH: 19
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 53
gacaacattt attagggga                                              19

<210> SEQ ID NO 54
<211> LENGTH: 19
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

```
<400> SEQUENCE: 54
ggacaacatt tattagggg                                                 19

<210> SEQ ID NO 55
<211> LENGTH: 19
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 55
aggacaacat ttattaggg                                                 19

<210> SEQ ID NO 56
<211> LENGTH: 19
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 56
caggacaaca tttattagg                                                 19

<210> SEQ ID NO 57
<211> LENGTH: 19
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 57
ccaggacaac atttattag                                                 19

<210> SEQ ID NO 58
<211> LENGTH: 19
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 58
accaggacaa catttatta                                                 19

<210> SEQ ID NO 59
<211> LENGTH: 19
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 59
caccaggaca acatttatt                                                 19

<210> SEQ ID NO 60
<211> LENGTH: 19
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1
```

```
<400> SEQUENCE: 60
ccaccaggac aacatttat                                              19

<210> SEQ ID NO 61
<211> LENGTH: 19
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 61
tccaccagga caacattta                                              19

<210> SEQ ID NO 62
<211> LENGTH: 19
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 62
gtccaccagg acaacattt                                              19

<210> SEQ ID NO 63
<211> LENGTH: 19
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 63
tgtccaccag gacaacatt                                              19

<210> SEQ ID NO 64
<211> LENGTH: 19
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 64
ctgtccacca ggacaacat                                              19

<210> SEQ ID NO 65
<211> LENGTH: 19
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 65
tctgtccacc aggacaaca                                              19

<210> SEQ ID NO 66
<211> LENGTH: 20
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 66
```
gacaacattt attaggggac                                               20

<210> SEQ ID NO 67
<211> LENGTH: 20
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 67
ggacaacatt tattaggga                                                20

<210> SEQ ID NO 68
<211> LENGTH: 20
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 68
aggacaacat ttattagggg                                               20

<210> SEQ ID NO 69
<211> LENGTH: 20
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 69
caggacaaca tttattaggg                                               20

<210> SEQ ID NO 70
<211> LENGTH: 20
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 70
ccaggacaac atttattagg                                               20

<210> SEQ ID NO 71
<211> LENGTH: 20
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 71
accaggacaa catttattag                                               20

<210> SEQ ID NO 72
<211> LENGTH: 20
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 72
caccaggaca acatttatta                                          20

<210> SEQ ID NO 73
<211> LENGTH: 20
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 73
ccaccaggac aacatttatt                                          20

<210> SEQ ID NO 74
<211> LENGTH: 20
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 74
tccaccagga caacatttat                                          20

<210> SEQ ID NO 75
<211> LENGTH: 20
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 75
gtccaccagg acaacattta                                          20

<210> SEQ ID NO 76
<211> LENGTH: 20
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 76
tgtccaccag gacaacattt                                          20

<210> SEQ ID NO 77
<211> LENGTH: 20
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 77
ctgtccacca ggacaacatt                                          20

<210> SEQ ID NO 78
<211> LENGTH: 20
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 78
tctgtccacc aggacaacat                                          20

```
<210> SEQ ID NO 79
<211> LENGTH: 20
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 79
atctgtccac caggacaaca                                                    20

<210> SEQ ID NO 80
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 80
gacaacattt attagggac g                                                   21

<210> SEQ ID NO 81
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 81
ggacaacatt tattgggga c                                                   21

<210> SEQ ID NO 82
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 82
aggacaacat ttattagggg a                                                  21

<210> SEQ ID NO 83
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 83
caggacaaca tttattaggg g                                                  21

<210> SEQ ID NO 84
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 84
ccaggacaac atttattagg g                                                  21
```

-continued

```
<210> SEQ ID NO 85
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 85
accaggacaa catttattag g                                              21

<210> SEQ ID NO 86
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 86
caccaggaca acatttatta g                                              21

<210> SEQ ID NO 87
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 87
ccaccaggac aacatttatt a                                              21

<210> SEQ ID NO 88
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 88
tccaccagga caacatttat t                                              21

<210> SEQ ID NO 89
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 89
gtccaccagg acaacattta t                                              21

<210> SEQ ID NO 90
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 90
tgtccaccag gacaacattt a                                              21
```

<210> SEQ ID NO 91
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 91
ctgtccacca ggacaacatt t                                              21

<210> SEQ ID NO 92
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 92
tctgtccacc aggacaacat t                                              21

<210> SEQ ID NO 93
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 93
atctgtccac caggacaaca t                                              21

<210> SEQ ID NO 94
<211> LENGTH: 21
<212> TYPE: DNA
<213> ORGANISM: Artificial Sequence
<220> FEATURE:
<223> OTHER INFORMATION: Exemplary wild-type oligo with an A at position
      16,263 of SEQ ID NO:1

<400> SEQUENCE: 94
tatctgtcca ccaggacaac a                                              21

<210> SEQ ID NO 95
<211> LENGTH: 15
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 95
gacgacattt attag                                                     15

<210> SEQ ID NO 96
<211> LENGTH: 15
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 96
ggacgacatt tatta                                                     15

<210> SEQ ID NO 97

<211> LENGTH: 15
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 97
aggacgacat ttatt                                                         15

<210> SEQ ID NO 98
<211> LENGTH: 15
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 98
caggacgaca tttat                                                         15

<210> SEQ ID NO 99
<211> LENGTH: 15
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 99
ccaggacgac attta                                                         15

<210> SEQ ID NO 100
<211> LENGTH: 15
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 100
accaggacga cattt                                                         15

<210> SEQ ID NO 101
<211> LENGTH: 15
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 101
caccaggacg acatt                                                         15

<210> SEQ ID NO 102
<211> LENGTH: 15
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 102
ccaccaggac gacat                                                         15

<210> SEQ ID NO 103
<211> LENGTH: 15

```
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 103
tccaccagga cgaca                                                     15

<210> SEQ ID NO 104
<211> LENGTH: 16
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 104
gacgacattt attagg                                                    16

<210> SEQ ID NO 105
<211> LENGTH: 16
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 105
ggacgacatt tattag                                                    16

<210> SEQ ID NO 106
<211> LENGTH: 16
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 106
aggacgacat ttatta                                                    16

<210> SEQ ID NO 107
<211> LENGTH: 16
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 107
caggacgaca tttatt                                                    16

<210> SEQ ID NO 108
<211> LENGTH: 16
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 108
ccaggacgac atttat                                                    16

<210> SEQ ID NO 109
<211> LENGTH: 16
<212> TYPE: DNA
```

-continued

```
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 109
accaggacga cattta                                                    16

<210> SEQ ID NO 110
<211> LENGTH: 16
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 110
caccaggacg acattt                                                    16

<210> SEQ ID NO 111
<211> LENGTH: 16
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 111
ccaccaggac gacatt                                                    16

<210> SEQ ID NO 112
<211> LENGTH: 16
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 112
tccaccagga cgacat                                                    16

<210> SEQ ID NO 113
<211> LENGTH: 16
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 113
gtccaccagg acgaca                                                    16

<210> SEQ ID NO 114
<211> LENGTH: 17
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 114
gacgacattt attaggg                                                   17

<210> SEQ ID NO 115
<211> LENGTH: 17
<212> TYPE: DNA
<213> ORGANISM: Artificial Sequence
```

```
<220> FEATURE:
<223> OTHER INFORMATION: Oligo for detecting mutation with a G at
      position 16,263 of SEQ ID NO:1

<400> SEQUENCE: 115
ggacgacatt tattagg                                                17

<210> SEQ ID NO 116
<211> LENGTH: 17
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 116
aggacgacat ttattag                                                17

<210> SEQ ID NO 117
<211> LENGTH: 17
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 117
caggacgaca tttatta                                                17

<210> SEQ ID NO 118
<211> LENGTH: 17
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 118
ccaggacgac atttatt                                                17

<210> SEQ ID NO 119
<211> LENGTH: 17
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 119
caccaggacg acattta                                                17

<210> SEQ ID NO 120
<211> LENGTH: 17
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 120
ccaccaggac gacattt                                                17

<210> SEQ ID NO 121
<211> LENGTH: 17
<212> TYPE: DNA
<213> ORGANISM: Artificial Sequence
<220> FEATURE:
```

<223> OTHER INFORMATION: Oligo for detecting mutation with a G at
      position 16,263 of SEQ ID NO:1

<400> SEQUENCE: 121
tccaccagga cgacatt                                                  17

<210> SEQ ID NO 122
<211> LENGTH: 17
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 122
gtccaccagg acgacat                                                  17

<210> SEQ ID NO 123
<211> LENGTH: 17
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 123
tgtccaccag gacgaca                                                  17

<210> SEQ ID NO 124
<211> LENGTH: 18
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 124
gacgacattt attagggg                                                 18

<210> SEQ ID NO 125
<211> LENGTH: 18
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 125
ggacgacatt tattaggg                                                 18

<210> SEQ ID NO 126
<211> LENGTH: 18
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 126
aggacgacat ttattagg                                                 18

<210> SEQ ID NO 127
<211> LENGTH: 18
<212> TYPE: DNA
<213> ORGANISM: Artificial Sequence
<220> FEATURE:
<223> OTHER INFORMATION: Oligo for detecting mutation with a G at -continued position 16,263 of SEQ ID NO:1

<400> SEQUENCE: 127
caggacgaca tttattag                                                 18

<210> SEQ ID NO 128
<211> LENGTH: 18
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 128
ccaggacgac atttatta                                                 18

<210> SEQ ID NO 129
<211> LENGTH: 18
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 129
accaggacga catttatt                                                 18

<210> SEQ ID NO 130
<211> LENGTH: 18
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 130
caccaggacg acatttat                                                 18

<210> SEQ ID NO 131
<211> LENGTH: 18
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 131
ccaccaggac gacattta                                                 18

<210> SEQ ID NO 132
<211> LENGTH: 18
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 132
tccaccagga cgacattt                                                 18

<210> SEQ ID NO 133
<211> LENGTH: 18
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

```
<400> SEQUENCE: 133
gtccaccagg acgacatt                                                18

<210> SEQ ID NO 134
<211> LENGTH: 18
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 134
tgtccaccag gacgacat                                                18

<210> SEQ ID NO 135
<211> LENGTH: 18
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 135
ctgtccacca ggacgaca                                                18

<210> SEQ ID NO 136
<211> LENGTH: 19
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 136
gacgacattt attagggga                                               19

<210> SEQ ID NO 137
<211> LENGTH: 19
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 137
ggacgacatt tattagggg                                               19

<210> SEQ ID NO 138
<211> LENGTH: 19
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 138
aggacgacat ttattaggg                                               19

<210> SEQ ID NO 139
<211> LENGTH: 19
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1
```

<400> SEQUENCE: 139
caggacgaca tttattagg                          19

<210> SEQ ID NO 140
<211> LENGTH: 19
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 140
ccaggacgac atttattag                          19

<210> SEQ ID NO 141
<211> LENGTH: 19
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 141
accaggacga catttatta                          19

<210> SEQ ID NO 142
<211> LENGTH: 19
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 142
caccaggacg acatttatt                          19

<210> SEQ ID NO 143
<211> LENGTH: 19
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 143
ccaccaggac gacatttat                          19

<210> SEQ ID NO 144
<211> LENGTH: 19
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 144
tccaccagga cgacattta                          19

<210> SEQ ID NO 145
<211> LENGTH: 19
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 145

```
gtccaccagg acgacattt                                                    19
```

<210> SEQ ID NO 146
<211> LENGTH: 19
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 146

```
tgtccaccag gacgacatt                                                    19
```

<210> SEQ ID NO 147
<211> LENGTH: 19
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 147

```
ctgtccacca ggacgacat                                                    19
```

<210> SEQ ID NO 148
<211> LENGTH: 19
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 148

```
tctgtccacc aggacgaca                                                    19
```

<210> SEQ ID NO 149
<211> LENGTH: 20
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 149

```
gacgacattt attaggggac                                                   20
```

<210> SEQ ID NO 150
<211> LENGTH: 20
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 150

```
ggacgacatt tattagggga                                                   20
```

<210> SEQ ID NO 151
<211> LENGTH: 20
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 151
aggacgacat ttattagggg                                       20

<210> SEQ ID NO 152
<211> LENGTH: 20
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 152
caggacgaca tttattaggg                                       20

<210> SEQ ID NO 153
<211> LENGTH: 20
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 153
ccaggacgac atttattagg                                       20

<210> SEQ ID NO 154
<211> LENGTH: 20
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 154
accaggacga catttattag                                       20

<210> SEQ ID NO 155
<211> LENGTH: 20
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 155
caccaggacg acatttatta                                       20

<210> SEQ ID NO 156
<211> LENGTH: 20
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 156
ccaccaggac gacatttatt                                       20

<210> SEQ ID NO 157
<211> LENGTH: 20
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 157
tccaccagga cgacatttat                                       20

```
<210> SEQ ID NO 158
<211> LENGTH: 20
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 158
gtccaccagg acgacattta                                              20

<210> SEQ ID NO 159
<211> LENGTH: 20
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 159
tgtccaccag gacgacattt                                              20

<210> SEQ ID NO 160
<211> LENGTH: 20
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 160
ctgtccacca ggacgacatt                                              20

<210> SEQ ID NO 161
<211> LENGTH: 20
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 161
tctgtccacc aggacgacat                                              20

<210> SEQ ID NO 162
<211> LENGTH: 20
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 162
atctgtccac caggacgaca                                              20

<210> SEQ ID NO 163
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 163
gacgacattt attaggggac g                                            21
```

<210> SEQ ID NO 164
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 164
ggacgacatt tattagggga c                                           21

<210> SEQ ID NO 165
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 165
aggacgacat ttattagggg a                                           21

<210> SEQ ID NO 166
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 166
caggacgaca tttattaggg g                                           21

<210> SEQ ID NO 167
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 167
ccaggacgac atttattagg g                                           21

<210> SEQ ID NO 168
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 168
accaggacga catttattag g                                           21

<210> SEQ ID NO 169
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 169
caccaggacg acatttatta g                                           21

```
<210> SEQ ID NO 170
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 170
ccaccaggac gacatttatt a                                              21

<210> SEQ ID NO 171
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 171
tccaccagga cgacatttat t                                              21

<210> SEQ ID NO 172
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 172
gtccaccagg acgacattta t                                              21

<210> SEQ ID NO 173
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 173
tgtccaccag gacgacattt a                                              21

<210> SEQ ID NO 174
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 174
ctgtccacca ggacgacatt t                                              21

<210> SEQ ID NO 175
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 175
tctgtccacc aggacgacat t                                              21
```

```
<210> SEQ ID NO 176
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 176
atctgtccac caggacgaca t                                              21

<210> SEQ ID NO 177
<211> LENGTH: 21
<212> TYPE: DNA
<213> ORGANISM: Artificial Sequence
<220> FEATURE:
<223> OTHER INFORMATION: Oligo for detecting mutation with a G at
      position 16,263 of SEQ ID NO:1

<400> SEQUENCE: 177
tatctgtcca ccaggacgac a                                              21

<210> SEQ ID NO 178
<211> LENGTH: 41
<212> TYPE: PRT
<213> ORGANISM: Homo sapiens

<400> SEQUENCE: 178

Asp Ile Asn Glu Cys Glu Gln Val Pro Lys Pro Cys Ala His Gln Cys
  1               5                  10                  15

Ser Asn Thr Pro Gly Ser Phe Lys Cys Ile Cys Pro Pro Gly Gln His
             20                  25                  30

Leu Leu Gly Asp Gly Lys Ser Cys Ala
         35                  40

<210> SEQ ID NO 179
<211> LENGTH: 41
<212> TYPE: PRT
<213> ORGANISM: Mus musculus

<400> SEQUENCE: 179

Asp Ile Asn Glu Cys Glu Gln Val Pro Lys Pro Cys Ala His Gln Cys
  1               5                  10                  15

Ser Asn Ser Pro Gly Ser Phe Lys Cys Ile Cys Leu Pro Gly Gln Gln
             20                  25                  30

Leu Leu Gly Asp Gly Lys Ser Cys Ala
         35                  40

<210> SEQ ID NO 180
<211> LENGTH: 40
<212> TYPE: PRT
<213> ORGANISM: Sus scrofa

<400> SEQUENCE: 180

Ile Asn Glu Cys Glu Gln Val Pro Lys Pro Cys Ala Tyr Gln Cys Ser
  1               5                  10                  15

Asn Thr Pro Gly Ser Phe Lys Cys Ile Cys Pro Pro Gly Gln His Leu
             20                  25                  30

Leu Gly Asp Gly Lys Ser Cys Ala
         35                  40
```

```
<210> SEQ ID NO 181
<211> LENGTH: 30
<212> TYPE: PRT
<213> ORGANISM: Rattus norvegicus

<400> SEQUENCE: 181

Cys Ala His Gln Cys Ser Asn Ser Pro Gly Ser Phe Lys Cys Ile Cys
 1               5                  10                  15

Leu Pro Gly Gln His Leu Leu Gly Asp Gly Lys Ser Cys Ala
            20                  25                  30

<210> SEQ ID NO 182
<211> LENGTH: 24
<212> TYPE: PRT
<213> ORGANISM: Felis domestica

<400> SEQUENCE: 182

Asn Thr Pro Gly Ser Phe Lys Cys Ile Cys Pro Pro Gly Gln His Leu
 1               5                  10                  15

Leu Gly Asp Gly Lys Ser Cys Ala
            20

<210> SEQ ID NO 183
<211> LENGTH: 30
<212> TYPE: PRT
<213> ORGANISM: Canis familiaris

<400> SEQUENCE: 183

Cys Ala Tyr Gln Cys Ser Asn Thr Pro Gly Ser Phe Lys Cys Ile Cys
 1               5                  10                  15

Pro Pro Gly Gln His Leu Leu Gly Asp Gly Lys Ser Cys Ala
            20                  25                  30

<210> SEQ ID NO 184
<211> LENGTH: 25
<212> TYPE: PRT
<213> ORGANISM: Ovis aries

<400> SEQUENCE: 184

Phe Asn Thr Pro Gly Ser Phe Lys Cys Ile Cys Pro Pro Gly Gln His
 1               5                  10                  15

Leu Leu Gly Asp Gly Lys Ser Cys Ala
            20                  25

<210> SEQ ID NO 185
<211> LENGTH: 23
<212> TYPE: PRT
<213> ORGANISM: Oryctolagus cuniculus

<400> SEQUENCE: 185

Thr Pro Gly Ser Phe Lys Cys Thr Cys Pro Pro Gly Gln His Leu Leu
 1               5                  10                  15

Gly Asp Gly Lys Ser Cys Ala
            20

<210> SEQ ID NO 186
<211> LENGTH: 30
<212> TYPE: PRT
<213> ORGANISM: Gallus gallus
```

```
-continued
<400> SEQUENCE: 186

Cys Ala Phe Gln Cys Thr Asn Thr Pro Gly Ser Phe Lys Cys Ile Cys
1               5                   10                  15

Pro Pro Gly Gln His Leu Leu Gly Asp Gly Lys Ser Cys Ala
            20                  25                  30
```